United States Patent
Wang et al.

(10) Patent No.: US 11,840,535 B2
(45) Date of Patent: Dec. 12, 2023

(54) ALKYNYL(HETERO)AROMATIC COMPOUND FOR INHIBITING PROTEIN KINASE ACTIVITY

(71) Applicant: Shenzhen TargetRx, Inc., Guangdong (CN)

(72) Inventors: Yihan Wang, Guangdong (CN); Qingfeng Xing, Guangdong (CN)

(73) Assignee: Shenzhen TargetRx, Inc., Guangdong (CN)

( * ) Notice: Subject to any disclaimer, the term of this patent is extended or adjusted under 35 U.S.C. 154(b) by 242 days.

(21) Appl. No.: 17/253,968

(22) PCT Filed: Jun. 28, 2019

(86) PCT No.: PCT/CN2019/093469
§ 371 (c)(1),
(2) Date: Dec. 18, 2020

(87) PCT Pub. No.: WO2020/007234
PCT Pub. Date: Jan. 9, 2020

(65) Prior Publication Data
US 2021/0284646 A1 Sep. 16, 2021

(30) Foreign Application Priority Data
Jul. 2, 2018 (CN) .......................... 201810707422.0

(51) Int. Cl.
C07D 487/04 (2006.01)
A61K 45/06 (2006.01)

(52) U.S. Cl.
CPC ............ *C07D 487/04* (2013.01); *A61K 45/06* (2013.01)

(58) Field of Classification Search
CPC .................................................. C07D 487/04
See application file for complete search history.

(56) References Cited

U.S. PATENT DOCUMENTS

| 9,108,973 B2 | 8/2015 | Sagara et al. |
| 9,682,083 B2 | 6/2017 | Angiolini et al. |

FOREIGN PATENT DOCUMENTS

| CN | 103044432 A | 4/2013 | |
| CN | 103958512 A | 7/2014 | |
| CN | 105431436 A | 3/2016 | |
| CN | 105602254 A | 5/2016 | |
| CN | 105431436 B | * 11/2017 | .......... A61K 31/496 |
| JP | 2009-521462 A | 6/2009 | |
| JP | 2009-524671 A | 7/2009 | |
| JP | 2015-514802 A | 5/2015 | |
| JP | 2016-518419 A | 6/2016 | |
| JP | 2018-506579 A | 3/2018 | |
| WO | WO 2013/162727 A1 | 10/2013 | |
| WO | WO 2017/111074 A1 | 6/2017 | |
| WO | WO 2018/033091 A1 | 2/2018 | |
| WO | WO 2018/068739 A1 | 4/2018 | |

OTHER PUBLICATIONS

Japanese Office Action for Application No. 2021-500057, dated Mar. 15, 2022.
PCT/CN2019/093469, Sep. 27, 2019, International Search Report and Written Opinion and English translations thereof.
International Search Report and Written Opinion for Application No. PCT/CN2019/093469, dated Sep. 27, 2019.

* cited by examiner

*Primary Examiner* — Michael Barker
*Assistant Examiner* — Jed A Kucharczk
(74) *Attorney, Agent, or Firm* — Wolf, Greenfield & Sacks, P.C.

(57) ABSTRACT

Provided is an alkynyl(hetero)aromatic compound having an inhibitory effect to protein tyrosine kinase, a pharmaceutical composition comprising same, preparation and usage thereof. Specifically, disclosed is an alkynyl(hetero)aromatic compound as shown in formula (I), wherein rings A, $R_1$, $R_2$, $R_3$, $R_4$, $R_5$, L, and B are defined in the description, a pharmaceutically acceptable salt, a stereoisomer, a solvate, a hydrate, a crystal form, a prodrug or an isotopic variant thereof. The compound can be used for treating and/or preventing protein tyrosine kinase-related diseases, such as anti-tumor.

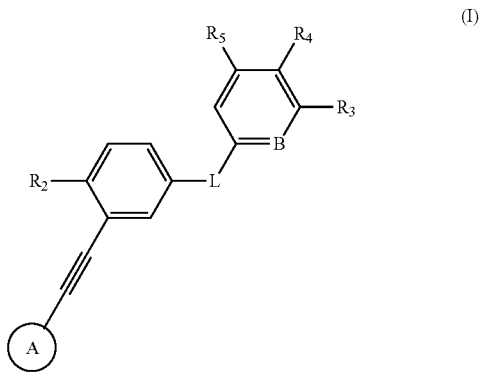

18 Claims, No Drawings

ALKYNYL(HETERO)AROMATIC COMPOUND FOR INHIBITING PROTEIN KINASE ACTIVITY

CROSS REFERENCE TO RELATED APPLICATIONS

The present application is a national application of PCT/CN2019/093469 filed on Jun. 28, 2019, which claims the priority of the Chinese Patent Application No. 201810707422.0 filed on Jul. 2, 2018. The Chinese Patent Application No. 201810707422.0 is incorporated herein by reference as part of the disclosure of the present application.

TECHNICAL FIELD

The present disclosure belongs to the pharmaceutical technical field, and particularly relates to alkynyl (hetero) aromatic compounds having inhibition effect on protein kinase activity, to pharmaceutical compositions containing the same, to preparation methods and use thereof.

BACKGROUND OF THE INVENTION

Protein tyrosine kinases (PTKs) are a kind of kinases that can catalyze the transfer of γ-phosphate on ATP to protein tyrosine residues and activate a protein enzyme system that functions as a functional protein by catalyzing the phosphorylation of phenolic hydroxyl groups on various protein tyrosine residues. Protein tyrosine kinase is very important in the intracellular signaling pathway, which can regulate a series of physiological and biochemical processes such as cell growth, differentiation, and death. Abnormal expression of protein tyrosine kinase can lead to disorder of cell proliferation regulation, which in turn leads to the occurrence of tumors. In addition, the abnormal expression of protein tyrosine kinases is also closely related to tumor invasion and metastasis, tumor angiogenesis, and tumor resistance to chemotherapy. Protein kinases have become important targets of disease treatment. A non-limiting list of such kinases includes Ret(Reaaranged during transfection), ABL1(E255K)-phosphorylated, ABL1(F317I)-phosphorylated, ABL1(F317L)-phosphorylated, ABL1(H396P)-phosphorylated, ABL1(F317I)-nonphosphorylated, ABL1(F3-17L)-nonphosphorylated, ABL1(H396P)-nonphosphorylated, ABL1(M351T)-phosphorylated, ABL1(Q252H)-nonphosphorylated, ABL1(Q252H)-phosphorylated, ABL1(T315I)-nonphosphorylated, ABL1(T315I)-phosphorylated, ABL1(Y253F)-phosphorylated, ABL1-nonphosphorylated, ABL1-phosphorylated, AB L2, ALK(L1196M), AMPK-alpha1, AMPK-alpha2, ANKK1, AURKB, AURKC, AXL, BLK, BMX, BRAF, BRAF(V600E), BRK, BTK, CAMK1, CAMKK1, CAMKK2, CDC2L1, CDC2L2, CDC2L5, CDK11, CDK2, CDK5, CDK7, CDK8, CDKL1, CDKL2, CDKL3, CHEK2, CIT, CLK1, CLK4, CSF1R, CSK, CTK, DDR1, DDR2, DLK, EGFR, EGFR(E746-A750del), EGFR (G719C), EGFR(G719S), EGFR(L747-E749del, A750P), EGFR(L747-S752del, P753S), EGFR(L747-T751del,Sins), EGFR(L858R), EGFR(L858R,T790M), EGFR(L861Q), EGFR(S752-1759del), EGFR(T790M), EPHA1, EPHA2, EPHA3, EPHA4, EPHA5, EPHA6, EPHA7, EPHA8, EPHB1, EPHB2, EPHB4, EPHB6, ERBB2, ERBB4, ERK8, FAK, FER, FES, FGFR1, FGFR2, FGFR3, FGFR3(G697C), FGFR4, FGR, FLT1, FLT3, FLT3(D835H), FLT3(D835V), FLT3(D835Y), FLT3(ITD), FLT3(ITD,D835V), FLT3(ITD, F691L), FLT3(K663Q), FLT3(N841I), FLT3(R834Q), FLT4, FRK, FYN, GAK, GCN2(Kin.Dom.2,S808G), HCK, HIPK4, HPK1, IKK-alpha, IKK-beta, IRAK1, IRAK4, ITK, JAK1(JH1domain-catalytic), JAK2(JH1domain-catalytic), JAK3(JH1domain-catalytic), JNK1, JNK2, JNK3, KIT, KIT (A829P), KIT(D816H), KIT(D816V), KIT(L576P), KIT (V559D), KIT(V559D,T670I), KIT(V559D,V654A), LCK, LIMK1, LIMK2, LOK, LRRK2, LRRK2(G2019S), LTK, LYN, MAK, MAP3K2, MAP3K3, MAP4K2, MAP4K3, MAP4K4, MAP4K5, MEK5, MELK, MERTK, MET, MET (M1250T), MINK, MKNK2, MLK1, MLK2, MLK3, MST1, MST1R, MST2, MUSK, MYLK2, MYO3A, MYO3B, NDR2, NEK1, NEK11, NEK4, NEK5, NEK9, NLK, p38-alpha, p38-beta, p38-delta, p38-gamma, PCTK2, PDGFRA, PDGFRB, PFCDPK1(P.falciparum), PFTAIRE2, PFTK1, PKAC-alpha, PKAC-beta, PYK2, RAF1, RET, RET(M918T), RET(V804L), RET(V804M), RIPK1, RIPK2, RIPK4, ROCK2, RPS6KA4(Kin.Dom.1-N-terminal), RSK2(Kin.Dom.1-N-terminal), RSK3(Kin.DoN-terminal), S6K1, SIK, SLK, SRC, SRMS, SRPK1, STK33, STK35, STK36, SYK, TAK1, TAOK2, TAOK3, TEC, TESK1, TGFBR2, TIE1, TIE2, TNIK, TNK1, TNK2, TNNI3K, TRKA, TRKB, TRKC, TTK, TXK, TYK2 (JH1domain-catalytic), TYRO3, ULK3, VEGFR2, YES, YSK4, ZAK, ZAP70 or FGFR(Fibroblast growth factor receptor). Abnormal protein kinase activity is associated with a variety of diseases, ranging from non-life-threatening diseases such as psoriasis to extremely serious diseases such as cancer.

Considering such a large number of protein kinases and numerous diseases related to protein kinases, there is always a need in new types of compounds with increased selectivity. These compounds can be used as protein kinase inhibitors and thus used in the treatment of protein tyrosine-related diseases.

The present disclosure relates to a new family of alkynyl heteroaromatic compounds and their use in the treatment of cancer, bone diseases, metabolic diseases, inflammatory diseases and other diseases.

SUMMARY OF THE INVENTION

The present disclosure provides a new alkynyl (hetero) aromatic compound and a composition containing the same and use thereof. The compound has a wide range of biological and pharmacological activities, especially potent inhibitory activity against Abl kinase and its mutant type kinases.

In this regard, the present disclosure adopts the following technical solutions:

In the first aspect, the present disclosure provides a compound of formula (I):

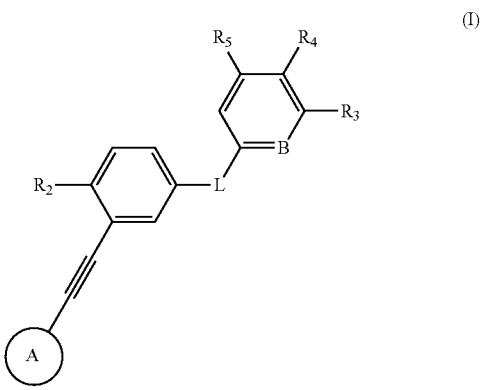

wherein, ring A is selected from the group consisting of ring A-1, A-2 and A-3 with the following structures:

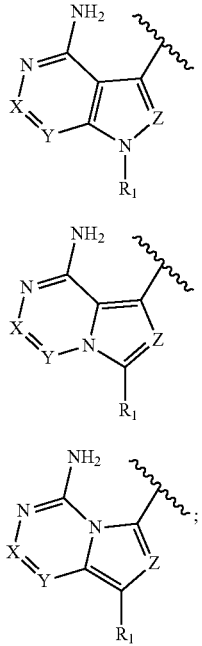

X, Y and Z are independently selected from CH or N; provided that ring A is not

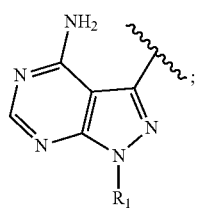

$R_1$ is selected from H, $C_{1-6}$ alkyl, $C_{3-7}$ cycloalkyl, 3- to 7-membered heterocyclyl, $C_{6-10}$ aryl or 5- to 10-membered heteroaryl; wherein the groups are optionally substituted by one or more $R_{1a}$; provided that when A is A-1, $R_1$ is not H;

$R_2$ is selected from H, CN, $NO_2$, OH, halogen, $C_{1-6}$ alkyl, $C_{1-6}$ haloalkyl, $C_{1-6}$ alkoxy or $C_{1-6}$ haloalkoxy;

L is selected from —C(O)N($R_{1b}$)—, —N($R_{1b}$)C(O)— or —N($R_{1b}$)C(O)N($R_{1b}$)—;

B is selected from CH or N;

$R_3$ is selected from H, $C_{1-6}$ alkyl or $C_{1-6}$ haloalkyl;

$R_4$ and $R_5$ are selected from:

1) $R_5$ is H, $R_4$ is selected from H, $C_{1-6}$ alkyl, —$CO_{0-2}$ alkylene-$C_{3-7}$ cycloalkyl, —$CO_{0-2}$ alkylene-3- to 7-membered heterocyclyl or —$CO_{0-2}$ alkylene-$NR_{1c}R_{2c}$, wherein the groups are optionally substituted by one or more $R_{1d}$; or 2) $R_4$ is H, $R_5$ is selected from H or 5- to 6-membered heteroaryl ring containing one or more N, O or S heteroatoms, wherein the said 5- to 6-membered heteroaryl ring is optionally substituted by one or more $R_{1d}$;

each $R_{1a}$ is independently selected from H, halogen, oxo, —$CO_{0-6}$ alkylene-$OR_a$, —$C_{0-6}$ alkylene-$NR_bR_c$, —$CO_{0-6}$ alkylene-C(O)$R_a$, —$C_{0-6}$ alkylene-C(O)$OR_a$, —$CO_{0-6}$ alkylene-C(O)$NR_bR_c$, $C_{1-6}$ alkyl, $C_{1-6}$ haloalkyl, —$CO_{0-6}$ alkylene-$C_{3-6}$ cycloalkyl or —$CO_{0-6}$ alkylene-3- to 7-membered heterocyclyl; or two or more $R_{1a}$ together with the atom to which they attached form a $C_{3-7}$ cycloalkyl or 3- to 7-membered heterocyclyl;

each $R_{1b}$ is independently selected from H, —$CO_{0-6}$ alkylene-$OR_a$, —$CO_{0-6}$ alkylene-$NR_bR_c$, —$C_{0-6}$ alkylene-C(O)$R_a$, —$C_{0-6}$ alkylene-C(O)$OR_a$, —$C_{0-6}$ alkylene-C(O)$NR_bR_c$, $C_{1-6}$ alkyl, $C_{1-6}$ haloalkyl, —$CO_{0-6}$ alkylene-$C_{3-6}$ cycloalkyl or —$CO_{0-6}$ alkylene-3- to 7-membered heterocyclyl; or two or more $R_{1b}$ together with the atom to which they attached form a $C_{3-7}$ cycloalkyl or 3- to 7-membered heterocyclyl;

$R_{1c}$ and $R_{2c}$ are each independently selected from H, halogen, —$C_{0-6}$ alkylene-CN, —$CO_{0-6}$ alkylene-$OR_a$, —$C_{0-6}$ alkylene-$SR_a$, —$C_{0-6}$ alkylene-$NR_bR_c$, —$C_{0-6}$ alkylene-C(O)$R_a$, —$C_{0-6}$ alkylene-C(O)$OR_a$, —$CO_{0-6}$ alkylene-C(O)$NR_bR_c$, $C_{1-6}$ alkyl, $C_{1-6}$ haloalkyl, $C_{2-6}$ alkenyl, $C_{2-6}$ alkynyl, —$CO_{0-6}$ alkylene-$C_{3-6}$ cycloalkyl, —$CO_{0-6}$ alkylene-3- to 7-membered heterocyclyl, —$C_{0-6}$ alkylene-$C_{6-10}$ aryl or —$CO_{0-6}$ alkylene-5- to 10-membered heteroaryl; alternatively, $R_{1c}$, $R_{2c}$ together with the nitrogen atom to which they attached form a $C_{3-7}$ cycloalkyl or 3- to 7-membered heterocyclyl;

each $R_{1d}$ is independently selected from H, halogen, —$CO_{0-6}$ alkylene-CN, —$C_{0-6}$ alkylene-$OR_a$, —$CO_{0-6}$ alkylene-$SR_a$, —$CO_{0-6}$ alkylene-$NR_bR_c$, —$CO_{0-6}$ alkylene-C(O)$R_a$, —$C_{0-6}$ alkylene-C(O)$OR_a$, —$CO_{0-6}$ alkylene-C(O)$NR_bR_c$, $C_{1-6}$ alkyl, $C_{1-6}$ haloalkyl, $C_{2-6}$ alkenyl, $C_{2-6}$ alkynyl, —$CO_{0-6}$ alkylene-$C_{3-6}$ cycloalkyl, —$CO_{0-6}$ alkylene-3- to 7-membered heterocyclyl, —$C_{0-6}$ alkylene-$C_{6-10}$ aryl or —$CO_{0-6}$ alkylene-5- to 10-membered heteroaryl; alternatively, two or more $R_{1d}$ together with the atom to which they attached form a $C_{3-7}$ cycloalkyl or 3- to 7-membered heterocyclyl;

$R_a$, $R_b$ or $R_c$ are independently selected from H, $C_{1-6}$ alkyl, $C_{1-6}$ haloalkyl, $C_{3-7}$ cycloalkyl, 3- to 7-membered heterocyclyl, $C_{6-10}$ aryl or 5- to 10-membered heteroaryl;

[0022] provided that, the above compounds do not comprise the following structures:

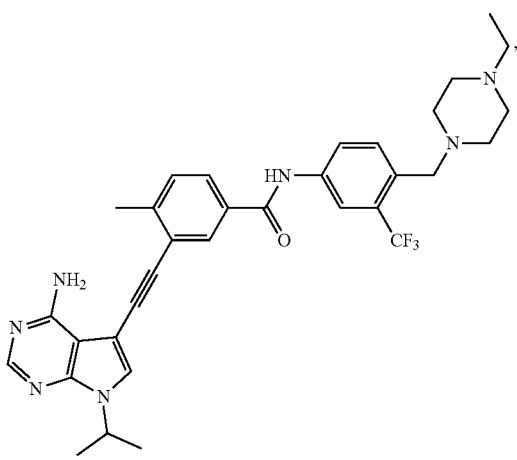

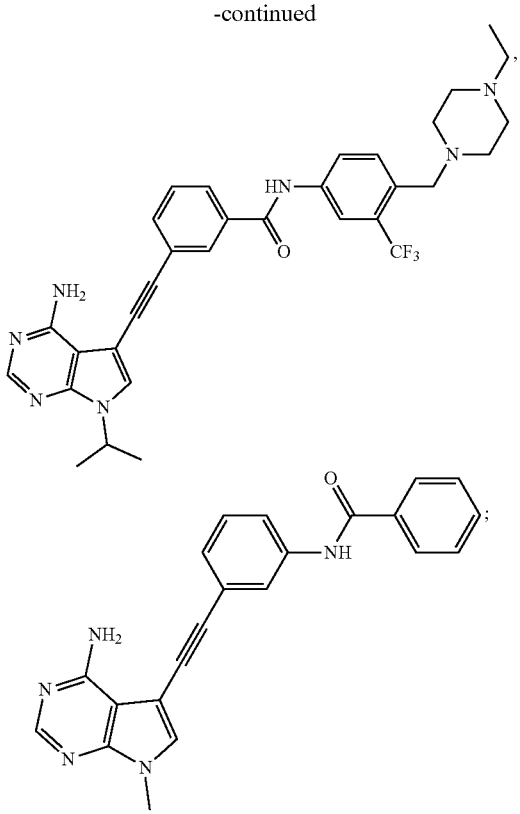

or the pharmaceutically acceptable salts, stereoisomers, solvates, hydrates, crystal forms, prodrugs or isotopic variants thereof.

In another aspect, the present disclosure provides a pharmaceutical composition comprising a compound of the present disclosure and pharmaceutically acceptable excipient(s).

In a specific embodiment, the compound of the present disclosure is provided in the pharmaceutical composition in an effective amount. In a specific embodiment, the compound of the present disclosure is provided in a therapeutically effective amount. In a specific embodiment, the compound of the present disclosure is provided in a prophylactically effective amount.

In another aspect, the present disclosure provides a pharmaceutical composition comprising a compound of the present disclosure and pharmaceutically acceptable excipient(s), which also contains other therapeutic agent(s).

In another aspect, the present disclosure provides a kit comprising a compound of the present disclosure or the pharmaceutically acceptable salts, stereoisomers, solvates, hydrates, crystal forms, prodrugs or isotopic variants thereof, optionally other therapeutic agent(s) and pharmaceutically acceptable carrier(s), adjuvant(s) or vehicle(s).

In another aspect, the present disclosure provides a method for treating a protein kinase-related disease in a subject, the method includes administering to the subject a compound of the present disclosure or the pharmaceutically acceptable salts, stereoisomers, solvates, hydrates, crystal forms, prodrugs or isotopic variants thereof, or the pharmaceutical composition. In a specific embodiment, the protein kinase is selected from Ret(Reaaranged during transfection), ABL1(E255K)-phosphorylated, ABL1(F317I)-nonphosphorylated, ABL1(F317I)-phosphorylated, ABL1(F317L)-phosphorylated, ABL1(H396P)-phosphorylated, ABL1(Q252H)-nonphosphorylated, ABL1(T315I)-nonphosphorylated, ABL1(F317L)-nonphosphorylated, ABL1(H396P)-nonphosphorylated, ABL1(M351T)-phosphorylated, ABL1(Q252H)-phosphorylated, ABL1(T315I)-phosphorylated, ABL1(Y253F)-phosphorylated, ABL1-nonphosphorylated, ABL1-phosphorylated, AB L2, ALK (L1196M), AMPK-alpha1, AMPK-alpha2, ANKK1, AURKB, AURKC, AXL, BLK, BMX, BRAF, BRAF (V600E), BRK, BTK, CAMK1, CAMKK1, CAMKK2, CDC2L1, CDC2L2, CDC2L5, CDK11, CDK2, CDK5, CDK7, CDK8, CDKL1, CDKL2, CDKL3, CHEK2, CIT, CLK1, CLK4, CSF1R, CSK, CTK, DDR1, DDR2, DLK, EGFR, EGFR(E746-A750del), EGFR(G719C), EGFR (G719S), EGFR(L747-E749del, A750P), EGFR(L747-S752del, P753S), EGFR(L747-T751del,Sins), EGFR (L858R), EGFR(L858R,T790M), EGFR(L861Q), EGFR (S752-I759del), EGFR(T790M), EPHA1, EPHA2, EPHA3, EPHA4, EPHA5, EPHA6, EPHA7, EPHA8, EPHB1, EPHB2, EPHB4, EPHB6, ERBB2, ERBB4, ERK8, FAK, FER, FES, FGFR1, FGFR2, FGFR3, FGFR3(G697C), FGFR4, FGR, FLT1, FLT3, FLT3(D835H), FLT3(D835V), FLT3(D835Y), FLT3(ITD), FLT3(ITD,D835V), FLT3(ITD, F691L), FLT3(K663Q), FLT3(N841I), FLT3(R834Q), FLT4, FRK, FYN, GAK, GCN2(Kin.Dom.2,S808G), HCK, HIPK4, HPK1, IKK-alpha, IKK-beta, IRAK1, IRAK4, ITK, JAK1(JH1domain-catalytic), JAK2(JH1domain-catalytic), JAK3(JH1domain-catalytic), JNK1, JNK2, JNK3, KIT, KIT (A829P), KIT(D816H), KIT(D816V), KIT(L576P), KIT (V559D), KIT(V559D,T670I), KIT(V559D,V654A), LCK, LIMK1, LIMK2, LOK, LRRK2, LRRK2(G2019S), LTK, LYN, MAK, MAP3K2, MAP3K3, MAP4K2, MAP4K3, MAP4K4, MAP4K5, MEK5, MELK, MERTK, MET, MET (M1250T), MINK, MKNK2, MLK1, MLK2, MLK3, MST1, MST1R, MST2, MUSK, MYLK2, MYO3A, MYO3B, NDR2, NEK1, NEK11, NEK4, NEK5, NEK9, NLK, p38-alpha, p38-beta, p38-delta, p38-gamma, PCTK2, PDGFRA, PDGFRB, PFCDPK1(P.falciparum), PFTAIRE2, PFTK1, PKAC-alpha, PKAC-beta, PYK2, RAF1, RET, RET(M918T), RET(V804L), RET(V804M), RIPK1, RIPK2, RIPK4, ROCK2, RPS6KA4(Kin.Dom.1-N-terminal), RSK2(Kin.Dom.1-N-terminal), RSK3(Kin.DoN-terminal), S6K1, SIK, SLK, SRC, SRMS, SRPK1, STK33, STK35, STK36, SYK, TAK1, TAOK2, TAOK3, TEC, TESK1, TGFBR2, TIE1, TIE2, TNIK, TNK1, TNK2, TNNI3K, TRKA, TRKB, TRKC, TTK, TXK, TYK2 (JH1domain-catalytic), TYRO3, ULK3, VEGFR2, YES, YSK4, ZAK, ZAP70 or FGFR(Fibroblast growth factor receptor).

In another aspect, the present disclosure provides a use of the compound of the present disclosure in the preparation of a medicament for tumor or other diseases. In a specific embodiment, the disease is a proliferative disease caused by Bcr-Abl. In a specific embodiment, the disease can be selected from: solid tumor, sarcoma, chronic myelogenous leukemia, chronic granulocytic leukemia, gastrointestinal stromal tumor, acute granulocytic leukemia, thyroid cancer, gastric cancer, rectal cancer, multiple myeloma, neoplasia, and other hyperplastic or proliferative diseases. In a specific embodiment, the condition caused by Bcr-Abl is chronic granulocytic leukemia, gastrointestinal stromal tumor, acute granulocytic leukemia, thyroid cancer or a combination thereof. In a specific embodiment, the compound is administered orally, subcutaneously, intravenously or intramuscularly. In a specific embodiment, the compound is administered chronically.

From the following specific embodiments, examples and claims, other objects and advantages of the present disclosure will be obvious to those skilled in the art.

Definitions

Chemical Definitions

Definitions of specific functional groups and chemical terms are described in more detail below.

When a range of values is listed, it is intended to encompass each value and sub-range within the range. For example "$C_{1-6}$ alkyl" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$ and $C_{5-6}$ alkyl.

"$C_{1-6}$ alkyl" refers to a radical of a straight-chain or branched saturated hydrocarbon group having from 1 to 6 carbon atoms, and it is also referred to herein as "lower alkyl". In some embodiments, $C_{1-4}$ alkyl is particularly preferred. Examples of alkyl groups include, but are not limited to, methyl ($C_1$), ethyl ($C_2$), n-propyl ($C_3$), isopropyl ($C_3$), n-butyl ($C_4$), tert-butyl ($C_4$), sec-butyl ($C_4$), iso-butyl ($C_4$), n-pentyl ($C_5$), 3-pentanyl ($C_5$), amyl ($C_5$), neopentyl ($C_5$), 3-methyl-2-butanyl ($C_5$), tertiary amyl ($C_5$), and n-hexyl ($C_6$). Regardless of whether the alkyl group is modified with "substituted", each instance of an alkyl group is independently optionally substituted, e.g., for instance with from 1 to 5 substituents, 1 to 3 substituents, or 1 substituent. Appropriate substituents are defined below.

"$C_{2-6}$ alkenyl" refers to a radical of a straight-chain or branched hydrocarbon group having from 2 to 6 carbon atoms, and one or more carbon-carbon double bonds (e.g., 1, 2, or 3 carbon-carbon double bonds). The one or more carbon-carbon double bonds may be internal (such as in 2-butenyl) or terminal (such as in 1-butenyl). In some embodiments, $C_{2-4}$ alkenyl is particularly preferred. Examples of alkenyl groups include, but are not limited to, ethenyl ($C_2$), 1-propenyl ($C_3$), 2-propenyl ($C_3$), 1-butenyl ($C_4$), 2-butenyl ($C_4$), butadienyl ($C_4$), pentenyl ($C_5$), pentadienyl ($C_5$), hexenyl ($C_6$), and the like. Regardless of whether the alkenyl group is modified with "substituted", each instance of an alkenyl group is independently optionally substituted, e.g., for instance with from 1 to 5 substituents, 1 to 3 substituents, or 1 substituent. Appropriate substituents are defined below.

"$C_{2-6}$ alkynyl" refers to a radical of a straight-chain or branched hydrocarbon group having from 2 to 6 carbon atoms, one or more carbon-carbon triple bonds (e.g., 1, 2, or 3 carbon-carbon triple bonds), and optionally one or more carbon-carbon double bonds (e.g., 1, 2, or 3 carbon-carbon double bonds). In some embodiments, $C_{2-4}$ alkynyl is particularly preferred. In some embodiments, alkynyl does not contain any double bonds. The one or more carbon-carbon triple bonds may be internal (such as in 2-butynyl) or terminal (such as in 1-butynyl). Examples of the alkynyl groups include, but are not limited to, ethynyl ($C_2$), 1-propynyl ($C_3$), 2-propynyl ($C_3$), 1-butynyl ($C_4$), 2-butynyl ($C_4$), pentynyl ($C_5$), hexynyl ($C_6$), and the like. Regardless of whether the alkynyl group is modified with "substituted", each instance of an alkynyl group is independently optionally substituted, e.g., for instance with from 1 to 5 substituents, 1 to 3 substituents, or 1 substituent. Appropriate substituents are defined below.

"$C_{1-6}$ alkylene" refers to a divalent group formed by removing another hydrogen of the $C_{1-6}$ alkyl, and can be a substituted or unsubstituted alkylene. In some embodiments, $C_{1-4}$ alkylene is particularly preferred. The unsubstituted alkylene groups include, but are not limited to, methylene (—$CH_2$—), ethylene (—$CH_2CH_2$—), propylene (—$CH_2CH_2CH_2$—), butylene (—$CH_2CH_2CH_2CH_2$—), pentylene (—$CH_2CH_2CH_2CH_2CH_2$—), hexylene (—$CH_2CH_2CH_2CH_2CH_2CH_2$—), etc. Examples of substituted alkylene groups, such as those substituted with one or more alkyl (methyl) groups, include, but are not limited to, substituted methylene (—CH($CH_3$)—, —C($CH_3$)$_2$—), substituted ethylene (—CH($CH_3$)$CH_2$—, —$CH_2$CH($CH_3$)—, —C($CH_3$)$_2$$CH_2$—, —$CH_2$C($CH_3$)$_2$—), substituted propylene (—CH($CH_3$)$CH_2CH_2$—, -$CH_2$CH($CH_3$)$CH_2$—, —$CH_2CH_2$CH($CH_3$)—, —C($CH_3$)$_2$$CH_2CH_2$—, —$CH_2$C($CH_3$)$_2$$CH_2$—, —$CH_2CH_2$C($CH_3$)$_2$—), etc.

"$C_{0-6}$ alkylene" includes the chemical bond and $C_{1-6}$ alkylene groups as defined above.

"$C_{1-6}$ alkoxy" refers to the group —OR wherein R is a substituted or unsubstituted $C_{1-6}$ alkyl group. In some embodiments, $C_{1-4}$ alkoxy group is particularly preferred. Specific alkoxy groups include, but are not limited to, methoxy, ethoxy, n-propoxy, isopropoxy, n-butoxy, tert-butoxy, sec-butoxy, n-pentyloxy, n-hexyloxy and 1,2-dimethylbutoxy.

"Halo" or "halogen" means fluorine (F), chlorine ($C_1$), bromine (Br) and iodine (I). In some embodiments, the halo group is F, —$C_1$ or Br. In some embodiments, the halogen group is F or $C_1$. In some embodiments, the halogen group is F.

Thus, "$C_{1-6}$ haloalkyl" and "$C_{1-6}$ haloalkoxy" refer to the above "$C_{1-6}$ alkyl" and "$C_{1-6}$ alkoxy", which are substituted by one or more halo groups. In some embodiments, $C_{1-4}$ haloalkyl group is particularly preferred, and more preferably $C_{1-2}$ haloalkyl group. In some embodiments, $C_{1-4}$ haloalkoxy group is particularly preferred, and more preferably $C_{1-2}$ haloalkoxy group. Exemplary haloalkyl groups include, but are not limited to, —$CF_3$, —$CH_2F$, —$CHF_2$, —$CHFCH_2F$, —$CH_2CHF_2$, —$CF_2CF_3$, —$CCl_3$, —$CH_2C_1$, —$CHCl_2$, 2,2,2-trifluoro-1,1-dimethyl-ethyl, and the like. Exemplary haloalkoxy groups include, but are not limited to: —$OCH_2F$, —$OCHF_2$, —$OCF_3$, and the like.

"$C_{3-10}$ cycloalkyl" refers to a radical of a non-aromatic cyclic hydrocarbon group having from 3 to 10 ring carbon atoms and zero heteroatoms. In some embodiments, $C_{3-7}$ cycloalkyl is preferred, $C_{3-6}$ cycloalkyl is particularly preferred, and $C_{5-6}$ cycloalkyl is more preferred. Cycloalkyl also includes ring systems wherein the cycloalkyl ring, as defined above, is fused with one or more aryl or heteroaryl groups wherein the point of attachment is on the cycloalkyl ring, and in such instances, the number of carbons continue to designate the number of carbons in the cycloalkyl ring system. Exemplary cycloalkyl groups include, but is not limited to, cyclopropyl ($C_3$), cyclopropenyl ($C_3$), cyclobutyl ($C_4$), cyclobutenyl ($C_4$), cyclopentyl ($C_5$), cyclopentenyl ($C_5$), cyclohexyl ($C_6$), cyclohexenyl ($C_6$), cyclohexadienyl ($C_6$), cycloheptyl ($C_7$), cycloheptenyl ($C_7$), cycloheptadienyl ($C_7$), cycloheptatrienyl ($C_7$), cyclooctyl ($C_8$), cyclooctenyl ($C_8$), bicyclo[2.2.1]heptanyl ($C_7$), bicyclo[2.2.2]octanyl ($C_8$), cyclononyl ($C_9$), cyclononenyl ($C_9$), cyclodecyl ($C_{10}$), cyclodecenyl ($C_{10}$), octahydro-1H-indenyl ($C_9$), decahydronaphthyl ($C_{10}$), spiro[4.5]decyl ($C_{10}$) and the like. Regardless of whether the cycloalkyl group is modified with "substituted", each instance of a cycloalkyl group is independently optionally substituted, e.g., for instance with from 1 to 5 substituents, 1 to 3 substituents, or 1 substituent. Appropriate substituents are defined below.

"3- to 10-membered heterocyclyl" refers to a radical of a 3- to 10-membered non-aromatic ring system having ring carbon atoms and 1 to 4 ring heteroatoms, wherein each heteroatom is independently selected from nitrogen, oxygen, sulfur, boron, phosphorus, and silicon. In heterocyclyl groups that contain one or more nitrogen atoms, the point of attachment may be a carbon or nitrogen atom, as valency permits. In some embodiments, 3- to 7-membered heterocyclyl is preferred, which is a radical of a 3- to 7-membered non-aromatic ring system having ring carbon atoms and 1 to 3 ring heteroatoms; in some embodiments, 3- to 6-membered heterocyclyl is particularly preferred, which is a radical of a 3- to 6-membered non-aromatic ring system having ring carbon atoms and 1 to 3 ring heteroatoms; 5- to 6-membered heterocyclyl is more preferred, which is a radical of a 5- to 6-membered non-aromatic ring system having ring carbon atoms and 1 to 3 ring heteroatoms. Heterocyclyl also includes ring systems wherein the heterocyclyl ring, as defined above, is fused with one or more aryl or heteroaryl groups, wherein the point of attachment is on the heterocyclyl ring; and in such instances, the number of ring members continue to designate the number of ring members in the heterocyclyl ring system. Regardless of whether the heterocyclyl group is modified with "substituted", each instance of an heterocyclyl group is independently optionally substituted, e.g., for instance with from 1 to 5 substituents, 1 to 3 substituents, or 1 substituent. Appropriate substituents are defined below.

Exemplary 3-membered heterocyclyl groups containing one heteroatom include, but are not limited to, azirdinyl, oxiranyl, thiorenyl. Exemplary 4-membered heterocyclyl groups containing one heteroatom include, but are not limited to, azetidinyl, oxetanyl and thietanyl. Exemplary 5-membered heterocyclyl groups containing one heteroatom include, but are not limited to, tetrahydrofuranyl, dihydrofuranyl, tetrahydrothiophenyl, dihydrothiophenyl, pyrrolidinyl, dihydropyrrolyl and pyrrolyl-2,5-dione. Exemplary 5-membered heterocyclyl groups containing two heteroatoms include, but are not limited to, dioxolanyl, oxasulfuranyl, disulfuranyl and oxazolidin-2-one. Exemplary 5-membered heterocyclyl groups containing three heteroatoms include, but are not limited to, triazolinyl, oxadiazolinyl, and thiadiazolinyl. Exemplary 6-membered heterocyclyl groups containing one heteroatom include, but are not limited to, piperidinyl, tetrahydropyranyl, dihydropyridinyl and thianyl. Exemplary 6-membered heterocyclyl groups containing two heteroatoms include, but are not limited to, piperazinyl, morpholinyl, dithianyl, dioxanyl. Exemplary 6-membered heterocyclyl groups containing three heteroatoms include, but are not limited to, triazinanyl. Exemplary 7-membered heterocyclyl groups containing one heteroatom include, but are not limited to, azepanyl, oxepanyl and thiepanyl. Exemplary 8-membered heterocyclyl groups containing one heteroatom include, but are not limited to, azocanyl, oxecanyl and thiocanyl. Exemplary 5-membered heterocyclyl groups fused to a $C_6$ aryl ring (also referred to herein as a 5,6-bicyclic heterocyclic ring) include, but are not limited to, indolinyl, isoindolinyl, dihydrobenzofuranyl, dihydrobenzothienyl, benzoxazolinonyl, and the like. Exemplary 6-membered heterocyclyl groups fused to an $C_6$ aryl ring (also referred to herein as a 6,6-bicyclic heterocyclic ring) include, but are not limited to, tetrahydroquinolinyl, tetrahydroisoquinolinyl, and the like.

"$C_{6-14}$ aryl" refers to a radical of a monocyclic or polycyclic (e.g., bicyclic or tricyclic) 4n+2 aromatic ring system (e.g., having 6, 10, or 14 π electrons shared in a cyclic array) having 6-14 ring carbon atoms and zero heteroatoms. In some embodiments, an aryl group has six ring carbon atoms ("$C_6$ aryl"; e.g., phenyl). In some embodiments, an aryl group has ten ring carbon atoms ("$C_{10}$ aryl"; e.g., naphthyl such as 1-naphthyl and 2-naphthyl). In some embodiments, an aryl group has fourteen ring carbon atoms ("$C_{14}$ aryl"; e.g., anthracyl). In some embodiments, $C_{6-10}$ aryl is particularly preferred, and $C_6$ aryl is more preferred. Aryl also includes ring systems wherein the aryl ring, as defined above, is fused with one or more cycloalkyl or heterocyclyl groups and the radical or point of attachment is on the aryl ring, and in such instances, the number of carbon atoms continue to designate the number of carbon atoms in the aryl ring system. Regardless of whether the aryl group is modified with "substituted", each instance of an aryl group is independently optionally substituted, e.g., for instance with from 1 to 5 substituents, 1 to 3 substituents, or 1 substituent. Appropriate substituents are defined below.

"5- to 10-membered heteroaryl" refers to a radical of a 5-10 membered monocyclic or bicyclic 4n+2 aromatic ring system (e.g., having 6 or 10 π electrons shared in a cyclic array) having ring carbon atoms and 1-4 ring heteroatoms, wherein each heteroatom is independently selected from nitrogen, oxygen and sulfur. In heteroaryl groups that contain one or more nitrogen atoms, the point of attachment may be a carbon or nitrogen atom, as valency permits. Heteroaryl bicyclic ring systems can include one or more heteroatoms in one or both rings. Heteroaryl includes ring systems wherein the heteroaryl ring, as defined above, is fused with one or more cycloalkyl or heterocyclyl groups wherein the point of attachment is on the heteroaryl ring, and in such instances, the number of ring members continue to designate the number of ring members in the heteroaryl ring system. In some embodiments, 5- to 6-membered heteroaryl group is particularly preferred, which is a 5-6 membered monocyclic or bicyclic 4n+2 aromatic ring system having ring carbon atoms and 1-4 ring heteroatoms. Regardless of whether the heteroaryl group is modified with "substituted", each instance of a heteroaryl group is independently optionally substituted, e.g., for instance with from 1 to 5 substituents, 1 to 3 substituents, or 1 substituent. Appropriate substituents are defined below.

Exemplary 5-membered heteroaryl groups containing one heteroatom include, but are not limited to, pyrrolyl, furanyl and thiophenyl. Exemplary 5-membered heteroaryl groups containing two heteroatoms include, but are not limited to, imidazolyl, pyrazolyl, oxazolyl, isoxazolyl, thiazolyl, and isothiazolyl. Exemplary 5-membered heteroaryl groups containing three heteroatoms include, but are not limited to, triazolyl, oxadiazolyl, and thiadiazolyl. Exemplary 5-membered heteroaryl groups containing four heteroatoms include, but are not limited to, tetrazolyl. Exemplary 6-membered heteroaryl groups containing one heteroatom include, but are not limited to, pyridinyl. Exemplary 6-membered heteroaryl groups containing two heteroatoms include, but are not limited to, pyridazinyl, pyrimidinyl, and pyrazinyl. Exemplary 6-membered heteroaryl groups containing three or four heteroatoms include, but are not limited to, triazinyl and tetrazinyl, respectively. Exemplary 7-membered heteroaryl groups containing one heteroatom include, but are not limited to, azepinyl, oxepinyl, and thiepinyl. Exemplary 5,6-bicyclic heteroaryl groups include, but are not limited to, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include, but are not limited to, naphthyridinyl, pteridinyl, quinolinyl, isoquinolinyl, cinnolinyl, quinoxalinyl, phthalazinyl, and quinazolinyl.

Exemplary carbon atom substituents include, but are not limited to, halogen, —CN, —NO$_2$, —N$_3$, —SO$_2$H, —SO$_3$H, —OH, —OR$^{aa}$, —ON(R$^{bb}$)$_2$, —N(R$^{bb}$)$_2$, —N(R$^{bb}$)$_3$$^+$X$^-$, —N(OR$^{cc}$)R$^{bb}$, —SH, —SR$^{aa}$, —SSR$^{cc}$, —C(=O)R$^{aa}$, —CO$_2$H, —CHO, —C(OR$^{cc}$)$_2$, —CO$_2$R$^{aa}$, —OC(=O)R$^{aa}$, —OCO$_2$R$^{aa}$, —C(=O)N(R$^{bb}$)$_2$, —OC(=O)N(R$^{bb}$)$_2$, —NR$^{bb}$C(=O)R$^{aa}$, —NR$^{bb}$CO$_2$R$^{aa}$, —NR$^{bb}$C(=O)N(R$^{bb}$)$_2$, —C(=NR$^{bb}$)R$^{aa}$, —C(=NR$^{bb}$)OR$^{aa}$, —OC(=NR$^{bb}$)R$^{aa}$, —OC(=NR$^{bb}$)OR$^{aa}$, —C(=NR$^{bb}$)N(R$^{bb}$)$_2$, —OC(=NR$^{bb}$)N(R$^{bb}$)$_2$, —NR$^{bb}$C(=NR$^{bb}$)N(R$^{bb}$)$_2$, —C(=O)NR$^{bb}$SO$_2$R$^{aa}$, —NR$^{bb}$SO$_2$R$^{aa}$, —SO$_2$N(R$^{bb}$)$_2$, -SO$_2$R$^{aa}$, —SO$_2$OR$^{aa}$, —OSO$_2$R$^{aa}$, —S(=O)R$^{aa}$, —OS(=O)R$^{aa}$, —Si(R$^{aa}$)$_3$, —OSi(R$^{aa}$)$_3$, —C(=S)N(R$^{bb}$)$_2$, —C(=O)SR$^{aa}$, —C(=S)SR$^{aa}$, —SC(=S)SR$^{aa}$, —SC(=O)SR$^{aa}$, —OC(=O)SR$^{aa}$, —SC(=O)OR$^{aa}$, —SC(=O)R$^{aa}$, —P(=O)$_2$R$^{aa}$, —OP(=O)$_2$R$^{aa}$, —P(=O)(R$^{aa}$)$_2$, —OP(=O)(R$^{aa}$)$_2$, —OP(=O)(OR$^{cc}$)$_2$, —P(=O)$_2$N(R$^{bb}$)$_2$, —OP(=O)$_2$N(R$^{bb}$)$_2$, —P(=O)(NR$^{bb}$)$_2$, —OP(=O)(NR$^{bb}$)$_2$, —NR$^{bb}$P(=O)(OR$^{cc}$)$_2$, —NR$^{bb}$P(=O)(NR$^{bb}$)$_2$, —P(R$^{cc}$)$_2$, —P(R$^{cc}$)$_3$, —OP(R$^{cc}$)$_2$, —OP(R$^{cc}$)$_3$, —B(R$^{aa}$)$_2$, —B(OR$^{cc}$)$_2$, —BR$^{aa}$(OR$^{cc}$), alkyl, perhaloalkyl, alkenyl, alkynyl, carbocyclyl, heterocyclyl, aryl, and heteroaryl, wherein each alkyl, alkenyl, alkynyl, carbocyclyl, heterocyclyl, aryl, and heteroaryl is independently substituted by 0, 1, 2, 3, 4, or 5 R$^{dd}$ groups;

or two geminal hydrogens on a carbon atom are replaced with the group =O, =S, =NN(R$^{bb}$)$_2$, =NNR$^{bb}$C(=O)R$^{aa}$, =NNR$^{bb}$C(=O)OR$^{aa}$, =NNR$^{bb}$S(=O)$_2$R$^{aa}$, =NR$^{bb}$, or =NOR$^{cc}$;

each instance of R$^{aa}$ is independently selected from alkyl, perhaloalkyl, alkenyl, alkynyl, carbocyclyl, heterocyclyl, aryl, and heteroaryl, or two R$^{aa}$ groups are joined to form a heterocyclyl or heteroaryl ring, wherein each alkyl, alkenyl, alkynyl, carbocyclyl, heterocyclyl, aryl, and heteroaryl is independently substituted by 0, 1, 2, 3, 4, or 5 R$^{dd}$ groups;

each instance of R$^{bb}$ is independently selected from hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR")OR$^{aa}$, —C(=NR")N(R$^{cc}$)$_2$, —SO$_2$N(R$^{cc}$)$_2$, —SO$_2$R", —SO$_2$OR$^{cc}$, —SOR$^{cc}$, —C(=S)N(R$^{cc}$)$_2$, —C(=O)SR$^{cc}$, —C(=S)SR$^{cc}$, —P(=O)$_2$R$^{aa}$, —P(=O)(R$^{aa}$)$_2$, —P(=O)$_2$N(R$^{cc}$)$_2$, —P(=O)(NR$^{cc}$)$_2$, alkyl, perhaloalkyl, alkenyl, alkynyl, carbocyclyl, heterocyclyl, aryl, and heteroaryl, or two R$^{bb}$ groups are joined to form a heterocyclyl or heteroaryl ring, wherein each alkyl, alkenyl, alkynyl, carbocyclyl, heterocyclyl, aryl, and heteroaryl is independently substituted by 0, 1, 2, 3, 4, or 5 R$^{dd}$ groups;

each instance of R$^{cc}$ is independently selected from hydrogen, alkyl, perhaloalkyl, alkenyl, alkynyl, carbocyclyl, heterocyclyl, aryl, and heteroaryl, or two R$^{cc}$ groups are joined to form a heterocyclyl or heteroaryl ring, wherein each alkyl, alkenyl, alkynyl, carbocyclyl, heterocyclyl, aryl, and heteroaryl is independently substituted by 0, 1, 2, 3, 4, or 5 R$^{dd}$ groups;

each instance of R$^{dd}$ is independently selected from halogen, —CN, —NO$_2$, —N$_3$, —SO$_2$H, —SO$_3$H, —OH, —OR', —ON(R$^{ff}$)$_2$, —N(R$^{ff}$)$_2$, —N(R$^{ff}$)$_3$$^+$X$^-$, —N(OR$^{ee}$)R$^{ff}$, —SH, —SR$^{ee}$, —SSR$^{ee}$, —C(=O)R$^{ee}$, —CO$_2$H, —CO$_2$R$^{ee}$, —OC(=O)R$^{ee}$, —OCO$_2$R$^{ee}$, —C(=O)N(R$^{ff}$)$_2$, —OC(=O)N(R$^{ff}$)$_2$, —NR$^{ff}$C(=O)R$^{ee}$, —N$^{ff}$CO$_2$R$^{ee}$, —NR$^{ff}$C(=O)N(R$^{ff}$)$_2$, —C(=NR$^{ff}$)OR', —OC(=NR$^{ff}$)R$^{ee}$, —OC(=NR$^{ff}$)OR$^{ee}$, —C(=NR$^{ff}$)N(R$^{ff}$)$_2$, —OC(=NR$^{ff}$)N(R$^{ff}$)$_2$, —NR$^{ff}$C(=NR$^{ff}$)N(R$^{ff}$)$_2$, —NR$^{ff}$SO$_2$R$^{ee}$, —SO$_2$N(R$^{ff}$)$_2$, —SO$_2$R$^{ee}$, —SO$_2$OR$^{ee}$, —OSO$_2$R$^{ee}$, —S(=O)R$^{ee}$, —Si(R$^{ee}$)$_3$, —OSi(R$^{ee}$)$_3$, —C(=S)N(R$^{ff}$)$_2$, —C(=O)SR$^{ee}$, —C(=S)SR$^{ee}$, —SC(=S)SR$^{ee}$, —P(=O)$_2$R$^{ee}$, —P(=O)(R$^{ee}$)$_2$, —OP(=O)(R$^{ee}$)$_2$, —OP(=O)(OR$^{ee}$)$_2$, alkyl, perhaloalkyl, alkenyl, alkynyl, carbocyclyl, heterocyclyl, aryl, heteroaryl, wherein each alkyl, alkenyl, alkynyl, carbocyclyl, heterocyclyl, aryl, and heteroaryl is independently substituted by 0, 1, 2, 3, 4, or 5 R$^{gg}$ groups, or two geminal R$^{dd}$ substituents may be joined to form =O or =S;

each instance of R$^{ee}$ is independently selected from alkyl, perhaloalkyl, alkenyl, alkynyl, carbocyclyl, aryl, heterocyclyl, and heteroaryl, wherein each alkyl, alkenyl, alkynyl, carbocyclyl, heterocyclyl, aryl, and heteroaryl is independently substituted by 0, 1, 2, 3, 4, or 5 R$^{gg}$ groups;

each instance of R$^{ff}$ is independently selected from hydrogen, alkyl, perhaloalkyl, alkenyl, alkynyl, carbocyclyl, heterocyclyl, aryl and heteroaryl, or two R$^{ff}$ groups are joined to form a heterocyclyl or heteroaryl ring, wherein each alkyl, alkenyl, alkynyl, carbocyclyl, heterocyclyl, aryl, and heteroaryl is independently substituted by 0, 1, 2, 3, 4, or 5 R$^{gg}$ groups; and each instance of R$^{gg}$ is independently halogen, —CN, —NO$_2$, —N$_3$, —SO$_2$H, —SO$_3$H, —OH, —OC$_{1-6}$ alkyl, —ON(C$_{1-6}$ alkyl)$_2$, —N(C$_{1-6}$ alkyl)$_2$, —N(C$_{1-6}$ alkyl)$_3$$^+$X$^-$, —NH(C$_{1-6}$ alkyl)$_2$$^+$X$^-$, —NH$_2$(C$_{1-6}$ alkyl)$^+$X$^-$, —NH$_3$$^+$X$^-$, —N(OC$_{1-6}$ alkyl)(C$_{1-6}$ alkyl), —N(OH)(C$_{1-6}$ alkyl), —NH(OH), —SH, —SC$_{1-6}$ alkyl, —SS(C$_{1-6}$ alkyl), —C(=O)(C$_{1-6}$ alkyl), —CO$_2$H, —CO$_2$(C$_{1-6}$ alkyl), —OC(=O)(C$_{1-6}$ alkyl), —OCO$_2$(C$_{1-6}$ alkyl), —C(=O)NH$_2$, —C(=O)N(C$_{1-6}$ alkyl)$_2$, —OC(=O)NH(C$_{1-6}$ alkyl), —NHC(=O)(C$_{1-6}$ alkyl), —N(C$_{1-6}$ alkyl)C(=O)(C$_{1-6}$ alkyl), —NHCO$_2$(C$_{1-6}$ alkyl), —NHC(=O)N(C$_{1-6}$ alkyl)$_2$, —NHC(=O)NH(C$_{1-6}$ alkyl), —NHC(=O)NH$_2$, —C(=NH)(C$_{1-6}$ alkyl), —OC(=NH)(C$_{1-6}$ alkyl), —OC(=NH)OC$_{1-6}$ alkyl, —C(=NH)N(C$_{1-6}$ alkyl)$_2$, —C(=NH)NH(C$_{1-6}$ alkyl), —C(=NH)NH$_2$, —OC(=NH)N(C$_{1-6}$ alkyl)$_2$, —OC(NH)NH(C$_{1-6}$ alkyl), —OC(NH)NH$_2$, —NHC(NH)N(C$_{1-6}$ alkyl)$_2$, —NHC(=NH)NH$_2$, —NHSO$_2$(C$_{1-6}$ alkyl), —SO$_2$N(C$_{1-6}$ alkyl)$_2$, —SO$_2$NH(C$_{1-6}$ alkyl), —SO$_2$NH$_2$, —SO$_2$C$_{1-6}$ alkyl, —SO$_2$OC$_{1-6}$ alkyl, —OSO$_2$C$_{1-6}$ alkyl, —SOC$_{1-6}$ alkyl, —Si(C$_{1-6}$ alkyl)$_3$, —OSi(C$_{1-6}$ alkyl)$_3$-C(=S)N(C$_{1-6}$ alkyl)$_2$, C(=S)NH(C$_{1-6}$ alkyl), C(=S)NH$_2$, —C(=O)S(C$_{1-6}$ alkyl), —C(=S)SC$_{1-6}$ alkyl, —SC(=S)SC$_{1-6}$ alkyl, —P(=O)$_2$(C$_{1-6}$ alkyl), —P(=O)(C$_{1-6}$ alkyl)$_2$, —OP(=O)(C$_{1-6}$ alkyl)$_2$, —OP(=O)(OC$_{1-6}$ alkyl)$_2$, C$_{1-6}$ alkyl, C$_{1-6}$ haloalkyl, C$_2$-C$_6$ alkenyl, C$_2$-C$_6$ alkynyl, C$_3$-C$_7$ carbocyclyl, C$_6$-C$_{10}$ aryl, C$_3$-C$_7$ heterocyclyl, C$_5$-C$_{10}$ heteroaryl; or two geminal R$^{gg}$ substituents may be joined to form =O or =S; wherein X$^-$ is a counterion.

Exemplary nitrogen atom substituents include, but are not limited to, hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{bb}$)R$^{aa}$, —C(=NR")OR$^{aa}$, —C(=NR")N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)$_2$R$^{aa}$, —P(=O)(R$^{aa}$)$_2$, —P(=O)$_2$N(R$^{cc}$)$_2$, —P(=O)(NR$^{cc}$)$_2$, alkyl, perhaloalkyl, alkenyl, alkynyl, carbocyclyl, heterocyclyl, aryl, and heteroaryl, or two R$^{cc}$ groups attached to a nitrogen atom are joined to form a heterocyclyl or heteroaryl ring, wherein each alkyl, alkenyl, alkynyl, carbocyclyl, heterocyclyl, aryl, and heteroaryl is independently substituted by 0, 1, 2, 3, 4, or 5 R$^{dd}$ groups, and wherein R$^{aa}$, R$^{bb}$, R$^{Cc}$ and R$^{dd}$ are as defined above.

The term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, Berge et al., describes pharmaceutically acceptable salts in detail in *J.*

Pharmaceutical Sciences (1977) 66: 1-19. Pharmaceutically acceptable salts of the compounds of the present disclosure include those derived from suitable inorganic and organic acids and inorganic and organic bases. Examples of pharmaceutically acceptable, nontoxic acid addition salts are salts formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid. Salts formed by using regular methods used in the art such as ion exchange are also included. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Pharmaceutically acceptable salts derived from appropriate bases include alkali metal, alkaline earth metal, ammonium and $N^+(C_{1-4}$ alkyl$)_4$ salts. Representative alkali or alkaline earth metal salts include sodium, lithium, potassium, calcium, magnesium, and the like. Other pharmaceutically acceptable salts include, when appropriate, nontoxic ammonium, quaternary ammonium, and amine cations formed with counterions such as halide, hydroxide, carboxylate, sulfate, phosphate, nitrate, lower alkyl sulfonate, and aryl sulfonate.

"Active metabolite" refers to the pharmacologically active product produced by the in vivo metabolization of the compound of formula (I) or salt thereof. The prodrugs and active metabolites of compounds can be determined using conventional techniques known or available in the art.

A "subject" to which administration is contemplated includes, but is not limited to, humans (i.e., a male or female of any age group, e.g., a pediatric subject (e.g., infant, child, adolescent) or adult subject (e.g., young adult, middle-aged adult or senior adult)) and/or a non-human animal, e.g., a mammal such as primates (e.g., cynomolgus monkeys, rhesus monkeys), cattle, pigs, horses, sheep, goats, rodents, cats, and/or dogs. In certain embodiments, the subject is a human. In certain embodiments, the subject is a non-human animal. The terms "human", "patient" and "subject" are used interchangeably herein.

Disease, disorder, and condition are used interchangeably herein.

As used herein, and unless otherwise specified, the terms "treat", "treating" and "treatment" contemplate an action that occurs while a subject is suffering from the specified disease, disorder or condition, which reduces the severity of the disease, disorder or condition, or retards or slows the progression of the disease, disorder or condition ("therapeutic treatment"), and also contemplates an action that occurs before a subject begins to suffer from the specified disease, disorder or condition ("prophylactic treatment").

"Combination" and related terms mean the simultaneous or sequential administration of a therapeutic agent of the present disclosure. For example, a compound disclosed herein may be administered simultaneously or sequentially with another therapeutic agent in separate unit dosage forms, or together with another therapeutic agent in a single unit dosage form.

Specific Embodiments

Compound

Herein, "the compound of the present disclosure" refers to the following compound of formula (I)-formula (III) (including the subsets of each formula, such as the compound of formula (II-a)), or pharmaceutically acceptable salts, enantiomers, diastereomers, racemates, solvates, hydrates, polymorphs, prodrugs or active metabolites thereof.

In one embodiment, the present disclosure relates to the compound of formula (I):

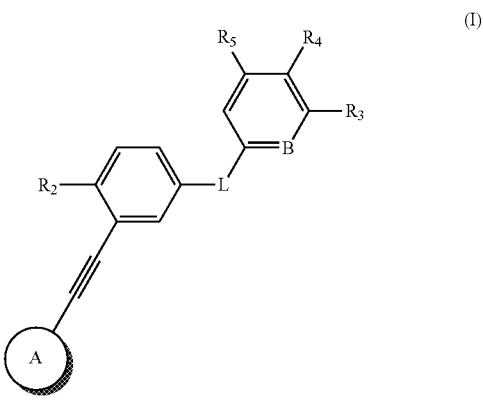

wherein, ring A is selected from ring A-1, A-2 and A-3 of the following structures:

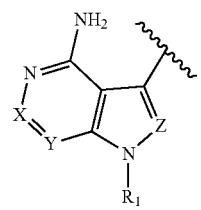

A-1

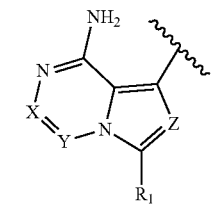

A-2

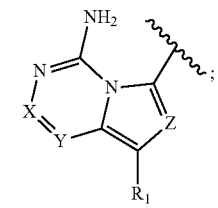

A-3

X, Y and Z are independently selected from CH or N; provided that ring A is not

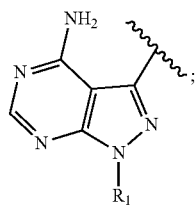

R₁ is selected from H, C₁₋₆ alkyl, C₃₋₇ cycloalkyl, 3- to 7-membered heterocyclyl, C₆₋₁₀ aryl or 5- to 10-membered heteroaryl; wherein the groups are optionally substituted by one or more R₁ₐ; provided that when A is A-1, R₁ is not H;

R₂ is selected from H, CN, NO₂, OH, halogen, C₁₋₆ alkyl, C₁₋₆ haloalkyl, C₁₋₆ alkoxy or C₁₋₆ haloalkoxy;

L is selected from —C(O)N(R₁ᵦ)—, —N(R₁ᵦ)C(O)— or —N(R₁ᵦ)C(O)N(R₁ᵦ)—;

B is selected from CH or N;

R₃ is selected from H, C₁₋₆ alkyl or C₁₋₆ haloalkyl;

R₄ and R₅ are selected from:

1) R₅ is H, R₄ is selected from H, C₁₋₆ alkyl, —CO₀₋₂ alkylene-C₃₋₇ cycloalkyl, —CO₀₋₂ alkylene-3- to 7-membered heterocyclyl or —CO₀₋₂ alkylene-NR₁꜀R₂꜀, wherein the groups are optionally substituted by one or more R₁d; or 2) R₄ is H, R₅ is selected from H or 5- to 6-membered heteroaryl containing one or more N, O or S heteroatoms, wherein the said 5- to 6-membered heteroaryl ring is optionally substituted by one or more R₁d;

each R₁ₐ is independently selected from H, halogen, oxo, —C₀₋₆ alkylene-ORₐ, —C₀₋₆ alkylene-NRᵦR꜀, —C₀₋₆ alkylene-C(O)Rₐ, —C₀₋₆ alkylene-C(O)ORₐ, —C₀₋₆ alkylene-C(O)NRᵦR꜀, C₁₋₆ alkyl, C₁₋₆ haloalkyl, —C₀₋₆ alkylene-C₃₋₆ cycloalkyl or —C₀₋₆ alkylene-3- to 7-membered heterocyclyl; or two or more R₁ₐ together with the atom to which they attached form a C₃₋₇ cycloalkyl or 3- to 7-membered heterocyclyl;

each R₁ᵦ is independently selected from H, —C₀₋₆ alkylene-ORₐ, —C₀₋₆ alkylene-NRᵦR꜀, —C₀₋₆ alkylene-C(O)Rₐ, —C₀₋₆ alkylene-C(O)ORₐ, —C₀₋₆ alkylene-C(O)NRᵦR꜀, C₁₋₆ alkyl, C₁₋₆ haloalkyl, —C₀₋₆ alkylene-C₃₋₆ cycloalkyl or —C₀₋₆ alkylene-3- to 7-membered heterocyclyl; or two or more R₁ᵦ together with the atom to which they attached form a C₃₋₇ cycloalkyl or 3- to 7-membered heterocyclyl;

R₁꜀ and R₂꜀ are each independently selected from H, halogen, —C₀₋₆ alkylene-CN, —C₀₋₆ alkylene-ORₐ, —CO₀₋₆ alkylene-SRₐ, —CO₀₋₆ alkylene-NRᵦR꜀, —CO₀₋₆ alkylene-C(O)Rₐ, —C₀₋₆ alkylene-C(O)ORₐ, —CO₀₋₆ alkylene-C(O)NRᵦR꜀, C₁₋₆ alkyl, C₁₋₆ haloalkyl, C₂₋₆ alkenyl, C₂₋₆ alkynyl, —CO₀₋₆ alkylene-C₃₋₆ cycloalkyl, —CO₀₋₆ alkylene-3- to 7-membered heterocyclyl, —C₀₋₆ alkylene-C₆₋₁₀ aryl or —CO₀₋₆ alkylene-5- to 10-membered heteroaryl; or, R₁꜀, R₂ together with the nitrogen atom to which they attached form a C₃₋₇ cycloalkyl or 3- to 7-membered heterocyclyl;

each R₁d is independently selected from H, halogen, —CO₀₋₆ alkylene-CN, —C₀₋₆ alkylene-ORₐ, —CO₀₋₆ alkylene-SRₐ, —CO₀₋₆ alkylene-NRᵦR꜀, —CO₀₋₆ alkylene-C(O)Rₐ, —C₀₋₆ alkylene-C(O)ORₐ, —C₀₋₆ alkylene-C(O)NRᵦR꜀, C₁₋₆ alkyl, C₁₋₆ haloalkyl, C₂₋₆ alkenyl, C₂₋₆ alkynyl, —CO₀₋₆ alkylene-C₃₋₆ cycloalkyl, —CO₀₋₆ alkylene-3- to 7-membered heterocyclyl, —C₀₋₆ alkylene-C₆₋₁₀ aryl or —CO₀₋₆ alkylene-5- to 10-membered heteroaryl; or two or more R₁d together with the atom to which they attached form a C₃₋₇ cycloalkyl or 3- to 7-membered heterocyclyl;

Rₐ, Rᵦ and R꜀ are independently selected from H, C₁₋₆ alkyl, C₁₋₆ haloalkyl, C₃₋₇ cycloalkyl, 3- to 7-membered heterocyclyl, C₆₋₁₀ aryl or 5- to 10-membered heteroaryl;

provided that, the above compounds do not comprise the following structure:

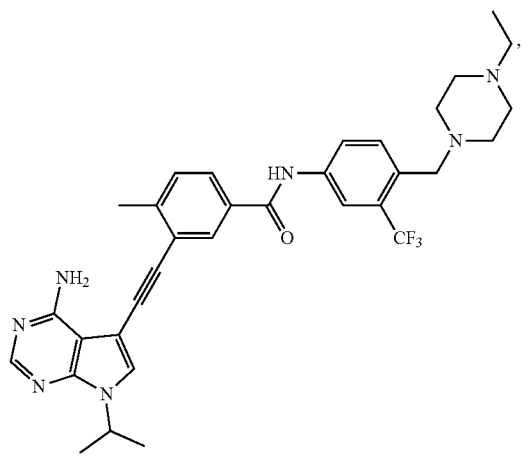

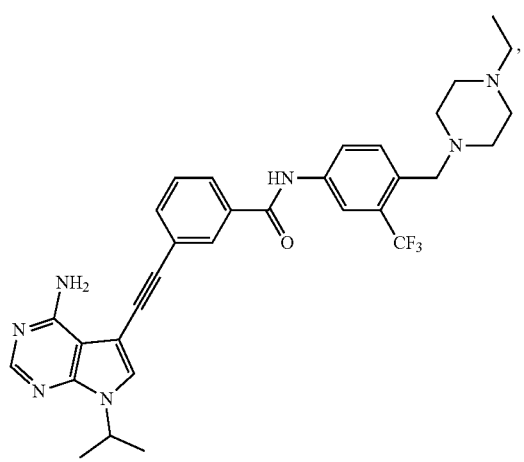

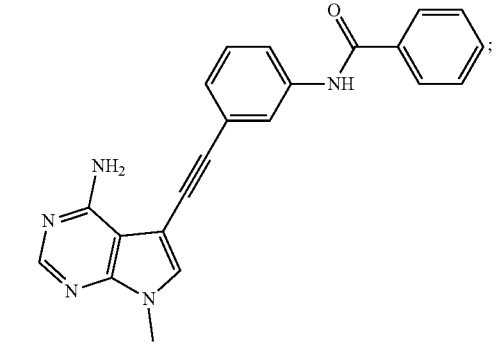

or the pharmaceutically acceptable salts, stereoisomers, solvates, hydrates, crystal forms, prodrugs or isotopic variants thereof.

In another embodiment, the present disclosure relates to the compound of formula (I):

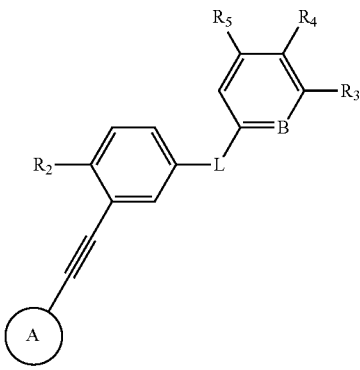

wherein,
ring A is selected from the following structure:

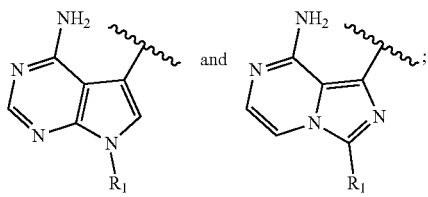

$R_1$ is selected from $C_{1-6}$ alkyl, $C_{3-7}$ cycloalkyl, 3- to 7-membered heterocyclyl, $C_{6-10}$ aryl or 5- to 10-membered heteroaryl, wherein the groups are optionally substituted by one or more $R_{1a}$;

$R_2$ is selected from H, CN, $NO_2$, OH, halogen, $C_{1-6}$ alkyl, $C_{1-6}$ haloalkyl, $C_{1-6}$ alkoxy or $C_{1-6}$ haloalkoxy;

L is selected from —C(O)N($R_{1b}$)—, —N($R_{1b}$)C(O)— or —N($R_{1b}$)C(O)N($R_{1b}$)—;

B is selected from CH or N;

$R_3$ is selected from $C_{1-6}$ alkyl or $C_{1-6}$ haloalkyl;

$R_4$ and $R_5$ are selected from:

1) $R_5$ is H, $R_4$ is selected from H, $C_{1-6}$ alkyl, —$CO_{0-2}$ alkylene-$C_{3-7}$ cycloalkyl, —$CO_{0-2}$ alkylene-3- to 7-membered heterocyclyl or —$CO_{0-2}$ alkylene-$NR_{1c}R_{2c}$, wherein the groups are optionally substituted by one or more $R_{1d}$; or, 2) $R_4$ is H, $R_5$ is selected from H or 5- to 6-membered heteroaryl containing one or more N, O or S heteroatoms, wherein the said 5- to 6-membered heteroaryl ring is optionally substituted by one or more $R_{1d}$;

each $R_{1a}$ is independently selected from H, halogen, oxo, —$C_{0-6}$ alkylene-$OR_a$, —$C_{0-6}$ alkylene-$NR_bR_c$, —$C_{0-6}$ alkylene-C(O)$R_a$, —$C_{0-6}$ alkylene-C(O)$OR_a$, —$C_{0-6}$ alkylene-C(O)$NR_bR_c$, $C_{1-6}$ alkyl, $C_{1-6}$ haloalkyl, —$C_{0-6}$ alkylene-$C_{3-6}$ cycloalkyl or —$C_{0-6}$ alkylene-3- to 7-membered heterocyclyl; or two or more $R_{1a}$ together with the atom to which they attached form a $C_{3-7}$ cycloalkyl or 3- to 7-membered heterocyclyl;

each $R_{1b}$ is independently selected from H, —$CO_{0-6}$ alkylene-$OR_a$, —$CO_{0-6}$ alkylene-$NR_bR_c$, —$CO_{0-6}$ alkylene-C(O)$R_a$, —$CO_{0-6}$ alkylene-C(O)$OR_a$, —$CO_{0-6}$ alkylene-C(O)$NR_bR_c$, $C_{1-6}$ alkyl, $C_{1-6}$ haloalkyl, —$CO_{0-6}$ alkylene-$C_{3-6}$ cycloalkyl or —$CO_{0-6}$ alkylene-3- to 7-membered heterocyclyl; or two or more $R_{1b}$ together with the atom to which they attached form a $C_{3-7}$ cycloalkyl or 3- to 7-membered heterocyclyl;

$R_{1c}$ and $R_2$ are each independently selected from H, halogen, —$C_{0-6}$ alkylene-CN, —$CO_{0-6}$ alkylene-$OR_a$, —$CO_{0-6}$ alkylene-$SR_a$, —$CO_{0-6}$ alkylene-$NR_bR_c$, —$CO_{0-6}$ alkylene-C(O)$R_a$, —$C_{0-6}$ alkylene-C(O)$OR_a$, —$CO_{0-6}$ alkylene-C(O)$NR_bR_c$, $C_{1-6}$ alkyl, $C_{1-6}$ haloalkyl, $C_{2-6}$ alkenyl, $C_{2-6}$ alkynyl, —$CO_{0-6}$ alkylene-$C_{3-6}$ cycloalkyl, —$CO_{0-6}$ alkylene-3- to 7-membered heterocyclyl, —$C_{0-6}$ alkylene-$C_{6-10}$ aryl or —$CO_{0-6}$ alkylene-5- to 10-membered heteroaryl; or, $R_{1c}$, $R_2$ together with the nitrogen atom to which they attached form a $C_{3-7}$ cycloalkyl or 3- to 7-membered heterocyclyl;

each $R_{1d}$ is independently selected from H, halogen, —$CO_{0-6}$ alkylene-CN, —$C_{0-6}$ alkylene-$OR_a$, —$CO_{0-6}$ alkylene-$SR_a$, —$CO_{0-6}$ alkylene-$NR_bR_c$, —$C_{0-6}$ alkylene-C(O)$R_a$, —$C_{0-6}$ alkylene-C(O)$OR_a$, —$CO_{0-6}$ alkylene-C(O)$NR_bR_c$, $C_{1-6}$ alkyl, $C_{1-6}$ haloalkyl, $C_{2-6}$ alkenyl, $C_{2-6}$ alkynyl, —$CO_{0-6}$ alkylene-$C_{3-6}$ cycloalkyl, —$CO_{0-6}$ alkylene-3- to 7-membered heterocyclyl, —$C_{0-6}$ alkylene-$C_{6-10}$ aryl or —$CO_{0-6}$ alkylene-5- to 10-membered heteroaryl; or two or more $R_{1d}$ together with the atom to which they attached form a $C_{3-7}$ cycloalkyl or 3- to 7-membered heterocyclyl;

$R_a$, $R_b$ and $R_c$ are independently selected from H, $C_{1-6}$ alkyl, $C_{1-6}$ haloalkyl, $C_{3-7}$ cycloalkyl, 3- to 7-membered heterocyclyl, $C_{6-10}$ aryl or 5- to 10-membered heteroaryl;

provided that, the above compounds do not comprise the following structures:

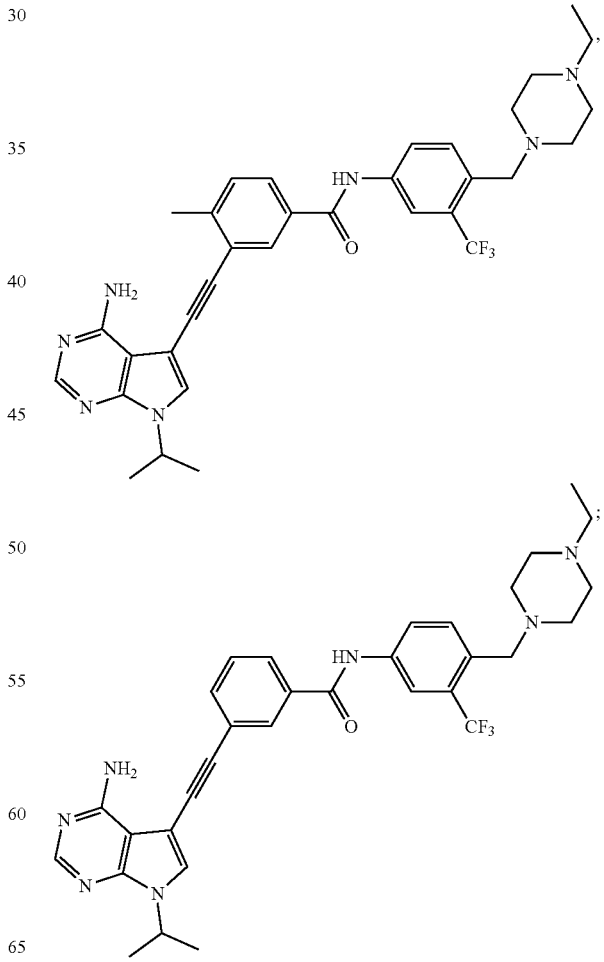

or the pharmaceutically acceptable salts, stereoisomers, solvates, hydrates, crystal forms, prodrugs or isotopic variants thereof.

In an embodiment of general formula (I), ring A is ring A-1 having the following structure:

A-1

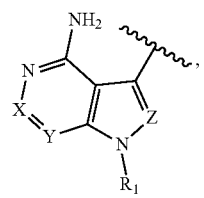

In a specific embodiment, X/Y/Z are independently CH; in another specific embodiment, X/Y/Z are independently N; in another specific embodiment, ring A is not

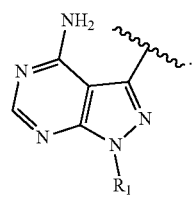

When ring A is represented by structure A-1, specific examples thereof include the following structures:

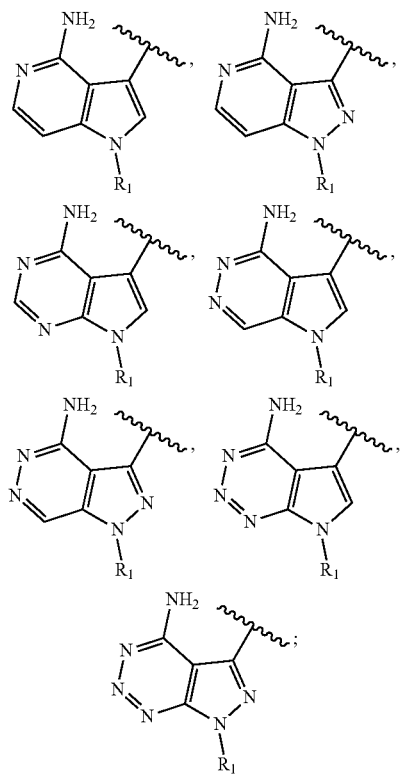

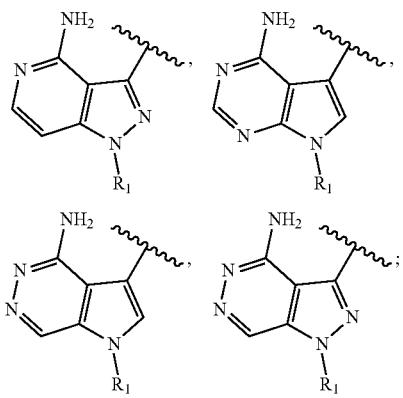

alternatively, ring A is selected from:

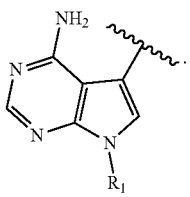

alternatively, ring A is:

In another embodiment, ring A is ring A-2 having the following structure:

A-2

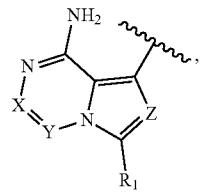

In a specific embodiment, X/Y/Z are independently CH; in another specific embodiment, X/Y/Z are independently N.

When ring A is represented by structure A-2, specific examples thereof include the following structures:

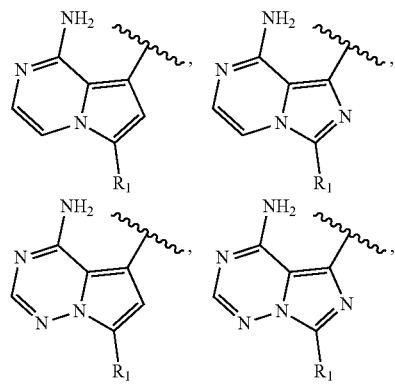

-continued

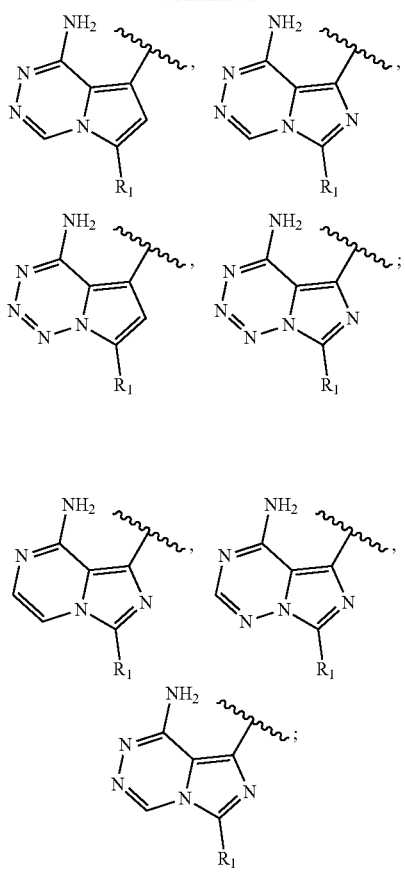

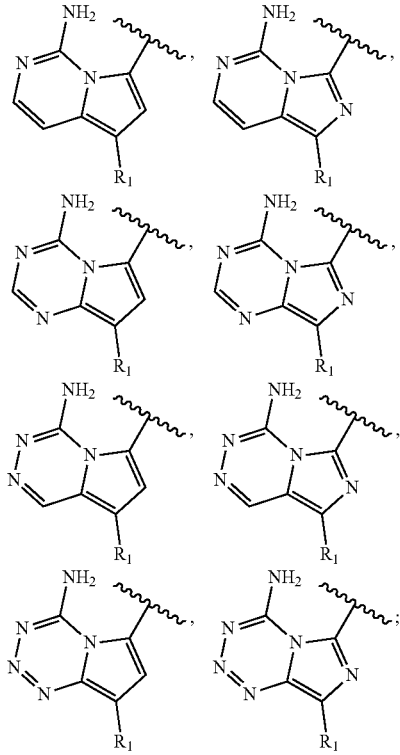

alternatively, ring A is selected from:

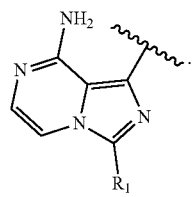

alternatively, ring A is:

In another embodiment, ring A is ring A-3 having the following structure:

A-3

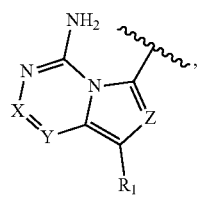

In a specific embodiment, X/Y/Z are independently CH; in another specific embodiment, X/Y/Z are independently N.

When ring A is represented by structure A-3, specific examples thereof include the following structures:

alternatively, ring A is selected from:

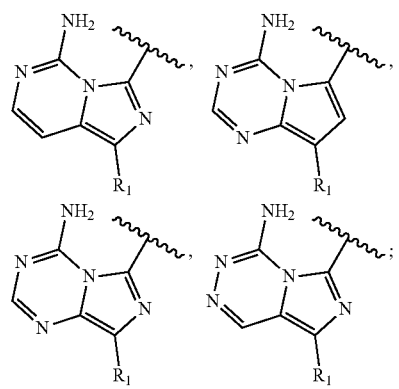

alternatively, ring A is:

In the above embodiments of A, $R_1$ is selected from H, $C_{1-6}$ alkyl, $C_{3-7}$ cycloalkyl, 3- to 7-membered heterocyclyl, $C_{6-10}$ aryl or 5- to 10-membered heteroaryl, wherein the groups are optionally substituted by one or more $R_{1a}$; alternatively, $R_1$ is selected from $C_{1-4}$ alkyl, $C_{4-6}$ cycloalkyl or 5- to 6-membered heterocyclyl, wherein the groups are optionally substituted by one or more $R_{1d}$; alternatively, $R_1$ is selected from methyl, ethyl, isopropyl, cyclopentyl, cyclohexyl, tetrahydrofuranyl, piperidinyl, piperazinyl or morpholinyl, wherein the groups are optionally substituted by one or more $R_{1a}$; alternatively, $R_1$ is selected from methyl, ethyl, isopropyl, cyclopentyl, cyclohexyl, tetrahydrofuranyl, piperidinyl, piperazinyl or morpholinyl, wherein the said groups are optionally substituted by one or more —OH; alternatively, $R_1$ is selected from methyl, ethyl, isopropyl, cyclopentyl or cyclohexyl, wherein the said groups are optionally substituted by one or more —OH.

In the above embodiments of $R_1$, each $R_{1a}$ is independently selected from H, halogen, oxo, —$C_{0-6}$ alkylene-$OR_a$, —$C_{0-6}$ alkylene-$NR_bR_c$, —$C_{0-6}$ alkylene-$C(O)R_a$, —$C_{0-6}$ alkylene-$C(O)OR_a$, —$C_{0-6}$ alkylene-$C(O)NR_bR_c$, $C_{1-6}$ alkyl, $C_{1-6}$ haloalkyl, —$C_{0-6}$ alkylene-$C_{3-6}$ cycloalkyl, —$C_{0-6}$ alkylene-3- to 7-membered heterocyclyl, or two or more $R_{1a}$ together with the atom to which they attached form a $C_{3-7}$ cycloalkyl or 3- to 7-membered heterocyclyl, wherein, the said $R_a$, $R_b$ and $R_c$ are each independently selected from H, $C_{1-6}$ alkyl, $C_{1-6}$ haloalkyl, $C_{3-7}$ cycloalkyl, 3- to 7-membered heterocyclyl, $C_{6-10}$ aryl or 5- to 10-membered heteroaryl; alternatively, each $R_{1a}$ is independently selected from H, halogen, $C_{1-6}$ alkyl or —OH; alternatively, each $R_{1a}$ is independently selected from H, $C_{1-6}$ alkyl or —OH.

In the above embodiments of general formula (I), $R_2$ is selected from H, CN, $NO_2$, OH, halogen, $C_{1-6}$ alkyl, $C_{1-6}$ haloalkyl, $C_{1-6}$ alkoxy or $C_{1-6}$ haloalkoxy; alternatively, $R_2$ is selected from H or $C_{1-4}$ alkyl; alternatively, $R_2$ is selected from H, methyl, ethyl or isopropyl; alternatively, $R_2$ is selected from H or methyl.

In an embodiment of general formula (I), L is selected from —$C(O)N(R_{1b})$—, —$N(R_{1b})C(O)$— or —$N(R_{1b})C(O)N(R_{1b})$—; alternatively, L is selected from —$C(O)N(R_{1b})$— or —$N(R_{1b})C(O)$—.

In the above embodiments of L, each $R_{1b}$ is independently selected from H, —$C_{0-6}$ alkylene-$OR_a$, —$C_{0-6}$ alkylene-$NR_bR_c$, —$C_{0-6}$ alkylene-$C(O)R_a$, —$C_{0-6}$ alkylene-$C(O)OR_a$, —$C_{0-6}$ alkylene-$C(O)NR_bR_c$, $C_{1-6}$ alkyl, $C_{1-6}$ haloalkyl, —$C_{0-6}$ alkylene-$C_{3-6}$ cycloalkyl or —$C_{0-6}$ alkylene-3- to 7-membered heterocyclyl, or two or more $R_{1b}$ together with the atom to which they attached form a $C_{3-7}$ cycloalkyl or 3- to 7-membered heterocyclyl; alternatively, each Rib is independently selected from H, —$C_{0-6}$ alkylene-$NR_bR_c$, $C_{1-6}$ alkyl, $C_{1-6}$ haloalkyl, —$C_{0-6}$ alkylene-$C_{3-6}$ cycloalkyl or —$C_{0-6}$ alkylene-3- to 7-membered heterocyclyl; alternatively, each $R_{1b}$ is independently selected from H, $C_{1-4}$ alkyl, —$C_{0-6}$ alkylene-$C_{3-6}$ cycloalkyl or —$C_{0-6}$ alkylene-3- to 7-membered heterocyclyl; alternatively, each $R_{1b}$ is independently selected from H or $C_{1-4}$ alkyl; alternatively, each $R_{1b}$ is independently selected from H, methyl, ethyl, isopropyl, cyclopropyl, cyclobutyl, cyclopentyl, cyclohexyl, tetrahydrofuranyl, tetrahydropyrrolyl, piperidinyl, piperazinyl or morpholinyl; alternatively, each $R_{1b}$ is H; wherein, the said $R_a$, $R_b$ and $R_c$ are independently selected from H, $C_{1-6}$ alkyl, $C_{1-6}$ haloalkyl, $C_{3-7}$ cycloalkyl, 3- to 7-membered heterocyclyl, $C_6$_10 aryl or 5- to 10-membered heteroaryl.

In an embodiment of general formula (I), B is selected from CH or N; alternatively, B is CH.

In an embodiment of general formula (I), $R_3$ is selected from H, $C_{1-6}$ alkyl or $C_{1-6}$ haloalkyl; alternatively, $R_3$ is selected from $C_{1-6}$ alkyl or $C_{1-6}$ haloalkyl; alternatively, $R_3$ is $C_1$-4 fluoroalkyl; alternatively, $R_3$ is selected from —$CF_2H$, —$CFH2$ or —$CF_3$; alternatively, $R_3$ is —$CF_3$.

In an embodiment of general formula (I), when $R_5$ is H, $R_4$ is selected from H, $C_{1-6}$ alkyl, —$CO_{0-2}$ alkylene-$C_{3-7}$ cycloalkyl, —$CO_{0-2}$ alkylene-3- to 7-membered heterocyclyl or —$CO_{0-2}$ alkylene-$NR_{1c}R_{2c}$, wherein the said groups are optionally substituted by one or more $R_{1d}$; alternatively, $R_4$ is selected from H, $C_{1-6}$ alkyl or —$CO_{0-2}$ alkylene-$NR_{1c}R_{2c}$, wherein the said groups are optionally substituted by one or more $R_{1d}$; alternatively, $R_4$ is selected from H, —$C_{1-4}$ alkyl or —$CH_2$—$NR_{1c}R_{2c}$, wherein the said groups are optionally substituted by one or more $R_{1d}$;

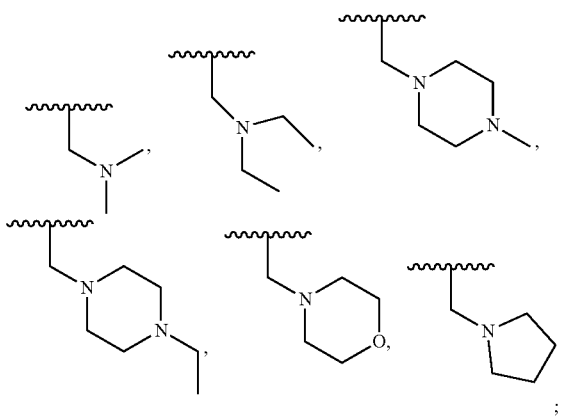

alternatively, $R_4$ is selected from H, methyl, ethyl, isopropyl, tert-butyl,

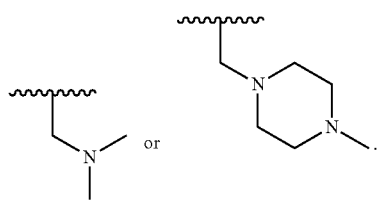

alternatively, $R_4$ is selected from H, methyl,

In the above embodiments of $R_4$ and $R_5$, $R_{1c}$ and $R_{2c}$ are each independently selected from H, halogen, —$C_{0-6}$ alkylene-CN, —$C_{0-6}$ alkylene-$OR_a$, —$C_{0-6}$ alkylene-$SR_a$, —$C_{0-6}$ alkylene-$NR_bR_c$, —$C_{0-6}$ alkylene-$C(O)R_a$, —$C_{0-6}$ alkylene-$C(O)OR_a$, —$C_{0-6}$ alkylene-$C(O)NR_bR_c$, $C_{1-6}$ alkyl, $C_{1-6}$ haloalkyl, $C_{2-6}$ alkenyl, $C_{2-6}$ alkynyl, —$CO_{0-6}$ alkylene-$C_{3-6}$ cycloalkyl, —$C_{0-6}$ alkylene-3- to 7-membered heterocyclyl, —$CO_{0-6}$ alkylene-$C_{6-10}$ aryl or —$CO_{0-6}$ alkylene-5- to 10-membered heteroaryl; or, $R_{1c}$, $R_{2c}$ together with the nitrogen atom to which they attached form a $C_{3-7}$ cycloalkyl or 3- to 7-membered heterocyclyl; wherein, $R_a$, $R_b$ and $R_c$ are independently selected from H, $C_{1-6}$ alkyl, $C_{1-6}$ haloalkyl, $C_{3-7}$ cycloalkyl, 3- to 7-membered heterocyclyl, $C_{6-10}$ aryl or 5- to 10-membered heteroaryl.

In an embodiment of general formula (I), when $R_4$ is H, $R_5$ is selected from H or 5- to 6-membered heteroaryl ring containing one or more N, O or S heteroatoms, wherein the said 5- to 6-membered heteroaryl ring is optionally substituted by one or more $R_{1d}$; alternatively, $R_5$ is selected from H or 5- to 6-membered heteroaryl ring containing one or more N heteroatoms, wherein the said 5- to 6-membered heteroaryl ring is optionally substituted by one or more $R_{1d}$; alternatively, $R_5$ is selected from H or 5-membered heteroaryl ring containing one or more N heteroatoms, wherein the said 5-membered heteroaryl ring is optionally substituted by one or more $R_{1d}$; alternatively, $R_5$ is selected from H or imidazolyl, wherein the said imidazolyl is optionally substituted by one or more $R_{1d}$.

In the above embodiments of $R_4$ and $R_5$, each $R_{1d}$ is independently selected from H, halogen, —$C_{0-6}$ alkylene-CN, —$C_{0-6}$ alkylene-$OR_a$, —$C_{0-6}$ alkylene-$SR_a$, —$C_{0-6}$ alkylene-$NR_bR_c$, —$C_{0-6}$ alkylene-$C(O)R_a$, —$C_{0-6}$ alkylene-$C(O)OR_a$, —$C_{0-6}$ alkylene-$C(O)NR_bR_c$, $C_{1-6}$ alkyl, $C_{1-6}$ haloalkyl, $C_{2-6}$ alkenyl, $C_{2-6}$ alkynyl, —$CO_{0-6}$ alkylene-$C_{3-6}$ cycloalkyl, —$CO_{0-6}$ alkylene-3- to 7-membered heterocyclyl, —$CO_{0-6}$ alkylene-$C_{6-10}$ aryl or —$CO_{0-6}$ alkylene-5- to 10-membered heteroaryl, or two or more $R_{1d}$ together with the atom to which they attached form a $C_{3-7}$ cycloalkyl or 3- to 7-membered heterocyclyl; wherein, $R_a$, $R_b$ and $R_c$ are independently selected from H, $C_{1-6}$ alkyl, $C_{1-6}$ haloalkyl, $C_{3-7}$ cycloalkyl, 3- to 7-membered heterocyclyl, $C_{6-10}$ aryl or 5- to 10-membered heteroaryl.

In another specific embodiment, the present disclosure provides compounds of formula (II-a) and formula (II-b):

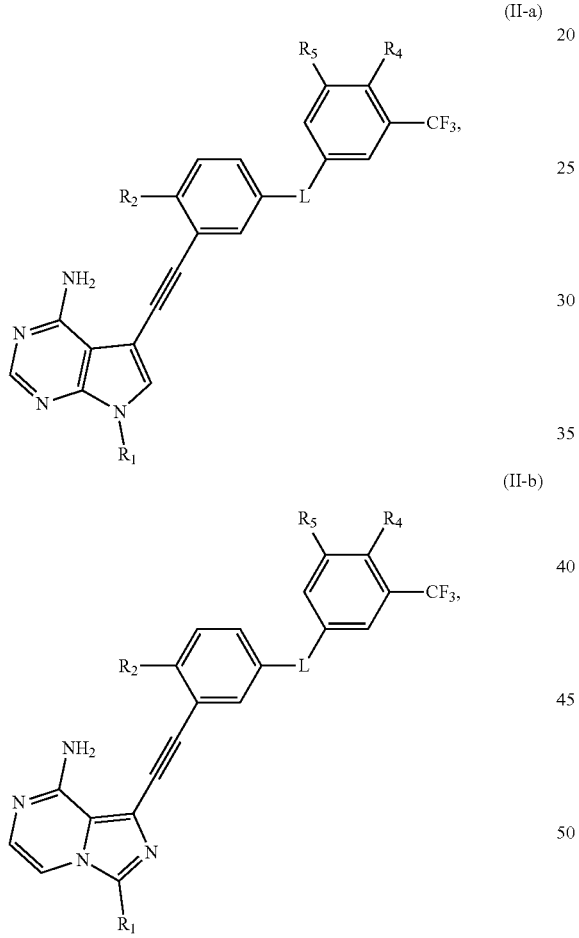

wherein, $R_1$ is selected from $C_{1-4}$ alkyl, $C_{4-6}$ cycloalkyl or 5- to 6-membered heterocyclyl, wherein the groups are optionally substituted by one or more $R_{1a}$;

$R_2$ is selected from H or $C_{1-4}$ alkyl;

L is selected from —C(O)NH—, —NHC(O)— or —NHC(O)NH—;

$R_4$ and $R_5$ are selected from:
1) $R_5$ is hydrogen, $R_4$ is selected from H, $C_{1-4}$ alkyl or —$CH_2$—$NR_{1c}R_{2c}$; wherein, $R_{1c}$ and $R_{2c}$ are each independently selected from $C_{1-6}$ alkyl, $C_{3-6}$ cycloalkyl or 3- to 7-membered heterocyclyl, or, $R_{1c}$, $R_{2c}$ together with the nitrogen atom to which they attached form a $C_{3-7}$ cycloalkyl or 5- to 6-membered heterocyclyl;
2) $R_4$ is hydrogen, $R_5$ is selected from H or 5- to 6-membered heteroaryl ring containing one or more N heteroatoms, wherein the said 5- to 6-membered heteroaryl ring can be optionally substituted by one or more $R_{1d}$;

$R_{1a}$ and $R_{1d}$ are as defined above.

In another specific embodiment, the present disclosure provides compounds of formula (II-a) and formula (II-b):

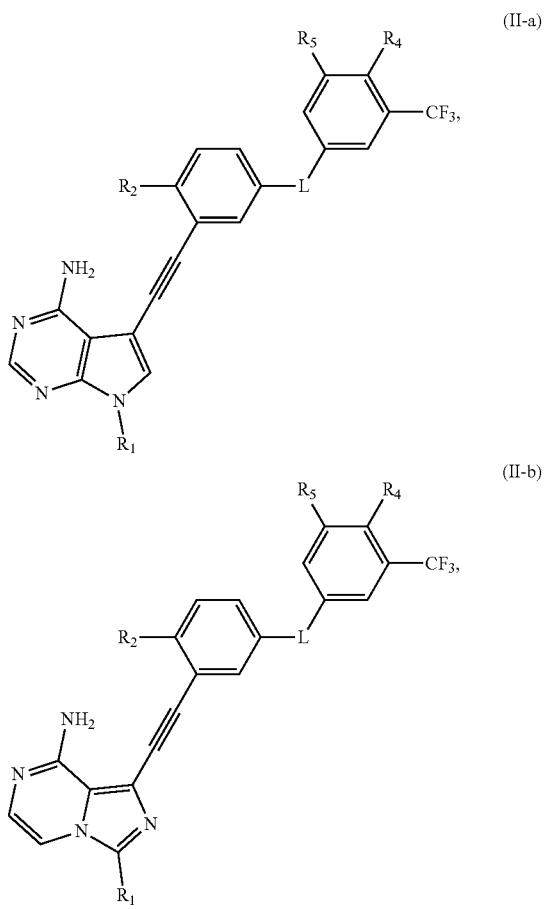

wherein, $R_1$ is selected from methyl, ethyl, isopropyl, cyclopentyl or cyclohexyl, wherein the said groups are optionally substituted by one or more —OH;

$R_2$ is selected from H or methyl;

L is selected from —C(O)NH— or —NHC(O);

$R_4$ and $R_5$ are selected from:
1) $R_5$ is hydrogen, $R_4$ is selected from H, methyl,

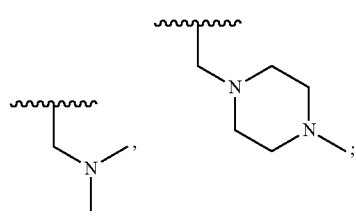

2) $R_4$ is hydrogen, $R_5$ is H or imidazolyl.

In another specific embodiment, the present disclosure provides a compound of formula (III-a):

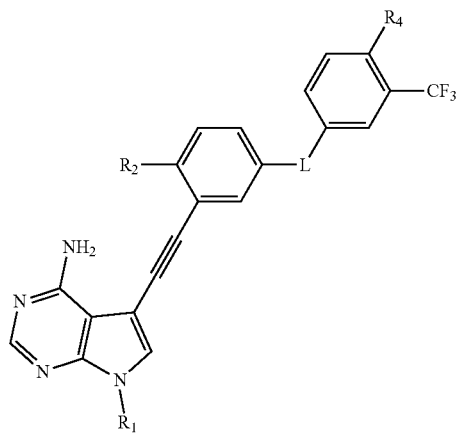

(III-a)

wherein, $R_1$ is selected from $C_{1-4}$ alkyl or $C_{4-6}$ cycloalkyl, wherein the said groups are optionally substituted by one or more —OH;

$R_2$ is selected from H or $C_{1-4}$ alkyl;

$R_4$ is selected from H or $C_{1-4}$ alkyl;

L is selected from —C(O)NH— or —NHC(O)—;

or the pharmaceutically acceptable salts, stereoisomers, solvates, hydrates, crystal forms, prodrugs or isotopic variants thereof.

In another specific embodiment, the present disclosure provides a compound of formula (III-b):

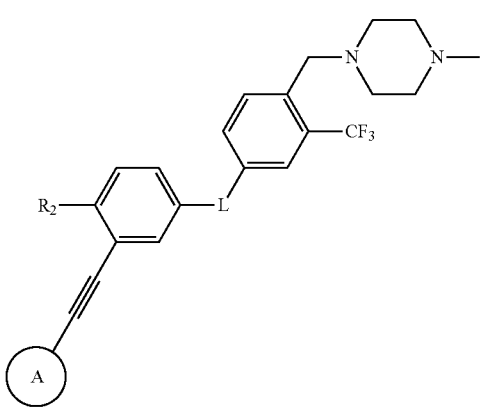

(III-b)

wherein, ring A is selected from the following structures:

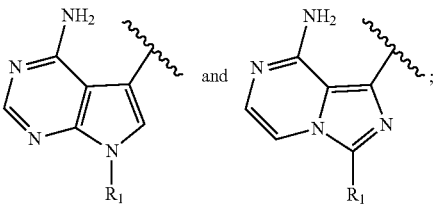

$R_1$ is selected from $C_{1-4}$ alkyl or $C_{4-6}$ cycloalkyl, wherein the said groups are optionally substituted by one or more —OH;

$R_2$ is selected from H or $C_{1-4}$ alkyl;

L is selected from —C(O)NH— or —NHC(O)—;

or the pharmaceutically acceptable salts, stereoisomers, solvates, hydrates, crystal forms, prodrugs or isotopic variants thereof.

In another specific embodiment, the present disclosure provides a compound of formula (III-c):

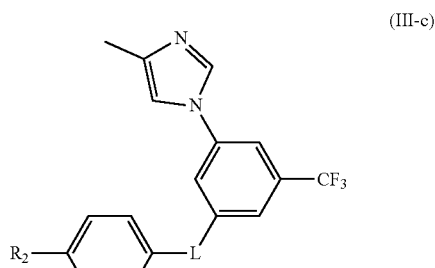

(III-c)

wherein, $R_1$ is selected from $C_{1-4}$ alkyl or $C_{4-6}$ cycloalkyl, wherein the group is optionally substituted by one or more —OH;

$R_2$ is selected from H or $C_{1-4}$ alkyl;

L is selected from —C(O)NH— or —NHC(O)—;

or the pharmaceutically acceptable salts, stereoisomers, solvates, hydrates, crystal forms, prodrugs or isotopic variants thereof.

In another specific embodiment, the present disclosure relates to the following compounds:
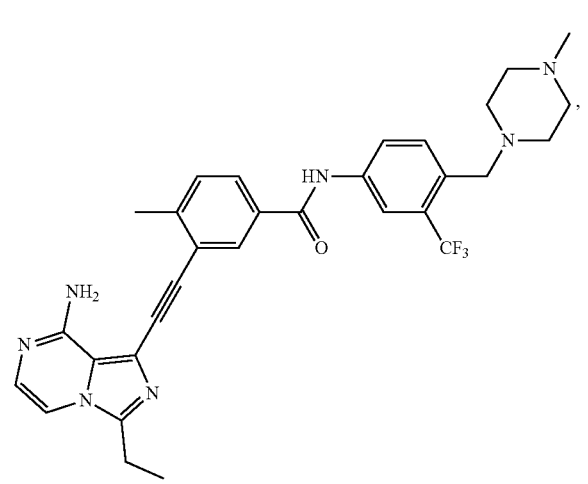
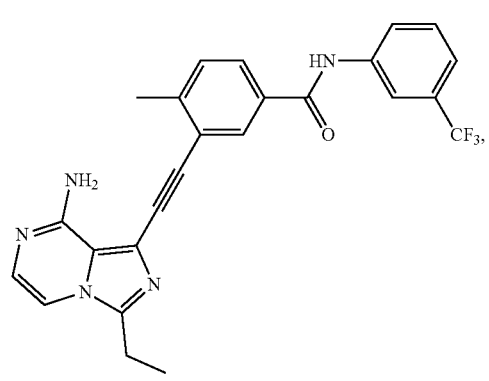
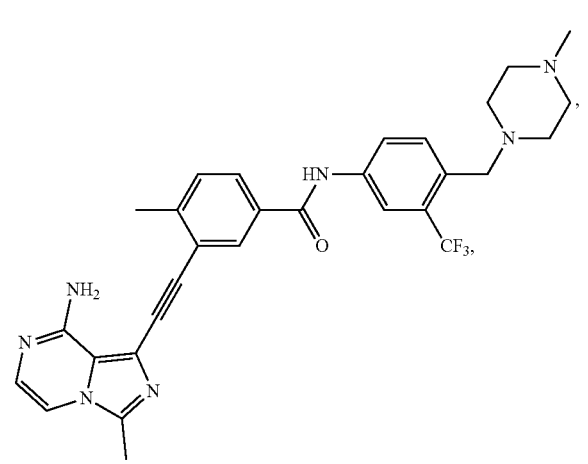
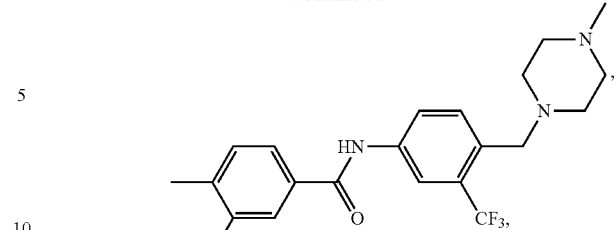
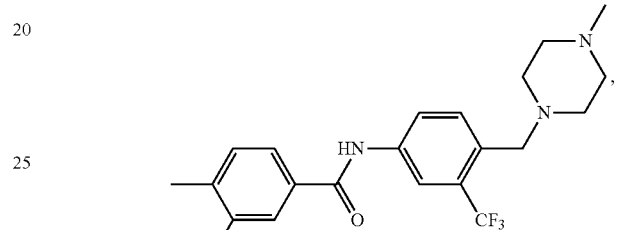
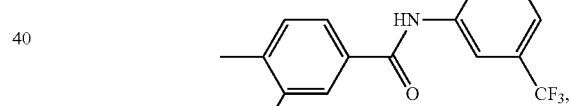
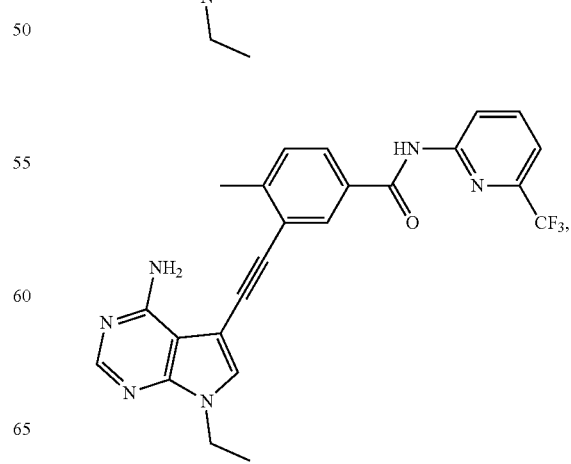

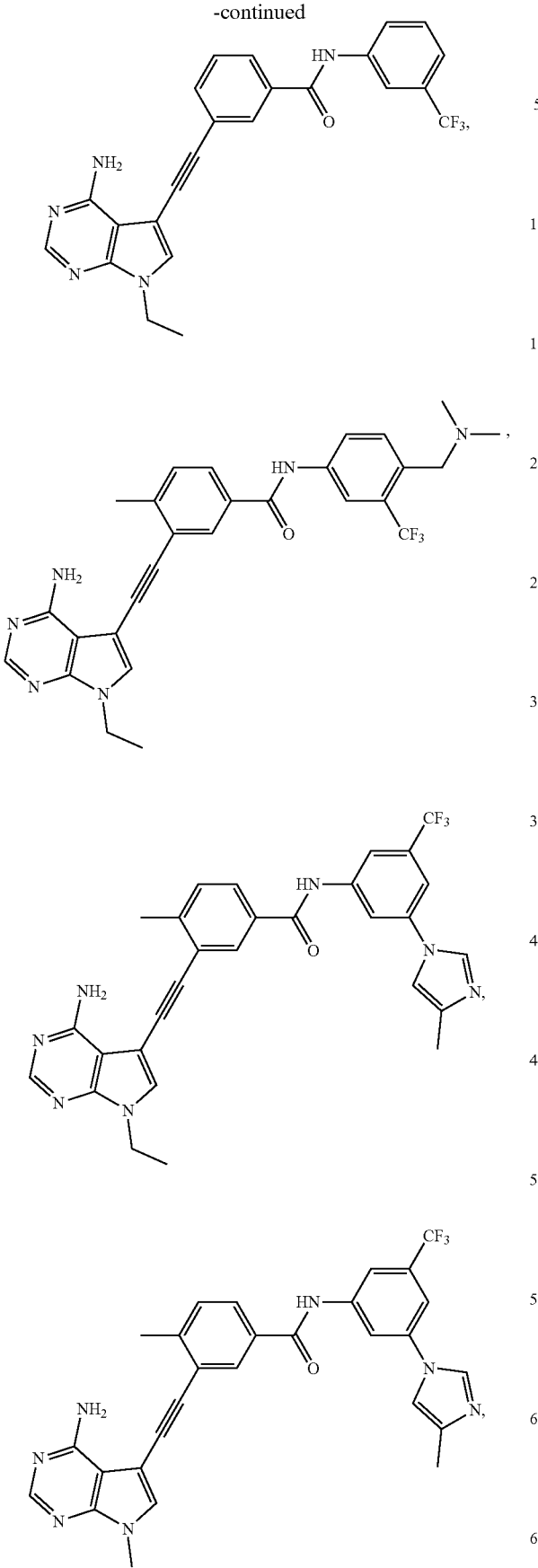
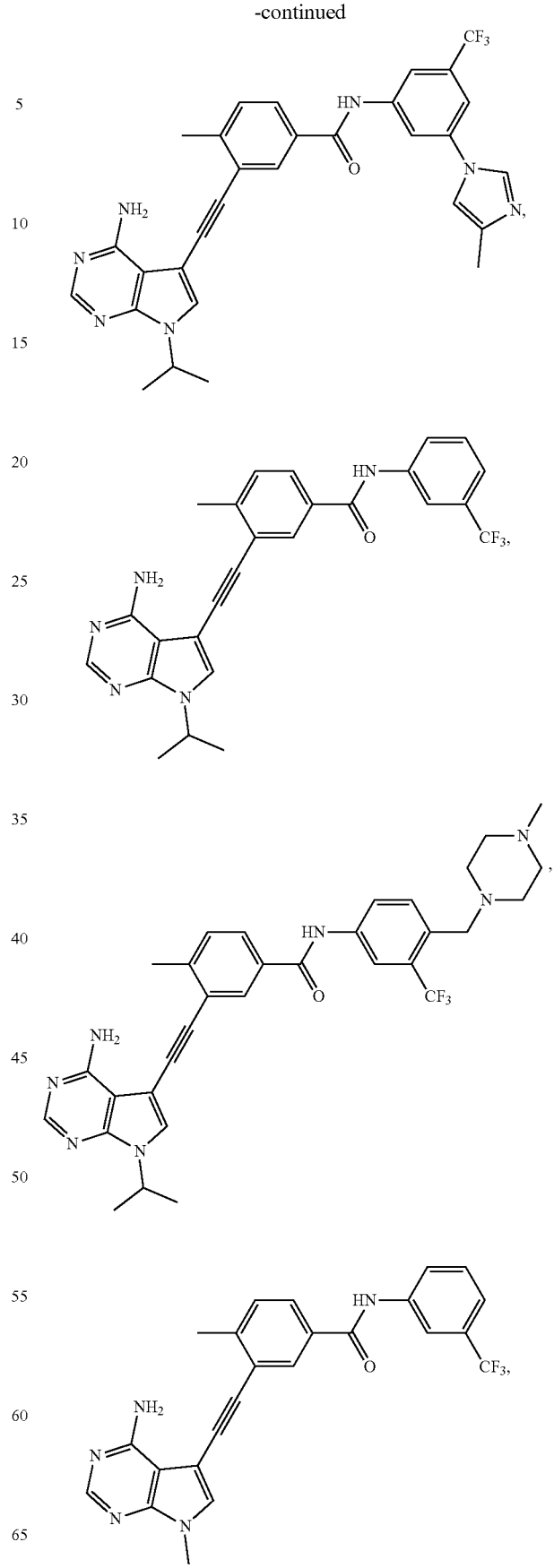

33
-continued
34
-continued
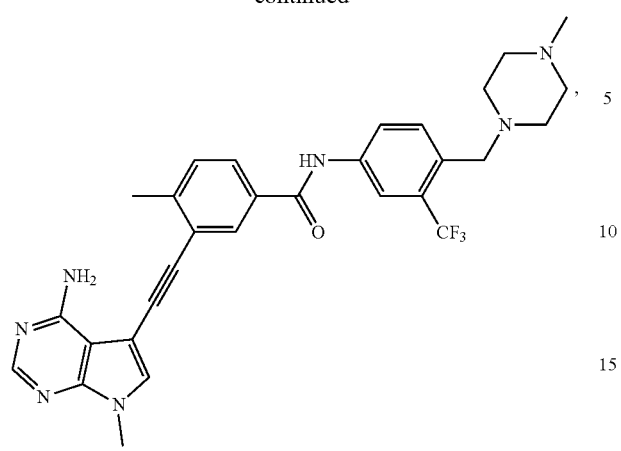
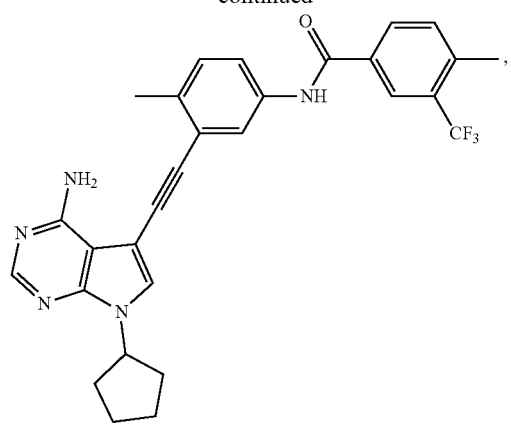

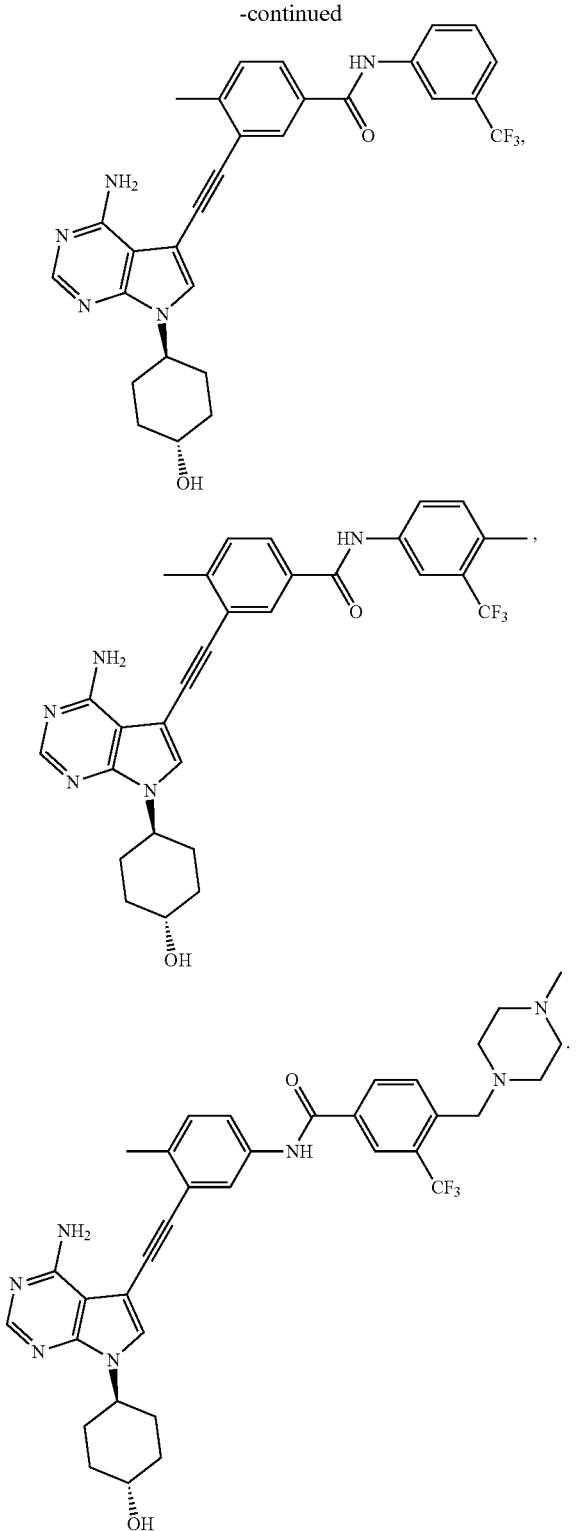

The compounds of the present disclosure may include one or more asymmetric centers, and thus may exist in a variety of stereoisomeric forms, for example, enantiomers and/or diastereomers. For example, the compounds of the present disclosure may be in the form of an individual enantiomer, diastereomer or geometric isomer (e.g., cis- and trans-isomers), or may be in the form of a mixture of stereoisomers, including racemic mixture and a mixture enriched in one or more stereoisomers. The isomers can be separated from the mixture by the methods known to those skilled in the art, including chiral high pressure liquid chromatography (HPLC) and the formation and crystallization of chiral salts; or preferred isomers can be prepared by asymmetric synthesis.

It will be understood by those skilled in the art that the organic compounds can form complexes with solvents in which they are reacted or from which they are precipitated or crystallized. These complexes are known as "solvates." Where the solvent is water, the complex is known as "hydrate." The present disclosure encompasses all solvates of the compounds of the present disclosure.

The term "solvate" refers to forms of a compound or a salt thereof, which are associated with a solvent, usually by a solvolysis reaction. This physical association may include hydrogen bonding. Conventional solvents include water, methanol, ethanol, acetic acid, DMSO, THF, diethyl ether, etc. The compounds described herein can be prepared, for example, in crystalline form, and can be solvated. Suitable solvates include pharmaceutically acceptable solvates and further include both stoichiometric solvates and non-stoichiometric solvates. In some cases, the solvates will be capable of isolation, for example, when one or more solvent molecules are incorporated into the crystal lattice of a crystalline solid. "Solvate" includes both solution-phase and isolatable solvates. Representative solvates include hydrates, ethanolates and methanolates.

The term "hydrate" refers to a compound that is associated with water. Generally, the number of water molecules contained in a hydrate of a compound is in a definite ratio to the number of the compound molecules in the hydrate. Therefore, hydrates of a compound can be represented, for example, by a general formula R·x $H_2O$, wherein R is the compound, and x is a number greater than 0. Given compounds can form more than one type of hydrates, including, for example, monohydrates (x is 1), lower hydrates (x is a number greater than 0 and smaller than 1, for example, hemihydrates (R·0.5 $H_2O$)) and polyhydrates (x is a number greater than 1, for example, dihydrates (R·2 $H_2O$) and hexahydrates (R·6 $H_2O$)).

Compounds of the present disclosure may be in an amorphous or a crystalline form (polymorph). Furthermore, the compounds of the present disclosure may exist in one or more crystalline forms. Therefore, the present disclosure includes all amorphous or crystalline forms of the compounds of the present disclosure within its scope. The term "polymorph" refers to a crystalline form of a compound (or a salt, hydrate or solvate thereof) in a particular crystal packing arrangement. All polymorphs have the same elemental composition. Different crystalline forms generally have different X-ray diffraction patterns, infrared spectra, melting points, density, hardness, crystal shapes, optical and electrical properties, stability, and solubility. Recrystallization solvents, rate of crystallization, storage temperatures, and other factors may cause one crystalline form to dominate. Various polymorphs of a compound can be prepared by crystallization under different conditions.

The present disclosure also comprises compounds that are labeled with isotopes, which are equivalent to those described in formula (I), but one or more atoms are replaced by atoms having an atom mass or mass number that are different from that of atoms that are common in nature. Examples of isotopes which may be introduced into the compounds of the disclosure include isotopes of hydrogen, carbon, nitrogen, oxygen, phosphorus, sulfur, fluorine and chlorine, such as $^2H$, $^3H$, $^{13}C$, $^{11}C$, $^{14}C$, $^{15}N$, $^{18}$, $^{17}O$, $^{31}P$, $^{32}P$, $^{35}$S, $^{18}$F and $^{36}$Cl, respectively. Compounds of the present disclosure that comprise the above isotopes and/or other isotopes of other atoms, prodrugs thereof and pharmaceutically acceptable salts of said compounds or prodrugs all are within the scope of the present disclosure. Certain isotope-labeled compounds of the present disclosure, such as those incorporating radioactive isotopes (e.g., $^{3}$H and $^{14}$C), can be used for the measurement of the distribution of drug and/or substrate in tissue. Tritium, which is $^{3}$H and carbon-14, which is $^{14}$C isotope, are particularly preferred, because they are easy to prepare and detect. Furthermore, replaced by heavier isotopes, such as deuterium, which is $^{2}$H, may provide therapeutic benefits due to the higher metabolic stability, such as prolonging the half-life in vivo or decreasing the dosage requirements, and thus may be preferred in some cases. Isotope-labeled compounds of formula (I) of the present disclosure and prodrugs thereof can be prepared generally by using readily available isotope-labeled reagents to replace non-isotope-labeled reagents in the following schemes and/or the procedures disclosed in the examples and preparation examples.

In addition, prodrugs are also included within the context of the present disclosure. The term "prodrug" as used herein refers to a compound that is converted in vivo into an active form that has medical effects by, for example, hydrolysis in blood. Pharmaceutically acceptable prodrugs are described in T. Higuchi and V. Stella, Prodrugs as Novel Delivery Systems, A.C.S. Symposium Series, Vol. 14, Edward B. Roche, ed., Bioreversible Carriers in Drug Design, American Pharmaceutical Association and Pergamon Press, 1987, and D. Fleisher, S. Ramon and H. Barbra "Improved oral drug delivery: solubility limitations overcome by the use of prodrugs", Advanced Drug Delivery Reviews (1996) 19(2) 115-130, each of which are incorporated herein by reference.

The prodrugs are any covalently bonded compounds of the present disclosure, which release the parent compound in vivo when the prodrug is administered to a patient. Prodrugs are typically prepared by modifying functional groups in such a way that the modifications can be cleaved either by routine manipulation or decompose in vivo to yield the parent compound. Prodrugs include, for example, compounds of the present disclosure wherein the hydroxyl, amino or sulfhydryl groups are bonded to any group that, when administered to a patient, cleaves to form the hydroxyl, amino or sulfhydryl groups. Thus, representative examples of prodrugs include (but are not limited to) the acetate/acetamide, formate/formamide and benzoate/benzamide derivatives of the hydroxyl, amino or sulfhydryl functional groups of the compounds of formula (I). Furthermore, in the case of carboxylic acid (—COOH), esters such as methyl esters and ethyl esters, etc. can be employed. The ester itself may be active in their own and/or hydrolyzable under in vivo conditions in the human body. Suitable pharmaceutically acceptable in vivo hydrolysable ester groups include those groups that can readily break down in the human body to release the parent acids or salts thereof.

Pharmaceutical Compositions, Formulations and Kits

In another aspect, the disclosure provides a pharmaceutical composition comprising a compound of the present disclosure (also referred to as the "active ingredient") and a pharmaceutically acceptable excipient. In certain embodiments, the pharmaceutical composition comprises an effective amount of the active ingredient. In certain embodiments, the pharmaceutical composition comprises a therapeutically effective amount of the active ingredient. In certain embodiments, the pharmaceutical composition comprises a prophylactically effective amount of the active ingredient.

A pharmaceutically acceptable excipient for use in the present disclosure refers to a non-toxic carrier, adjuvant or vehicle which does not destroy the pharmacological activity of the compound formulated together. Pharmaceutically acceptable carriers, adjuvants, or vehicles that may be used in the compositions of the present disclosure include, but are not limited to, ion exchangers, alumina, aluminum stearate, lecithin, serum proteins (e.g., human serum albumin), buffer substances (such as phosphate), glycine, sorbic acid, potassium sorbate, a mixture of partial glycerides of saturated plant fatty acids, water, salt or electrolyte (such as protamine sulfate), disodium hydrogen phosphate, potassium hydrogen phosphate, sodium chloride, zinc salt, silica gel, magnesium trisilicate, polyvinyl pyrrolidone, cellulose-based materials, polyethylene glycol, sodium carboxymethyl cellulose, polyacrylate, wax, polyethylene-polyoxypropylene block polymers, polyethylene glycol and lanolin.

The present disclosure also includes kits (e.g., pharmaceutical packs). Kits provided may include a compound disclosed herein, other therapeutic agents, and a first and a second containers (e.g., vials, ampoules, bottles, syringes, and/or dispersible packages or other materials) containing the compound disclosed herein or other therapeutic agents. In some embodiments, kits provided can also optionally include a third container containing a pharmaceutically acceptable excipient for diluting or suspending the compound disclosed herein and/or other therapeutic agent. In some embodiments, the compound disclosed herein provided in the first container and the other therapeutic agents provided in the second container is combined to form a unit dosage form.

The following formulation examples illustrate representative pharmaceutical compositions that may be prepared in accordance with this disclosure. The present disclosure, however, is not limited to the following pharmaceutical compositions.

Exemplary Formulation 1—Tablets: A compound of the present disclosure may be admixed as a dry powder with a dry gelatin binder in an approximate 1:2 weight ratio. A minor amount of magnesium stearate is added as a lubricant. The mixture is formed into 0.3-30 mg tablets (0.1-10 mg of active compound per tablet) in a tablet press.

Exemplary Formulation 2—Tablets: A compound of the present disclosure may be admixed as a dry powder with a dry gelatin binder in an approximate 1:2 weight ratio. A minor amount of magnesium stearate is added as a lubricant. The mixture is formed into 30-90 mg tablets (10-30 mg of active compound per tablet) in a tablet press.

Exemplary Formulation 3—Tablets: A compound of the present disclosure may be admixed as a dry powder with a dry gelatin binder in an approximate 1:2 weight ratio. A minor amount of magnesium stearate is added as a lubricant. The mixture is formed into 90-150 mg tablets (30-50 mg of active compound per tablet) in a tablet press.

Exemplary Formulation 4—Tablets: A compound of the present disclosure may be admixed as a dry powder with a dry gelatin binder in an approximate 1:2 weight ratio. A minor amount of magnesium stearate is added as a lubricant. The mixture is formed into 150-240 mg tablets (50-80 mg of active compound per tablet) in a tablet press.

Exemplary Formulation 5—Tablets: A compound of the present disclosure may be admixed as a dry powder with a dry gelatin binder in an approximate 1:2 weight ratio. A minor amount of magnesium stearate is added as a lubricant.

The mixture is formed into 240-270 mg tablets (80-90 mg of active compound per tablet) in a tablet press.

Exemplary Formulation 6—Tablets: A compound of the present disclosure may be admixed as a dry powder with a dry gelatin binder in an approximate 1:2 weight ratio. A minor amount of magnesium stearate is added as a lubricant. The mixture is formed into 270-450 mg tablets (90-150 mg of active compound per tablet) in a tablet press.

Exemplary Formulation 7—Tablets: A compound of the present disclosure may be admixed as a dry powder with a dry gelatin binder in an approximate 1:2 weight ratio. A minor amount of magnesium stearate is added as a lubricant. The mixture is formed into 450-900 mg tablets (150-300 mg of active compound) in a tablet press.

Exemplary Formulation 8—Capsules: A compound of the present disclosure may be admixed as a dry powder with a starch diluent in an approximate 1:1 weight ratio. The mixture is filled into 250 mg capsules (125 mg of active compound per capsule).

Exemplary Formulation 9—Liquid: A compound of the present disclosure (125 mg) may be admixed with sucrose (1.75 g) and xanthan gum (4 mg) and the resultant mixture may be blended, passed through a No. 10 mesh U.S. sieve, and then mixed with a previously made solution of microcrystalline cellulose and sodium carboxymethyl cellulose (11:89, 50 mg) in water. Sodium benzoate (10 mg), flavor, and color are diluted with water and added with stirring. Sufficient water may then be added to produce a total volume of 5 mL.

Exemplary Formulation 10—Injection: A compound of the present disclosure may be dissolved or suspended in a buffered sterile saline injectable aqueous medium to a concentration of approximately 5 mg/mL.

Administration

The pharmaceutical composition provided by the present disclosure may be administered by a variety of routes including, but not limited to, oral administration, parenteral administration, inhalation administration, topical administration, rectal administration, nasal administration, oral administration, vaginal administration, administration by implant or other means of administration. For example, parenteral administration as used herein includes subcutaneous administration, intradermal administration, intravenous administration, intramuscular administration, intra-articular administration, intraarterial administration, intrasynovial administration, intrasternal administration, intracerebroventricular administration, intralesional administration, and intracranial injection or infusion techniques.

Generally, the compounds provided herein are administered in an effective amount. The amount of the compound actually administered will typically be determined by a physician, in the light of the relevant circumstances, including the condition to be treated, the chosen route of administration, the actual compound administered, the age, weight, and response of the individual patient, the severity of the patient's symptoms, and the like.

When used to prevent the disorder disclosed herein, the compounds provided herein will be administered to a subject at risk for developing the condition, typically on the advice and under the supervision of a physician, at the dosage levels described above. Subjects at risk for developing a particular condition generally include those that have a family history of the condition, or those who have been identified by genetic testing or screening to be particularly susceptible to developing the condition.

The pharmaceutical compositions provided herein can also be administered chronically ("chronic administration"). Chronic administration refers to administration of a compound or pharmaceutical composition thereof over an extended period of time, e.g., for example, over 3 months, 6 months, 1 year, 2 years, 3 years, 5 years, etc, or may be continued indefinitely, for example, for the rest of the subject's life. In certain embodiments, the chronic administration is intended to provide a constant level of the compound in the blood, e.g., within the therapeutic window over the extended period of time.

The pharmaceutical compositions of the present disclosure may be further delivered using a variety of dosing methods. For example, in certain embodiments, the pharmaceutical composition may be given as a bolus, e.g., in order to raise the concentration of the compound in the blood to an effective level rapidly. The placement of the bolus dose depends on the desired systemic levels of the active ingredient throughout the body, e.g., an intramuscular or subcutaneous bolus dose allows a slow release of the active ingredient, while a bolus delivered directly to the veins (e.g., through an IV drip) allows a much faster delivery which quickly raises the concentration of the active ingredient in the blood to an effective level. In other embodiments, the pharmaceutical composition may be administered as a continuous infusion, e.g., by IV drip, to provide maintenance of a steady-state concentration of the active ingredient in the subject's body. Furthermore, in still yet other embodiments, the pharmaceutical composition may be administered as first as a bolus dose, followed by continuous infusion.

The compositions for oral administration can take the form of bulk liquid solutions or suspensions, or bulk powders. More commonly, however, the compositions are presented in unit dosage forms to facilitate accurate dosing. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. Typical unit dosage forms include prefilled, premeasured ampules or syringes of the liquid compositions or pills, tablets, capsules or the like in the case of solid compositions. In such compositions, the compound is usually a minor component (from about 0.1 to about 50% by weight or alternatively from about 1 to about 40% by weight) with the remainder being various vehicles or excipients and processing aids helpful for forming the desired dosing form.

With oral dosing, one to five and especially two to four and typically three oral doses per day are representative regimens. Using these dosing patterns, each dose provides from about 0.01 to about 20 mg/kg of the compound provided herein, with preferred doses each providing from about 0.1 to about 10 mg/kg, and especially about 1 to about 5 mg/kg.

Transdermal doses are generally selected to provide similar or lower blood levels than are achieved using injection doses, generally in an amount ranging from about 0.01 to about 20% by weight, alternatively from about 0.1 to about 20% by weight, alternatively from about 0.1 to about 10% by weight, and yet alternatively from about 0.5 to about 15% by weight.

Injection dose levels range from about 0.1 mg/kg/hour to at least 10 mg/kg/hour, all for from about 1 to about 120 hours and especially 24 to 96 hours. A preloading bolus of from about 0.1 mg/kg to about 10 mg/kg or more may also be administered to achieve adequate steady state levels. The maximum total dose is not expected to exceed about 2 g/day for a 40 to 80 kg human patient.

Liquid forms suitable for oral administration may include a suitable aqueous or nonaqueous vehicle with buffers, suspending and dispensing agents, colorants, flavours and the like. Solid forms may include, for example, any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate; a glidant such as colloidal silicon dioxide; a sweetening agent such as sucrose or saccharin; or a flavouring agent such as peppermint, methyl salicylate, or orange flavouring.

Injectable compositions are typically based upon injectable sterile saline or phosphate-buffered saline or other injectable excipients known in the art. As before, the active compound in such compositions is typically a minor component, often being from about 0.05 to 10% by weight with the remainder being the injectable excipient and the like.

Transdermal compositions are typically formulated as a topical ointment or cream containing the active ingredient(s). When formulated as an ointment, the active ingredients will typically be combined with either a paraffinic or a water-miscible ointment base. Alternatively, the active ingredients may be formulated in a cream with, for example an oil-in-water cream base. Such transdermal formulations are well-known in the art and generally include additional ingredients to enhance the dermal penetration of stability of the active ingredients or Formulation. All such known transdermal formulations and ingredients are included within the scope provided herein.

The compounds provided herein can also be administered by a transdermal device. Accordingly, transdermal administration may be accomplished using a patch either of the reservoir or porous membrane type, or of a solid matrix variety.

The above-described components for orally administrable, injectable or topically administrable compositions are merely representative. Other materials as well as processing techniques and the like are set forth in Part 8 of *Remington's Pharmaceutical Sciences,* 17th edition, 1985, Mack Publishing Company, Easton, Pennsylvania, which is incorporated herein by reference.

The compounds of the present disclosure can also be administered in sustained release forms or from sustained release drug delivery systems. A description of representative sustained release materials may be found in Remington's Pharmaceutical Sciences.

The present disclosure also relates to the pharmaceutically acceptable formulations of a compound of the present disclosure. In one embodiment, the formulation comprises water. In another embodiment, the formulation comprises a cyclodextrin derivative. The most common cyclodextrins are α-, β- and γ-cyclodextrins consisting of 6, 7 and 8 α-1,4-linked glucose units, respectively, optionally comprising one or more substituents on the linked sugar moieties, which include, but are not limited to, methylated, hydroxyalkylated, acylated, and sulfoalkylether substitution. In certain embodiments, the cyclodextrin is a sulfoalkyl ether β-cyclodextrin, e.g., for example, sulfobutyl ether β-cyclodextrin, also known as Captisol. See, e.g., U.S. Pat. No. 5,376,645. In certain embodiments, the formulation comprises hexapropyl-β-cyclodextrin (e.g., 10-50% in water).

Treatment

The present disclosure provides compounds with biological properties that enable these compounds to treat or ameliorate diseases of concern that may involve kinases, the symptoms of these diseases, or the effects of other physiological events mediated by kinases.

For example, the compounds of the present disclosure show inhibition of tyrosine kinase activity of Ret(Reaaranged during transfection), ABL1(E255K)-phosphorylated, ABL1(F317I)-nonphosphorylated, ABL1(F317L)-nonphosphorylated, ABL1(H396P)-nonphosphorylated, ABL1(M351T)-phosphorylated, ABL1(Q252H)-phosphorylated, ABL1(F317I)-phosphorylated, ABL1(F317L)-phosphorylated, ABL1(H396P)-phosphorylated, ABL1(Q252H)-nonphosphorylated, ABL1(T315I)-nonphosphorylated, ABL1(T315I)-phosphorylated, ABL1(Y253F)-phosphorylated, ABL1-nonphosphorylated, ABL1-phosphorylated, AB L2, ALK(L1196M), AMPK-alpha1, AMPK-alpha2, ANKK1, AURKB, AURKC, AXL, BLK, BMX, BRAF, BRAF (V600E), BRK, BTK, CAMK1, CAMKK1, CAMKK2, CDC2L1, CDC2L2, CDC2L5, CDK11, CDK2, CDK5, CDK7, CDK8, CDKL1, CDKL2, CDKL3, CHEK2, CIT, CLK1, CLK4, CSF1R, CSK, CTK, DDR1, DDR2, DLK, EGFR, EGFR(E746-A750del), EGFR(G719C), EGFR (G719S), EGFR(L747-E749del, A750P), EGFR(L747-S752del, P753S), EGFR(L747-T751del,Sins), EGFR (L858R), EGFR(L858R,T790M), EGFR(L861Q), EGFR (5752-1759del), EGFR(T790M), EPHA1, EPHA2, EPHA3, EPHA4, EPHA5, EPHA6, EPHA7, EPHA8, EPHB1, EPHB2, EPHB4, EPHB6, ERBB2, ERBB4, ERK8, FAK, FER, FES, FGFR1, FGFR2, FGFR3, FGFR3(G697C), FGFR4, FGR, FLT1, FLT3, FLT3(D835H), FLT3(D835V), FLT3(D835Y), FLT3(ITD), FLT3(ITD,D835V), FLT3(ITD, F691L), FLT3(K663Q), FLT3(N841I), FLT3(R834Q), FLT4, FRK, FYN, GAK, GCN2(Kin.Dom.2,S808G), HCK, HIPK4, HPK1, IKK-alpha, IKK-beta, IRAK1, IRAK4, ITK, JAK1(JH1domain-catalytic), JAK2(JH1domain-catalytic), JAK3(JH1domain-catalytic), JNK1, JNK2, JNK3, KIT, KIT (A829P), KIT(D816H), KIT(D816V), KIT(L576P), KIT (V559D), KIT(V559D,T670I), KIT(V559D,V654A), LCK, LIMK1, LIMK2, LOK, LRRK2, LRRK2(G2019S), LTK, LYN, MAK, MAP3K2, MAP3K3, MAP4K2, MAP4K3, MAP4K4, MAP4K5, MEK5, MELK, MERTK, MET, MET (M1250T), MINK, MKNK2, MLK1, MLK2, MLK3, MST1, MST1R, MST2, MUSK, MYLK2, MYO3A, MYO3B, NDR2, NEK1, NEK11, NEK4, NEK5, NEK9, NLK, p38-alpha, p38-beta, p38-delta, p38-gamma, PCTK2, PDGFRA, PDGFRB, PFCDPK1(*P.falciparum*), PFTAIRE2, PFTK1, PKAC-alpha, PKAC-beta, PYK2, RAF1, RET, RET(M918T), RET(V804L), RET(V804M), RIPK1, RIPK2, RIPK4, ROCK2, RPS6KA4(Kin.Dom.1-N-terminal), RSK2(Kin.Dom.1-N-terminal), RSK3(Kin.DoN-terminal), S6K1, SIK, SLK, SRC, SRMS, SRPK1, STK33, STK35, STK36, SYK, TAK1, TAOK2, TAOK3, TEC, TESK1, TGFBR2, TIE1, TIE2, TNIK, TNK1, TNK2, TNNI3K, TRKA, TRKB, TRKC, TTK, TXK, TYK2 (JH1domain-catalytic), TYRO3, ULK3, VEGFR2, YES, YSK4, ZAK, ZAP70 or FGFR(Fibroblast growth factor receptor), as well as other tyrosine kinases believed to regulate the growth, development and/or metastasis of cancer.

Substances of the present disclosure are also used for treating Bcr-Abl kinase mediated diseases, disorders or conditions selected from the groups consisting of: respiratory diseases, allergies, rheumatoid arthritis, osteoarthritis, rheumatic disorders, psoriasis, ulcerative colitis, regional ileitis, septic shock, proliferative disorders, atherosclerosis, post-transplant allograft rejection, diabetes, stroke, obesity or restenosis, leukemia, stromal tumor, thyroid cancer, systemic mast cell disease, eosinophilia syndrome, cystic fibrosis, rheumatoid arthritis, polyarthritis, dermatosclerosis, lupus erythematosus, graft versus host disease, neurofibroma, pulmonary hypertension, Alzheimer's disease, seminoma, dysgerminoma, mast cell tumor, lung cancer, bronchial carcinoma, dysgerminoma, testicular intraepithelial neoplasia, melanoma, breast cancer, neuroblastoma, papillary/follicular parathyroid hyperplasia or adenocarcinoma, colorectal adenomas, colorectal adenoma, ovarian cancer, prostate cancer, glioblastoma, brain tumor, malignant glioma, pancreatic cancer, malignant pleural mesothelioma, hemangioblastoma, hemangioma, kidney cancer, liver cancer, adrenal cancer, bladder cancer, stomach cancer, rectal cancer, vaginal cancer, cervical cancer, endometrial carcinoma, multiple myeloma, neck and head tumors, neoplasia and other hyperplasia or proliferative disease, or a combination thereof.

The present disclosure therefore provides the compound (I) and salts, solvates, and physiologically functional compounds thereof for use in therapy, particularly in the treatment of diseases and conditions mediated by inappropriate Bcr-Abl activity.

The inappropriate Bcr-Abl activity mentioned herein refers to any Bcr-Abl activity that deviates from the expected normal Bcr-Abl activity in a particular mammalian subject.

Inappropriate Bcr-Abl activity can take the form of, for example, the following: abnormally increased activity, or aberrations in the timing and/or control of Bcr-Abl activity. Such inappropriate activity can be caused by, for example, overexpression or mutation of protein kinases that cause inappropriate or uncontrolled activation.

In another embodiment, the present disclosure relates to methods for regulating, controlling, or inhibiting Bcr-Abl in order to prevent and/or treat disorders related to dysregulated or inappropriate Bcr-Abl activity.

In another embodiment, the disease mediated by Bcr-Abl activity is a respiratory disease. In another embodiment, the disease is a proliferative disease. In yet another embodiment, the disease is cancer. In another embodiment, the disease is leukemia.

In another embodiment, the present disclosure provides the use of a compound of formula (I) or a pharmaceutically acceptable salt or solvate thereof, or a physiologically functional derivative thereof in the manufacture of a medicament for the treatment of Bcr-Abl activity-mediated diseases.

Another aspect of the present disclosure is the use of a compound of formula (I) or a pharmaceutically acceptable salt thereof in the manufacture of a medicament for the treatment of Bcr-Abl-mediated diseases or Bcr-Abl-mediated conditions.

In another embodiment, the present disclosure provides a method of treating a mammal suffering from a condition mediated by Bcr-Abl activity, the method comprising: administering to the mammal an effective amount of the compound of formula (I) or its pharmaceutically acceptable salt, solvate or physiologically functional derivative thereof.

The effective amount of the compound of the present disclosure is usually at an average daily dose of 0.01 mg to 50 mg compound/kg patient body weight, preferably 0.1 mg to 25 mg compound/kg patient body weight, in single or multiple dosages. Generally, the compound of the present disclosure can be administered to a patient in need of such treatment at a daily dose ranging from about 1 mg to about 3500 mg per patient, preferably 10 mg to 1000 mg. For example, the daily dose per patient can be 10, 20, 30, 40, 50, 60, 70, 80, 90, 100, 150, 200, 250, 300, 350, 400, 500, 600, 700, 800, 900 or 1000 mg. The compound of the present disclosure can be administered once or multiple times daily, weekly (or at intervals of several days) or on an intermittent schedule. For example, the compound can be administered one or more times per day on a weekly basis (e.g. every Monday), timelessly or for several weeks, for example 4-10 weeks. Alternatively, it may be administered daily for several days (e.g., 2-10 days), and then a drug holiday for few days (e.g., 1-30 days), repeat the cycle arbitrarily or in a given number of times, such as 4-10 times. For example, the compound of the present disclosure can be administered daily for 5 days, and then a drug holiday for 9 days, and then administered daily for 5 days, then a drug holiday for 9 days, and so on, repeating the cycle arbitrarily or repeating 4-10 times in total.

Combination Therapy

The compounds of the present disclosure, the salts and solvates thereof, and physiologically functional derivatives thereof can be used alone or in combination with other therapeutic agents for the treatment of various protein kinase-mediated diseases and conditions. The combination therapy according to the present disclosure therefore includes the administration of at least one compound of formula (I) or a pharmaceutically acceptable salt or solvate or physiologically functional derivative thereof and the use of at least one other pharmaceutically active agent. One or more compounds of formula (I) and one or more other pharmaceutically active agents can be administered together or separately, and can be administered simultaneously or sequentially in any order when administered separately. The amount and relative timing of administration of one or more compounds of formula (I) and one or more other pharmaceutically active agents will be selected to achieve the desired combined therapeutic effect.

For the treatment of cancer, a compound of formula (I) may be combined with one or more of anticancer agents. Examples of such agents can be found in Cancer Principles and Practice of Oncology by V. T. Devita and S. Hellman (editors), $6^{th}$ edition (Feb. 15, 2001), Lippincott Williams & Wilkins Publishers. A person of ordinary skill in the art would be able to discern which combinations of agents would be useful based on the particular characteristics of the drugs and the cancer involved. Such anti-cancer agents include, but are not limited to, the following: (1) estrogen receptor modulator such as diethylstibestral, tamoxifen, raloxifene, idoxifene, LY353381, LY117081, toremifene, fluoxymestero, and SH646; (2) other hormonal agents including aromatase inhibitors (e.g., aminoglutethimide, tetrazole anastrozole, letrozole and exemestane), luteinizing hormone release hormone (LHRH) analogues, ketoconazole, goserelin acetate, leuprolide, megestrol acetate and mifepristone; (3) androgen receptor modulator such as finasteride and other 5α-reductase inhibitors, nilutamide, flutamide, bicalutamide, liarozole, and abiraterone acetate; (4) retinoid receptor modulator such as bexarotene, tretinoin, 13-cis-retinoic acid, 9-cis-retinoic acid, α-difluoromethylornithine, ILX23-7553, trans-N-(4'-hydroxyphenyl) retinamide, and N-4-carboxyphenyl retinamide; (5) antiproliferative agent such asantisense RNA and DNA oligonucleotides such as G3139, ODN698, RVASKRAS, GEM231, and INX3001, and antimetabolites such as enocitabine, carmofur, tegafur, pentostatin, doxifluridine, trimetrexate, fludarabine, capecitabine, galocitabine, cytarabine ocfosfate, fosteabine sodium hydrate, raltitrexed, paltitrexid, emitefur, tiazofurin, decitabine, nolatrexed, pemetrexed, nelarabine, 2'-deoxy-2'-methylidenecytidine, 2'-fluoromethylene-2'-deoxycytidine, N6-[4-deoxy-4-[N2-[2(E),4(E)-tetradeca-dienoyl]glycylamino]-L-glycero-B-L-manno-heptopyranosyl]adenine, aplidine, ecteinascidin, troxacitabine, aminopterin, 5-fluorouracil, floxuridine, methotrexate, folinic acid, hydroxyurea, thioguanine (6-TG), mercaptopurine (6-MP), cytarabine, pentostatin, fludarabine phosphate, cladribine (2-CDA), asparaginase, gemcitabine, alanosine, swainsonine, lometrexol, dexrazoxane, methioninase, and 3-aminopyridine-2-carboxaldehyde thiosemicarbazone; (6) prenyl-protein transferase inhibitor including farnesyl-protein transferase (FPTase), geranylgeranyl-protein transferase type I (GGPTase-I), and geranylgeranyl-protein transferase type-H (GGPTase-II, also called Rab GGPTase); (7) HMG-CoA reductase inhibitor such as lovastatin, simvastatin, pravastatin, atorvastatin, fluvastatin and rosuvastatin; (8) angiogenesis inhibitor such as inhibitors of the tyrosine kinase receptors Flt-1 (VEGFR1) and Flk-UDR (VEGFR2), inhibitors of epidermal-derived, fibroblast-derived, or platelet derived growth factors, MMP (matrix metalloprotease) inhibitors, integrin blockers, interferon-α, interleukin-12, erythropoietin (epoietin-α), granulocyte-CSF (filgrastin), granulocyte, macrophage-CSF (sargramostim), pentosan polysulfate, cyclooxygenase inhibitors, steroidal anti-inflammatories, carboxyamidotriazole, combretastatin A-4, squalamine, 6-O-chloroacetyl-carbonyl)-fumagillol, thalidomide, angiostatin, troponin-1, angiotensin II antagonists, heparin, carboxypeptidase U inhibitors, and antibodies against the following subjects: VEGF, endostatin, ukrain, ranpirnase, IM862, acetyldinanaline, 5-amino-1-[[3,5-dichloro-4-(4-chlorobenzoyl)phenyl]methyl]-1H-1,2,3-triazole-4-carboxamide, CM101, squalamine, combretastatin, RPI4610, NX31838, sulfated mannopentaose phosphate, and 3-[(2,4-dimethylpyrrol-5-yl)methylene]-2-indolinone (SU5416); (9) PPAR-γ agonists, PPAR-δ agonists, thiazolidinediones (such as DRF2725, CS-011, troglitazone, rosiglitazone, and pioglitazone), fenofibrate, gemfibrozil, clofibrate, GW2570, SB219994, AR-H039242, JTT-501, MCC-555, GW2331, GW409544, NN2344, KRP297, NP0110, DRF4158, NN622, GI262570, PNU182716, DRF552926, 2-[(5,7-dipropyl-3-trifluotomethyl-1,2-benzisoxazol-6-yl)oxy]-2-methylpropionic acid (disclosed in U.S. Ser. No. 09/782,856), and (2R)-7-(3-(2-chloro-4-(4-fluorophenoxy)phenoxy)propoxy)-2-ethylchromane-2-carboxylic acid (disclosed in U.S. Ser. No. 60/235,708 and 60/244,697); (9) inhibitor of inherent multidrug resistance including inhibitors of p-glycoprotein (P-gp), such as LY335979, XR9576, OC144-093, R101922, VX853 and PSC833 (valspodar); (10) inhibitor of cell proliferation and survival signaling such as inhibitors of EGFR (for example gefitinib erlotinib, icotinib and osimertinib (AZD9291)), inhibitors of ERB-2 (for example trastuzumab), inhibitors of IGF1R such as MK-0646 (dalotuzumab), inhibitors of CD20 (rituximab), inhibitors of cytokine receptors, inhibitors of MET, inhibitors of PI3K family kinase (for example LY294002), serine/threonine kinases (including but not limited to inhibitors of Akt such as described in (WO 03/086404, WO 03/086403, WO 03/086394, WO 03/086279, WO 02/083675, WO 02/083139, WO 02/083140 and WO 02/083138), inhibitors of Raf kinase (for example BAY-43-9006), inhibitors of MEK (for example CI-1040 and PD-098059) and inhibitors of mTOR (for example Wyeth CCI-779 and Ariad AP23573); (11) a bisphosphonate such as etidronate, pamidronate, alendronate, risedronate, zoledronate, ibandronate, incadronate or cimadronate, clodronate, EB-1053, minodronate, neridronate, piridronate and tiludronate; (12) γ-secretase inhibitors, (13) agents that interfere with receptor tyrosine kinases (RTKs) including inhibitors of c-Kit, Eph, PDGF, Flt3 and c-Met; (14) agent that interferes with a cell cycle checkpoint including inhibitors of ATR, ATM, the Chk1 and Chk2 kinases and cdk and cdc kinase inhibitors and are specifically exemplified by 7-hydroxystaurosporin, flavopiridol, CYC202 (Cyclacel) and BMS-387032; (15) BTK inhibitors such as PCI32765, AVL-292 and AVL-101; (16) PARP inhibitors including iniparib, olaparib, AG014699, ABT888 and MK4827; (16) ERK inhibitors; (17) mTOR inhibitors such as rapamycin, 42-(dimethylphosphinate) rapamycin, temsirolimus, everolimus; (18) cytotoxic/cytostatic agents.

"Cytotoxic/cytostatic agents" refer to compounds which cause cell death or inhibit cell proliferation primarily by interfering directly with the cell's functioning or inhibit or interfere with cell mytosis, including alkylating agents, tumor necrosis factors, intercalators, hypoxia activatable compounds, microtubule inhibitors/microtubule-stabilizing agents, inhibitors of mitotic kinesins, inhibitors of histone deacetylase, inhibitors of kinases involved in mitotic progression, antimetabolites; biological response modifiers; hormonal/anti-hormonal therapeutic agents, haematopoietic growth factors, monoclonal antibody targeted therapeutic agents, topoisomerase inhibitors and proteasome inhibitors.

Examples of cytotoxic agents include, but are not limited to, sertenef, cachectin, chlorambucil, cyclophosphamide, ifosfarnide, mechiorethamine, melphalan, uracil mustard, thiotepa, busulfan, carmustine, lomustine, streptozocin, tasonermin, lonidamine, carboplatin, altretamine, dacarbazine, procarbazine, prednimustine, dibromodulcitol, ranimustine, fotemustine, nedaplatin, oxaliplatin, temozolomide, heptaplatin, estramustine, improsulfan tosilate, trofosfamide, nimustine, dibrospidium chloride, pumitepa, lobaplatin, satraplatin, profiromycin, cisplatin, irofulven, dexifosfamide, cis-aminedichloro(2-methyl-pyridine)platinum, benzylguanine, glufosfamide, GPX100, (trans, trans, trans)-bis-mu-(hexane-1,6-diamine)-mu-[diamine-platinum (II)]bis[diamine(chloro)platinum (II)]tetrachloride, diarizidinylspermine, arsenic trioxide, 1-(11-dodecylamino-10-hydroxyundecyl)-3,7-dimethylxanthine, zorubicin, doxorubicin, daunorubicin, idarubicin, anthracenedione, bleomycin, mitomycin C, dactinomycin, plicatomycin, bisantrene, mitoxantrone, pirarubicin, pinafide, valrubicin, amrubicin, antineoplaston, 3'-deamino-3'-morpholino-13-deoxo-10-hydroxycarminomycin, kanamycin, galarubicin, elinafide, MEN10755, and 4-demethoxy-3-deamino-3-aziridinyl-4-methylsulphonyl-daunorubicin.

Examples of proteasome inhibitors include but are not limited to lactacystin and bortezomib.

Examples of microtubule inhibitors/microtubule-stabilising agents include vincristine, vinblastine, vindesine, vinzolidine, vinorelbine, vindesine sulfate, 3',4'-didehydro-4'-deoxy-8-norvincaleukoblastine, podophyllotoxins (e.g., etoposide (VP-16) and teniposide (VM-26)), paclitaxel, docetaxol, rhizoxin, dolastatin, mivobulin isethionate, auristatin, cemadotin, RPR109881, BMS184476, vinflunine, cryptophycin, anhydrovinblastine, N,N-dimethyl-L-valyl-L-valyl-N-methyl-L-valyl-L-prolyl-L-proline-t-butylamide, TDX258, the epothilones (see for example U.S. Pat. Nos. 6,284,781 and 6,288,237) and BMS188797.

Some examples of topoisomerase inhibitors are topotecan, hycaptamine, irinotecan, rubitecan, 6-ethoxypropionyl-3',4'-O-exo-benzylidene-chartreusin, lurtotecan, 7-[2-(N-isopropylamino)ethyl]-(20S)camptothecin, BNP1350, BNPI1100, BN80915, BN80942, etoposide phosphate, teniposide, sobuzoxane, 2'-dimethylamino-2'-deoxy-etoposide, GL331, N-[2-(dimemylamino)ethyl]-9-hydroxy-5,6-dimethyl-6H-pyrido[4,3-b]carbazole-1-carboxamide, asulacrine, 2,3-(methylenedioxy)-5-methyl-7-hydroxy-8-methoxybenzo[c]-phenanthridinium, 5-(3-aminopropylamino)-7,10-dihydroxy-2-(2-hydroxyethylaminomethyl)-6H-pyrazolo[4,5, 1-de]acridin-6-one, N-[1-[2-(diethylamino)ethylamino]-7-methoxy-9-oxo-9H-thioxanthen-4-ylmethyl]formamide, N-(2-(dimethyiamino)ethyl)acridine-4-carboxamide, 6-[[2-(dimethylamino)ethyl]amino]-3-hydroxy-7H-indeno[2,1-c]quinolin-7-one, and dimesna.

Examples of "histone deacetylase inhibitors" include, but are not limited to, vorinostat, trichostatin A, oxamfiatin, PXD101, MG98, valproic acid and scriptaid.

"Inhibitors of kinases involved in mitotic progression" include, but are not limited to, inhibitors of aurora kinase, inhibitors of Polo-like kinases (PLK; in particular inhibitors of PLK-1), inhibitors of bub-1 and inhibitors of bub-R1. An example of an "aurora kinase inhibitor" is VX-680.

"Antiproliferative agents" includes antisense RNA and DNA oligonucleotides such as G3139, ODN698, RVASK-RAS, GEM231, and INX3001, and antimetabolites such as enocitabine, carmofur, tegafur, pentostatin, doxifluridine, trimetrexate, fludarabine, capecitabine, galocitabine, cytarabine ocfosfate, fosteabine sodium hydrate, raltitrexed, paltitrexid, emitefur, tiazofurin, decitabine, nolatrexed, pemetrexed, nelarabine, 2'-deoxy-2'-methylidenecytidine, 2'-fluoromethylene-2'-deoxycytidine, N6-[4-deoxy-4-[N2-[2,4-tetradecadienoyl]glycylamino]-L-glycero-B-L-manno-heptopyranosyl]adenine, aplidine, ecteinascidin, troxacitabine, aminopterin, 5-flurouracil, floxuridine, methotrexate, leucovorin, hydroxyurea, thioguanine (6-TG), mercaptopurine (6-MP), cytarabine, pentostatin, fludarabine phosphate, cladribine (2-CDA), asparaginase, gemcitabine, alanosine, swainsonine, lometrexol, dexrazoxane, methioninase, and 3-aminopyridine-2-carboxaldehyde thiosemicarbazone.

Non-limiting examples of suitable agents used in cancer therapy that may be combined with compounds of formula (I) include, but are not limited to, abarelix; aldesleukin; alemtuzumab; alitretinoin; allopurinol; altretamine; amifostine; anastrozole; arsenic trioxide; asparaginase; azacitidine; bendamustine; bevacizumab; bexarotene; bleomycin; bortezomib; busulfan; calusterone; capecitabine; carboplatin; carmustine; cetuximab; chlorambucil; cisplatin; cladribine; clofarabine; cyclophosphamide; cytarabine; dacarbazine; dactinomycin, actinomycin D; dalteparin sodium; erythropoietin; dasatinib; daunorubicin; degarelix; denileukin diftitox; dexrazoxane; docetaxel; adriamycin; dromostanolone propionate; eculizumab; Elliott's B Solution; eltrombopag; epirubicin; epoetin alfa; erlotinib; estramustine; etoposide phosphate; etoposide; everolimus; exemestane; filgrastim; floxuridine; fludarabine; fluorouracil; fulvestrant; iressa; tarceva; osimertinib; gemcitabine; gemtuzumab; goserelin acetate; histrelin acetate; hydroxyurea; ibritumomab tiuxetan; idarubicin; ifosfamide; imatinib mesylate; interferon alfa-2a; interferon alfa-2b; irinotecan; ixabepilone; lapatinib; lenalidomide; letrozole; leucovorin; leuprolide acetate; levamisole; lomustine; meclorethamine, chlormethine; megestrol acetate; melphalan, L-PAM; mercaptopurine; mesna; methotrexate; methoxsalen; mitomycin C; mitotane; mitoxantrone; nandrolone phenpropionate; nelarabine; nilotinib; Nofetumomab; ofatumumab; oprelvekin; oxaliplatin; paclitaxel; palifermin; pamidronate disodium; panitumumab; pazopanib; pegademase; pegaspargase; Pegfilgrastim; pemetrexed disodium; pentostatin; pipobroman; plerixafor; plicamycin, mithramycin; porfimer sodium; pralatrexate; ibenzmethyzin; quinacrine; Rasburicase; raloxifene hydrochloride; Rituximab; romidepsin; romiplostim; sargramostim; sargramostim; satraplatin; sorafenib; streptozocin; sunitinib maleate; tamoxifen; temozolomide; temsirolimus; teniposide; testolactone; thioguanine; thiotepa; topotecan; toremifene; tositumomab; trastuzumab; tretinoin; uracil mustard; valrubicin; vinblastine; vincristine; vinorelbine; vorinostat; and zoledronic acid.

It is clear to those skilled in the art that, where appropriate, the other one or more therapeutic ingredients may be used in the form of salt, such as alkali metal salt or amine salt or acid addition, or prodrug, or ester such as lower alkyl ester, or solvate such as hydrate to optim/ze the activity and/or stability and/or physical properties (such as solubility) of the therapeutic ingredient. It is also clear that, where appropriate, the therapeutic ingredients can be used in optically pure form.

The above-mentioned combination can be conveniently used in the form of a pharmaceutical composition, so a pharmaceutical composition comprising the above-mentioned combination and a pharmaceutically acceptable diluent or carrier represents another aspect of the present disclosure. These combinations are particularly useful for respiratory diseases and are conveniently suitable for inhalation or intranasal delivery.

The compounds of this combination can be administered sequentially or simultaneously in the form of separate or combined pharmaceutical compositions. Preferably, each compound is administered simultaneously in the form of combined pharmaceutical composition. Those skilled in the art will readily understand the appropriate dosage of the known therapeutic agent.

EXAMPLES

The present disclosure will be further described below in combination with specific embodiments. It should be understood that these examples are only used to illustrate the present disclosure and not to limit the scope of the present disclosure. The experimental methods without specific conditions in the following examples generally follow the conventional conditions or the conditions recommended by the manufacturer. Unless otherwise stated, parts and percentages are parts by weight and weight percent.

Generally, in the preparation process, each reaction is carried out in an inert solvent at a temperature from room temperature to reflux temperature (such as 0° C. to 100° C., alternatively 0° C. to 80° C.). The reaction time is usually 0.1-60 hours, alternatively 0.5-24 hours.

The abbreviations used in this article have the following meanings:

| | |
|---|---|
| APCI | Atmosphere Pressure Chemical Ionization |
| HAC | Glacial acetic acid |
| POCl$_3$ | Phosphorus oxychloride |
| Raney-Ni | Raney Nickel |
| TEA | Triethylamine |
| DCM | Dichloromethane |
| NBS | N-bromosuccinimide |
| DMF | N,N-dimethyl formamide |
| ACN | Acetonitrile |
| DIEA | N,N- diisopropylethylamine |
| THF | Tetrahydrofuran |
| NIS | N-iodosuccinimide |

Example 1: Preparation of 3-((8-amino-3-ethylimidazo[1,5-a]pyrazin-1-yl)ethynyl)-4-methyl-N-(4-((4-methylpiperazin-1-yl)methyl)-3-(trifluoromethyl)phenyl)benzamide (Compound I-1)

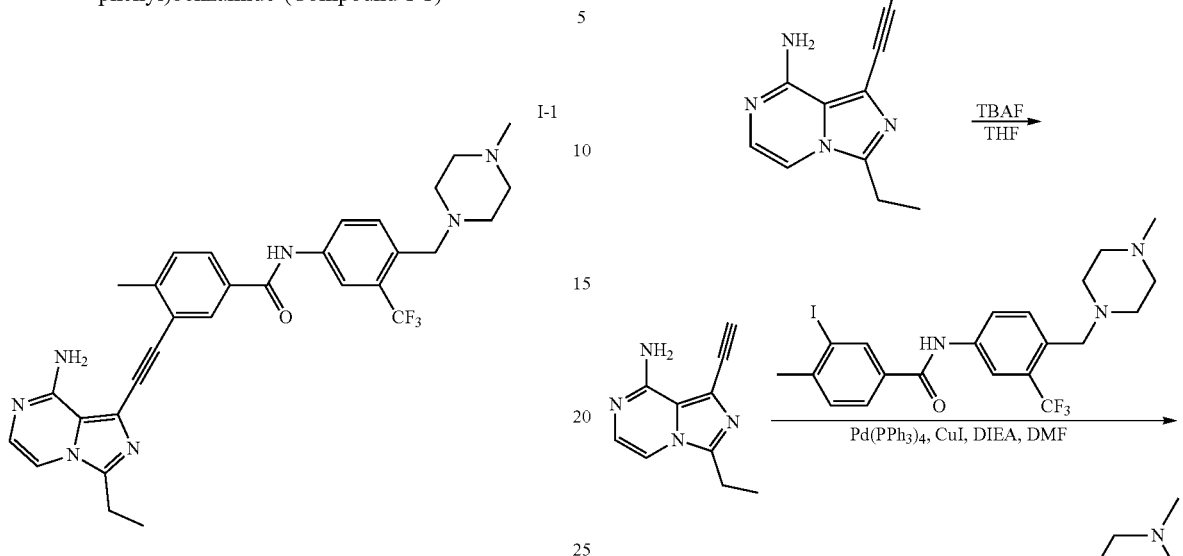

The following route was used for the synthesis:

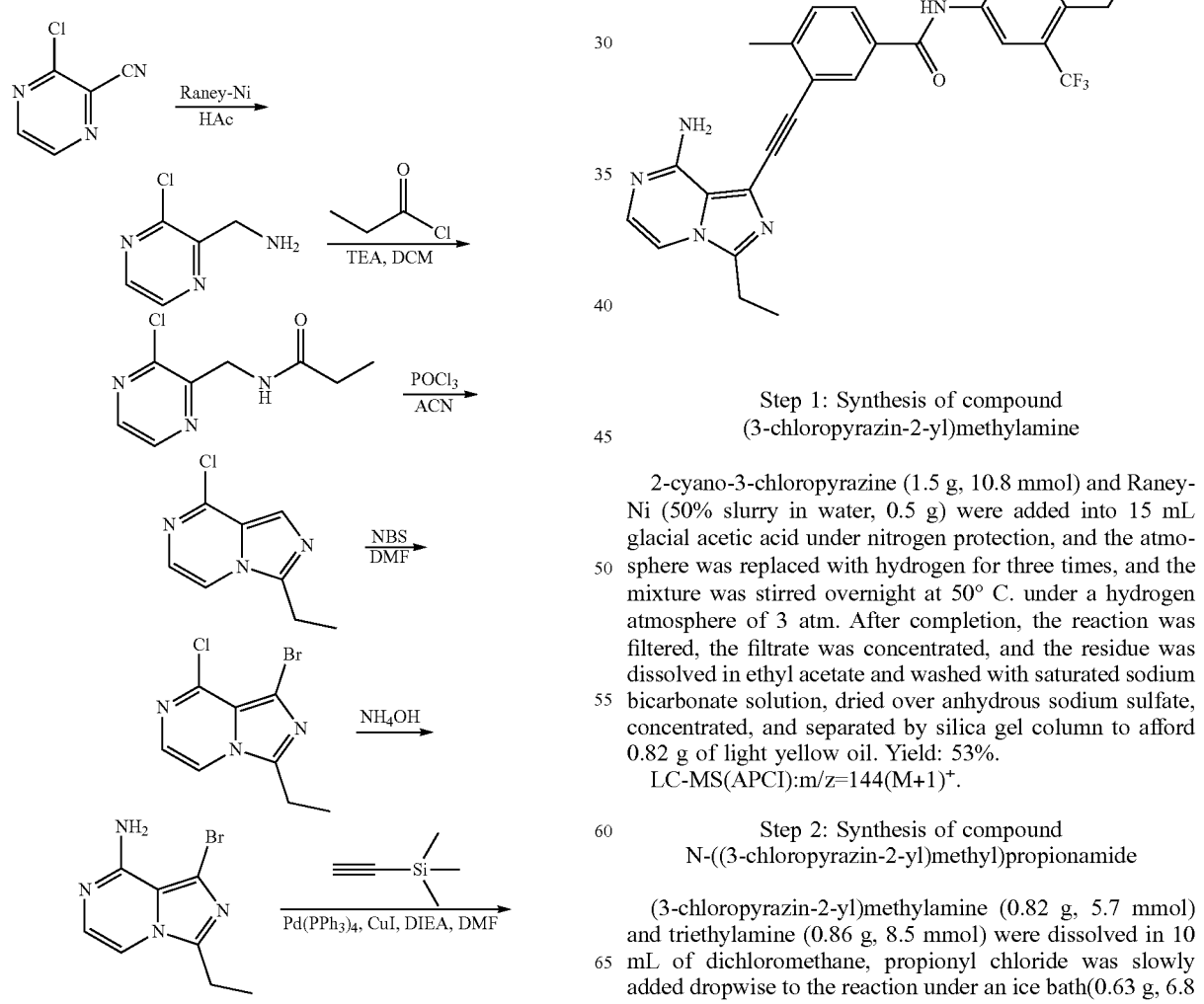

Step 1: Synthesis of compound (3-chloropyrazin-2-yl)methylamine 2-cyano-3-chloropyrazine (1.5 g, 10.8 mmol) and Raney-Ni (50% slurry in water, 0.5 g) were added into 15 mL glacial acetic acid under nitrogen protection, and the atmosphere was replaced with hydrogen for three times, and the mixture was stirred overnight at 50° C. under a hydrogen atmosphere of 3 atm. After completion, the reaction was filtered, the filtrate was concentrated, and the residue was dissolved in ethyl acetate and washed with saturated sodium bicarbonate solution, dried over anhydrous sodium sulfate, concentrated, and separated by silica gel column to afford 0.82 g of light yellow oil. Yield: 53%.
LC-MS(APCI):m/z=144(M+1)$^+$.

Step 2: Synthesis of compound N-((3-chloropyrazin-2-yl)methyl)propionamide (3-chloropyrazin-2-yl)methylamine (0.82 g, 5.7 mmol) and triethylamine (0.86 g, 8.5 mmol) were dissolved in 10 mL of dichloromethane, propionyl chloride was slowly added dropwise to the reaction under an ice bath(0.63 g, 6.8 mmol). The ice bath was removed after the completion of addition, and the mixture was stirred at room temperature overnight. TLC was used to monitor the completion of the reaction. The reaction solution was washed with 1N hydrochloric acid, 5% NaHCO$_3$ solution and saturated brine, respectively. The organic phase was dried over anhydrous sodium sulfate, concentrated, and separated by silica gel column to afford 0.7 g of light yellow oil. Yield: 62%. LC-MS(APCI):m/z=200(M+1)$^+$.

Step 3: Synthesis of compound 8-chloro-3-ethylimidazo[1,5-a]pyrazine

N-((3-chloropyrazin-2-yl)methyl)propionamide (0.7 g, 3.5 mmol) was dissolved in 15 mL anhydrous acetonitrile, phosphorus oxychloride (2.1 g, 14 mmol) was added, and the reaction was heated to 60° C. and reacted overnight. After the completion of reaction, the solvent was evaporated, the residue was slowly added to ice water and extracted with ethyl acetate (10 mL*3). The organic phase was washed with saturated sodium bicarbonate solution and saturated brine, respectively, dried over anhydrous sodium sulfate, concentrated, and separated by silica gel column to afford 0.51 g of light yellow solid. Yield: 80%. LC-MS (APCI):m/z=182(M+1)$^+$.

Step 4: Synthesis of compound 1-bromo-8-chloro-3-ethylimidazo[1,5-a]pyrazine 8-chloro-3-ethylimidazo[1,5-a]pyrazine (0.51 g, 2.8 mmol) was dissolved in 10 mL DMF, NBS was added in batches under an ice bath (0.55 g, 3.1 mmol), and the reaction was naturally warmed to room temperature and reacted overnight. After the completion of reaction, 20 mL of water was added to the reaction solution, which was extracted with ethyl acetate (10 mL*3), the organic phase was washed with 10 mL of saturated brine, dried over anhydrous sodium sulfate, concentrated, and separated by silica gel column to afford 0.51 g of light yellow solid. Yield: 70%. LC-MS(APCI):m/z=260(M+1)$^+$.

Step 5: Synthesis of compound 1-bromo-3-ethyl-imidazo[1,5-a]pyrazine-8-amine 1-bromo-8-chloro-3-ethylimidazo[1,5-a]pyrazine (0.51 g, 2.0 mmol) and 10 mL of concentrated ammonia solution were added to a 50 mL sealed tube, the reaction was heated to 120° C. in an oil bath and reacted overnight. After the completion of reaction, the reaction was cooled to room temperature, the solvent was removed by rotary evaporation to afford 0.4 g of white powdery solid. Yield: 84%. LC-MS (APCI):m/z=241(M+1)$^+$.

Step 6: Synthesis of compound 3-ethyl-1-((trimethylsilyl)ethynyl)imidazo[1,5-a]pyrazine-8-amine 1-bromo-3-ethylimidazo[1,5-a]pyrazine-8-amine (170 mg, 0.71 mmol), trimethylsilylacetylene (90 mg, 0.92 mmol), Pd(PPh$_3$)$_4$ (23 mg, 0.02 mmol), CuI (8 mg, 0.04 mmol) and 0.24 mL N,N-diisopropylethylamine were added into 5 mL DMF, the atmosphere was replaced with nitrogen for 3 times, and the reaction was heated to 90° C. and reacted for 3 hours. After the completion of reaction, the reaction was cooled to room temperature, added with 15 mL of water, extracted with ethyl acetate (15 mL*3), and the organic phase was washed with 10 mL saturated brine, dried over anhydrous sodium sulfate, concentrated, and separated by silica gel column to afford 120 mg of light yellow solid. Yield: 66%.

LC-MS (APCI): m/z=259(M+1)$^+$.

Step 7: Synthesis of compound 3-ethyl-1-ethynylimidazo[1,5-a]pyrazine-8-amine

3-Ethyl-1-((trimethylsilyl)ethynyl)imidazo[1,5-a]pyrazine-8-amine (120 mg, 0.47 mmol) was dissolved in 5 mL tetrahydrofuran, tetrabutylammonium fluoride (0.25 g, 0.94 mmol) was added, and the reaction was stirred at room temperature for 1 hour. The solvent was removed by rotary evaporation, 10 mL of water was added to the residue, which was extracted with ethyl acetate (10 mL*3), and the organic phase was washed with 10 mL of saturated brine, dried over anhydrous sodium sulfate, concentrated, and separated by silica gel column to afford 75 mg of light yellow solid. Yield: 88%. LC-MS(APCI):m/z=187(M+1)$^+$.

Step 8: Synthesis of compound 3-((8-amino-3-ethylimidazo[1,5-a]pyrazin-1-yl)ethynyl)-4-methyl-N-(4-((4-methylpiperazin-1-yl)methyl)-3-(trifluoromethyl)phenyl)benzamide 3-iodo-4-methyl-N-(4-((4-methylpiperazin-1-yl)methyl)-3-(trifluoromethyl)phenyl)benzamide (160 mg, 0.31 mmol), 3-ethyl-1-ethynylimidazo[1,5-a]pyrazine-8-amine (75 mg, 0.4 mmol), Pd(PPh$_3$)$_4$ (11 mg, 0.01 mmol), CuI (4 mg, 0.02 mmol) and 0.12 mL N,N-diisopropylethylamine were added into 3 mL DMF, the atmosphere was replaced with nitrogen for 3 times, and the reaction was heated to 90° C. and reacted for 3 hours. After the completion of reaction, the reaction was cooled to room temperature, added with 10 mL of water, extracted with ethyl acetate (10 mL*3), and the organic phase was washed with 10 mL of saturated brine, dried over anhydrous sodium sulfate, concentrated, and separated by silica gel column to afford 110 mg of light yellow solid. Yield: 62%.

LC-MS(APCI):m/z=576(M+1)$^+$. 1H NMR (400 MHz, DMSO-d$_6$) δ 10.57 (s, 1H), 8.23 (d, J=2.1 Hz, 2H), 8.11-8.05 (m, 1H), 7.92 (dd, J=8.0, 2.0 Hz, 1H), 7.71 (d, J=8.5 Hz, 1H), 7.60 (d, J=4.9 Hz, 1H), 7.52 (d, J=8.1 Hz, 1H), 7.11 (d, J=4.9 Hz, 1H), 6.77-6.62 (m, 2H), 3.59 (s, 2H), 2.93 (q, J=7.5 Hz, 2H), 2.55 (s, 3H), 2.49-2.40 (m, 8H), 2.33 (s, 3H), 1.30 (t, J=7.5 Hz, 3H).

Example 2: Preparation of 3-((8-amino-3-ethylimidazo[1,5-a]pyrazin-1-yl)ethynyl)-4-methyl-N-(3-(trifluoromethyl)phenyl)benzamide (Compound I-2)

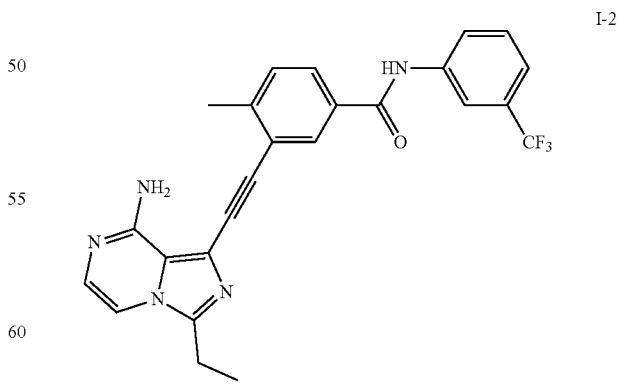

I-2

The title compound I-2 was prepared according to the synthetic method described in Example 1, and compound 3-iodo-4-methyl-N-(3-(trifluoromethyl)phenyl)benzamide was used to replace 3-iodo-4-methyl-N-(4-((4-methylpiperazin-1-yl)methyl)-3-(trifluoromethyl)phenyl)benzamide in step 8. LC-MS(APCI):m/z=464(M+1)$^+$. 1H NMR (400 MHz, DMSO-d$_6$) δ 10.60 (s, 1H), 8.29-8.21 (m, 2H), 8.08 (d, J=7.9 Hz, 1H), 7.92 (dd, J=8.0, 2.0 Hz, 1H), 7.65-7.57 (m, 2H), 7.53 (d, J=8.1 Hz, 1H), 7.47 (d, J=7.5 Hz, 1H), 7.11 (d, J=5.0 Hz, 1H), 6.71 (s, 2H), 2.93 (q, J=7.5 Hz, 2H), 2.55 (s, 3H), 1.31 (t, J=7.5 Hz, 3H).

Example 3: Preparation of 3-((8-amino-3-methyl-imidazo[1,5-a]pyrazin-1-yl)ethynyl)-4-methyl-N-(4-((4-methylpiperazin-1-yl)methyl)-3-(trifluoromethyl)phenyl)benzamide (Compound I-3)

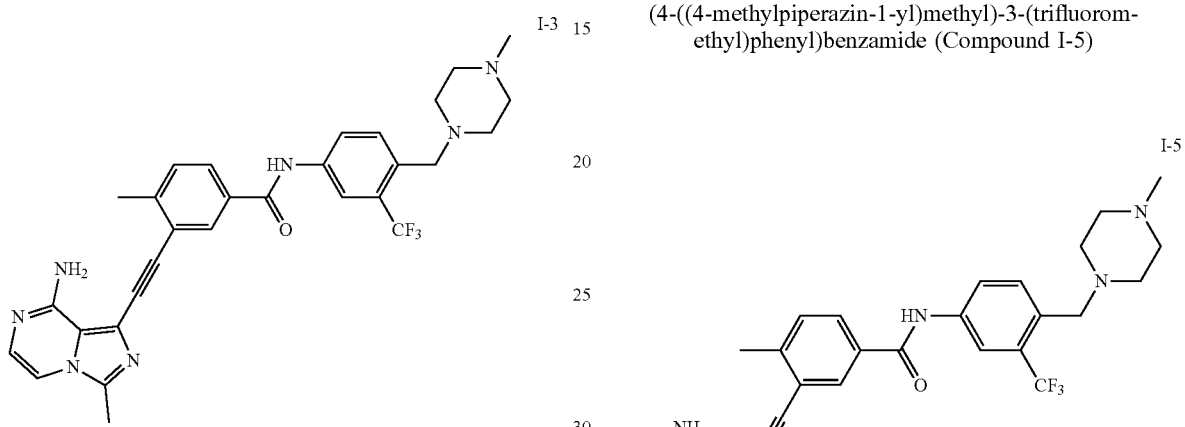

The title compound 1-3 was prepared according to the synthetic method described in Example 1, and compound acetyl chloride was used to replace propionyl chloride in step 2. LC-MS(APCI):m/z=562(M+1)$^+$. 1H NMR (400 MHz, DMSO-d$_6$) δ 10.57 (s, 1H), 8.22 (dd, J=6.4, 2.0 Hz, 2H), 8.08 (dd, J=8.6, 2.1 Hz, 1H), 7.92 (dd, J=7.9, 1.9 Hz, 1H), 7.71 (d, J=8.6 Hz, 1H), 7.54 (dd, J=15.7, 6.3 Hz, 2H), 7.16 (d, J=26.6 Hz, 1H), 6.69 (s, 2H), 3.60 (s, 2H), 2.55 (d, J=3.5 Hz, 6H), 2.50-2.42 (m, 8H), 2.38 (s, 3H).

Example 4: Preparation of 3-((8-amino-3-isopropylimidazo[1,5-a]pyrazin-1-yl)ethynyl)-4-methyl-N-(4-((4-methylpiperazin-1-yl)methyl)-3-(trifluoromethyl)phenyl)benzamide (Compound I-4)

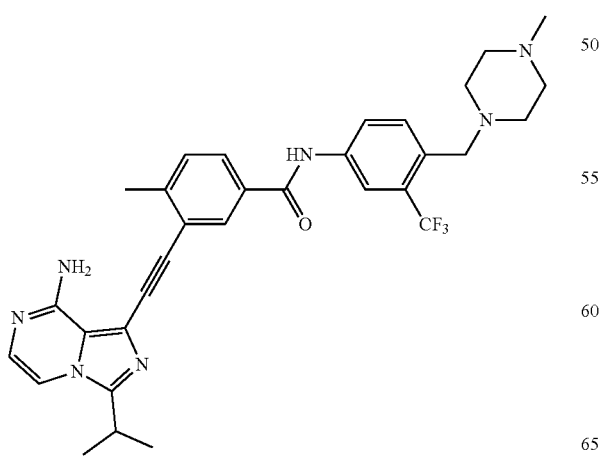

The title compound 1-4 was prepared according to the synthetic method described in Example 1, and compound isobutyryl chloride was used to replace propionyl chloride in step 2. LC-MS(APCI):m/z=590(M+1)$^+$. 1H NMR (400 MHz, DMSO-d$_6$) δ10.56 (s, 1H), 8.23 (dd, J=5.6, 2.0 Hz, 2H), 8.08 (dd, J=8.5, 2.2 Hz, 1H), 7.92 (dd, J=8.0, 2.0 Hz, 1H), 7.71 (d, J=8.6 Hz, 1H), 7.66 (d, J=5.0 Hz, 1H), 7.52 (d, J=8.1 Hz, 1H), 7.10 (d, J=5.0 Hz, 1H), 6.70 (s, 2H), 3.60 (s, 2H), 3.47-3.41 (m, 1H), 2.55 (s, 3H), 2.50-2.41 (m, 8H), 2.37 (d, J=5.0 Hz, 3H), 1.31 (d, J=6.8 Hz, 6H).

Example 5: Preparation of 3-((4-amino-7-ethyl-7H-pyrrolo[2,3-d]pyrimidin-5-yl)ethynyl)-4-methyl-N-(4-((4-methylpiperazin-1-yl)methyl)-3-(trifluoromethyl)phenyl)benzamide (Compound I-5)

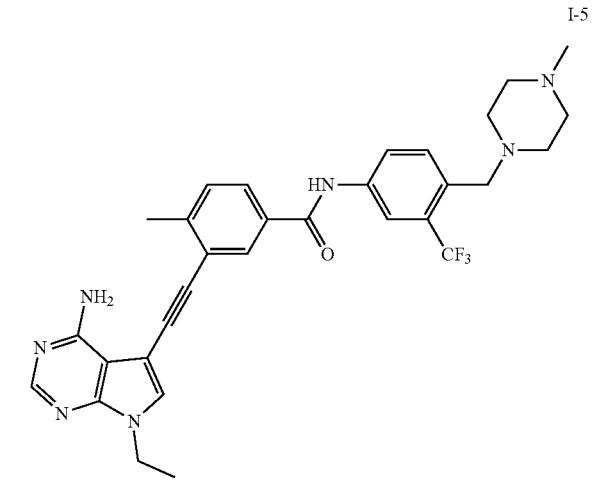 [SMILES: CCn1cc(C#Cc2cc(C(=O)Nc3ccc(CN4CCN(C)CC4)c(C(F)(F)F)c3)ccc2C)c2c(N)ncnc21]

The following route was used for the synthesis:

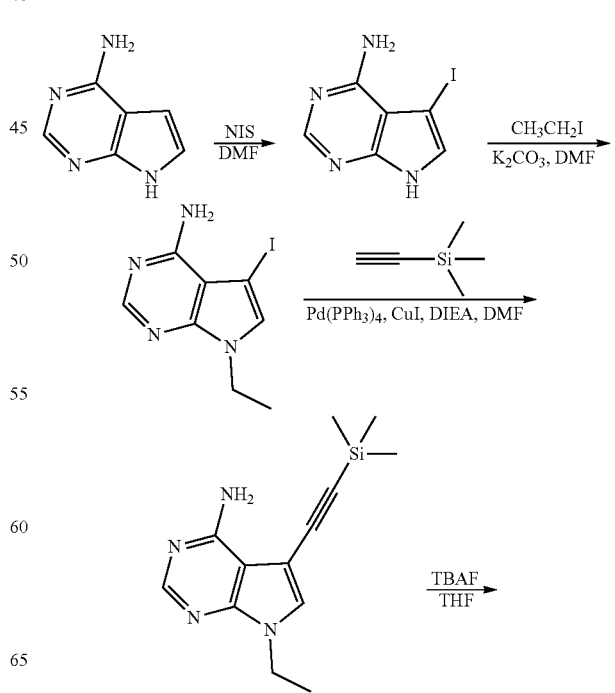

-continued

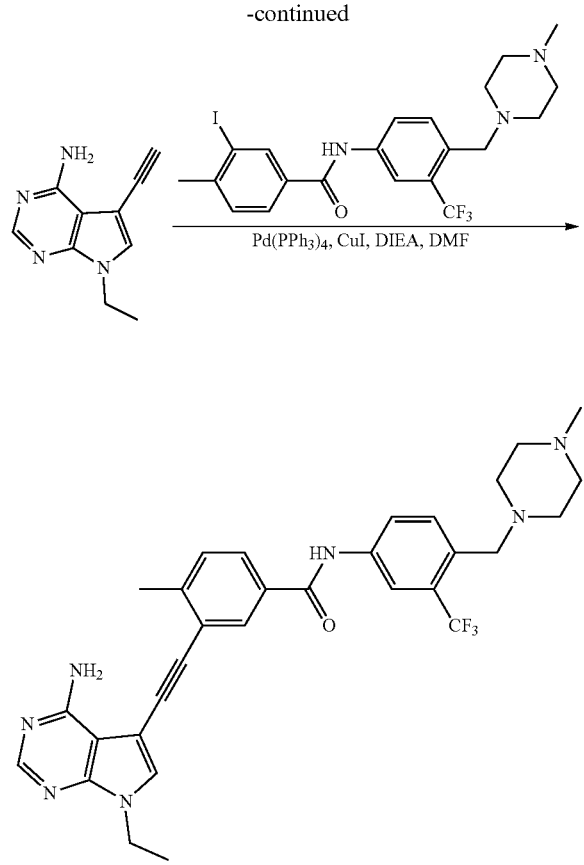

Step 1: Synthesis of compound 5-iodo-7H-pyrrolo[2,3-d]pyrimidin-4-amine 7H-pyrrolo[2,3-d]pyrimidin-4-amine (0.4 g, 3.0 mmol) was dissolved in 10 mL DMF, NIS (0.74 g, 3.3 mmol) was added in batches under an ice bath, the ice bath was removed after the addition, and the reaction was reacted at room temperature for 3 hours. TLC was used to monitor the completion of the reaction. 20 mL of water was added to the reaction solution, which was extracted with ethyl acetate (30 mL*3). The organic phase was washed with 20 mL of saturated brine, dried over anhydrous sodium sulfate, concentrated, and separated by silica gel column to afford 0.56 g of light yellow solid. Yield: 73%. LC-MS(APCI):m/z=261 (M+1)$^+$.

Step 2: Synthesis of compound 7-ethyl-5-iodo-7H-pyrrolo[2,3-d]pyrimidin-4-amine 5-iodo-7H-pyrrolo[2,3-d]pyrimidin-4-amine (0.56 g, 2.2 mmol) and potassium carbonate (0.61 g, 4.4 mmol) were dissolved in 10 mL DMF, ethyl iodide was slowly added (0.37 g, 2.4 mmol) under an ice bath, and the stirring was continued for 30 minutes after the addition. The ice bath was removed, and the reaction was reacted at room temperature for 2 hours. TLC was used to monitor the completion of the reaction, 20 mL of water was added to the reaction solution which was extracted with ethyl acetate (30 mL*3). The organic phase was washed with 20 mL of saturated brine, dried over anhydrous sodium sulfate, concentrated, and separated by silica gel column to afford 0.5 g of light yellow solid. Yield: 80%. LC-MS(APCI):m/z=289(M+1)$^+$.

Step 3: Synthesis of compound 7-ethyl-5-((trimethylsilyeethynyl)-7H-pyrrolo[2,3-d]pyrimidin-4-amine 7-ethyl-5-iodo-7H-pyrrolo[2,3-d]pyrimidin-4-amine (190 mg, 0.66 mmol), trimethylsilylacetylene (84 mg, 0.86 mmol), Pd(PPh$_3$)$_4$ (23 mg, 0.02 mmol), CuI (8 mg, 0.04 mmol) and 0.24 mL N,N-diisopropylethylamine were added into 5 mL DMF, the atmosphere was replaced with nitrogen for 3 times, and the reaction was heated to 90° C. and reacted for 3 hours. After the completion of reaction, the reaction was cooled to room temperature, added with 15 mL of water, and extracted with ethyl acetate (15 mL*3). The organic phase was washed with 10 mL saturated brine, dried over anhydrous sodium sulfate, concentrated, and separated by silica gel column to afford 120 mg of light yellow solid. Yield: 70%. LC-MS(APCI):m/z=259(M+1)$^+$.

Step 4: Synthesis of compound 7-ethyl-5-ethynyl-7H-pyrrolo[2,3-d]pyrimidin-4-amine 7-ethyl-5-((trimethylsilyeethynyl)-7H-pyrrolo[2,3-d]pyrimidin-4-amine (120 mg, 0.47 mmol) was dissolved in 5 mL tetrahydrofuran, tetrabutylammonium fluoride (0.25 g, 0.94 mmol) was added, and the reaction was stirred at room temperature for 1 hour. The solvent was removed by rotary evaporation, 10 mL water was added to the reaction solution, which was extracted with ethyl acetate (10 mL*3). The organic phase was washed with 10 mL saturated brine, dried over anhydrous sodium sulfate, concentrated, and separated by silica gel column to afford 75 mg of light yellow solid. Yield: 88%. LC-MS(APCI):m/z=187(M+1)$^+$.

Step 5: Synthesis of compound 3-((4-amino-7-ethyl-7H-pyrrolo[2,3-d]pyrimidin-5-yl)ethynyl)-4-methyl-N-(4-((4-methylpiperazin-1-yl)methyl)-3-(trifluoromethyl)phenyl)benzamide 3-iodo-4-methyl-N-(4-((4-methylpiperazin-1-yl)methyl)-3-(trifluoromethyl)phenyl)benzamide (160 mg, 0.31 mmol) and 7-ethyl-5-ethynyl-7H-pyrrolo[2,3-d]pyrimidin-4-amine (75 mg, 0.4 mmol), Pd(PPh$_3$)$_4$ (11 mg, 0.01 mmol), CuI (4 mg, 0.02 mmol) and 0.12 mL N,N-diisopropylethylamine were added into 3 mL DMF, the atmosphere was replaced with nitrogen for 3 times, and the reaction was heated to 90° C. and reacted for 3 hours. After the completion of reaction, the reaction was cooled to room temperature, added with 10 mL water, and extracted with ethyl acetate (10 mL*3). The organic phase was washed with 10 mL saturated brine, dried over anhydrous sodium sulfate, concentrated, and separated by silica gel column to afford 115 mg of light yellow solid. Yield: 66%. LC-MS(APCI):m/z=576(M+1)$^+$. 1H NMR (400 MHz, DMSO-d$_6$) δ 10.55 (s, 1H), 8.22 (d, J=2.2 Hz, 1H), 8.17 (d, J=1.8 Hz, 2H), 8.07 (d, J=8.6 Hz, 1H), 7.88 (dd, J=7.9, 1.9 Hz, 1H), 7.79 (s, 1H), 7.71 (d, J=8.6 Hz, 1H), 7.50 (d, J=8.0 Hz, 1H), 6.67 (s, 2H), 4.19 (q, J=7.3 Hz, 2H), 3.58 (s, 2H), 2.54 (s, 3H), 2.49-2.36 (m, 8H), 2.27 (s, 3H), 1.37 (t, J=7.2 Hz, 3H).

Example 6: Preparation of 3-((4-amino-7-ethyl-7H-pyrrolo[2,3-d]pyrimidin-5-yl)ethynyl)-4-methyl-N-(3-(trifluoromethyl)phenyl)benzamide (Compound I-6)

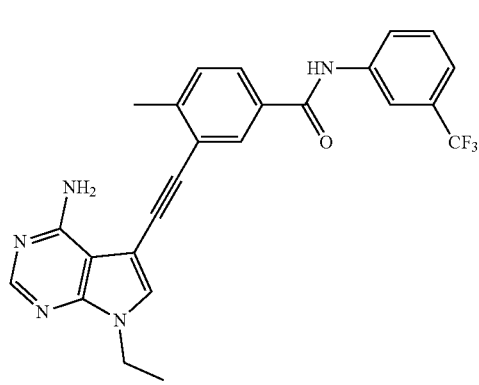

The title compound I-6 was prepared according to the synthetic method described in Example 5, and compound 3-iodo-4-methyl-N-(3-(trifluoromethyl)phenyl)benzamide was used to replace 3-iodo-4-methyl-N-(4-((4-methylpiperazin-1-yl)methyl)-3-(trifluoromethyl)phenyl)benzamide in step 5. LC-MS(APCI):m/z=464(M+1)$^+$. 1H NMR (400 MHz, DMSO-d$_6$) δ 10.58 (s, 1H), 8.26 (s, 1H), 8.20-8.14 (m, 2H), 8.08 (d, J=8.0 Hz, 1H), 7.89 (dd, J=8.0, 2.0 Hz, 1H), 7.79 (s, 1H), 7.61 (t, J=8.0 Hz, 1H), 7.48 (dd, J=16.7, 7.9 Hz, 2H), 6.68 (s, 2H), 4.19 (q, J=7.3 Hz, 2H), 2.54 (s, 3H), 1.37 (t, J=7.2 Hz, 3H).

Example 7: Preparation of 3-((4-amino-7-ethyl-7H-pyrrolo[2,3-d]pyrimidin-5-yl)ethynyl)-4-methyl-N-(6-(trifluoromethyl)pyridin-2-yl)benzamide (Compound I-7)

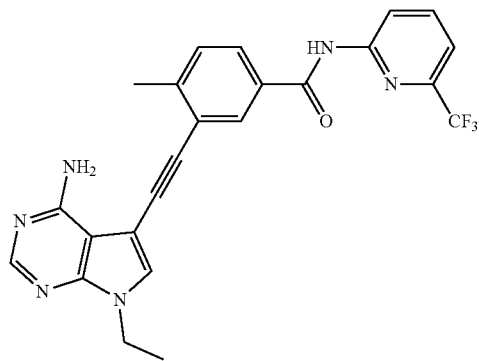

The title compound I-7 was prepared according to the synthetic method described in Example 5, and compound 3-iodo-4-methyl-N-(6-(trifluoromethyl)pyridin-2-yl)benzamide was used to replace 3-iodo-4-methyl-N-(4-((4-methylpiperazin-1-yl)methyl)-3-(trifluoromethyl)phenyl)benzamide in step 5. LC-MS(APCI):m/z=465(M+1)$^+$. 1H NMR (400 MHz, DMSO-d$_6$) δ 11.24 (s, 1H), 8.46 (d, J=8.5 Hz, 1H), 8.26 (d, J=1.9 Hz, 1H), 8.19-8.10 (m, 2H), 7.94 (dd, J=8.0, 1.9 Hz, 1H), 7.79 (s, 1H), 7.66 (d, J=7.5 Hz, 1H), 7.46 (d, J=8.1 Hz, 1H), 6.67 (s, 2H), 4.19 (q, J=7.3 Hz, 2H), 2.53 (s, 3H), 1.37 (t, J=7.2 Hz, 3H).

Example 8: Preparation of 3-((4-amino-7-ethyl-7H-pyrrolo[2,3-d]pyrimidin-5-yl)ethynyl)-N-(3-(trifluoromethyl)phenyl)benzamide (Compound I-8)

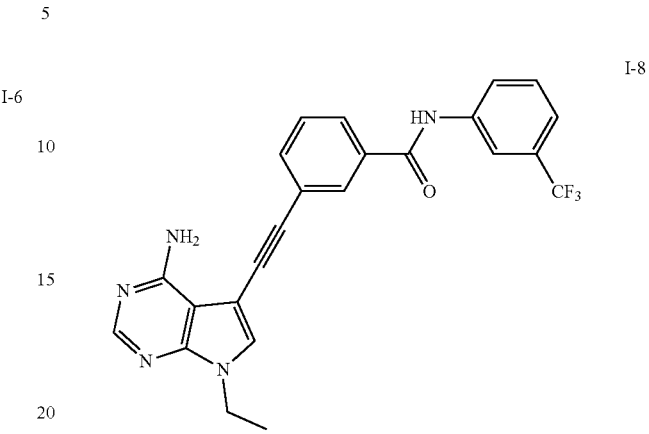

The title compound I-8 was prepared according to the synthetic method described in Example 5, and compound 3-iodo-N-(3-(trifluoromethyl)phenyl)benzamide was used to replace 3-iodo-4-methyl-N-(4-((4-methylpiperazin-1-yl)methyl)-3-(trifluoromethyl)phenyl)benzamide in step 5. LC-MS(APCI):m/z=450(M+1)$^+$. 1H NMR (400 MHz, DMSO-d$_6$) δ 10.55 (s, 1H), 8.25 (s, 1H), 8.21-8.16 (m, 2H), 8.10 (d, J=8.0 Hz, 1H), 7.86 (dd, J=8.0, 2.0 Hz, 1H), 7.77 (s, 1H), 7.61 (d, J=8.0 Hz, 2H), 7.46 (dd, J=16.7, 7.9 Hz, 2H), 6.66 (s, 2H), 4.21 (q, J=7.3 Hz, 2H), 1.35 (t, J=7.2 Hz, 3H).

Example 9: Preparation of 3-((4-amino-7-ethyl-7H-pyrrolo[2,3-d]pyrimidin-5-yl)ethynyl)-N-(4-((dimethylamino)methyl)-3-(trifluoromethyl)phenyl)-4-methylbenzamide (Compound I-9)

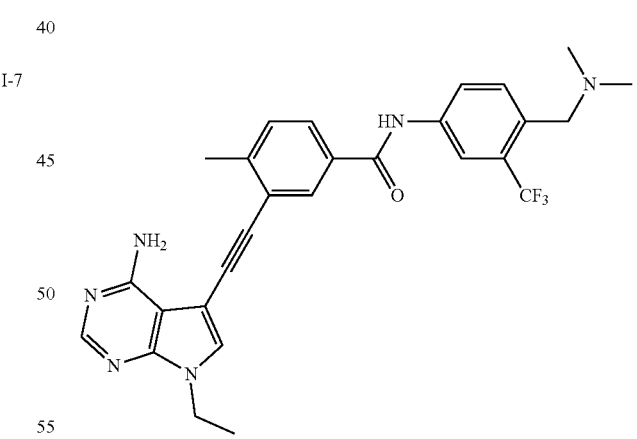

The title compound I-9 was prepared according to the synthetic method described in Example 5, and compound N-(4-((dimethylamino)methyl)-3-(trifluoromethyl)phenyl)-3-iodo-4-methylbenzamide was used to replace 3-iodo-4-methyl-N-(4-((4-methylpiperazin-1-yl)methyl)-3-(trifluoromethyl)phenyl)benzamide in step 5. LC-MS(APCI):m/z=521(M+1)$^+$. 1H NMR (400 MHz, DMSO-d$_6$) δ 10.54 (s, 1H), 8.24-8.14 (m, 3H), 8.08 (d, J=8.5 Hz, 1H), 7.88 (d, J=8.0 Hz, 1H), 7.79 (s, 1H), 7.71 (d, J=8.7 Hz, 1H), 7.50 (d, J=8.1 Hz, 1H), 6.67 (s, 2H), 4.19 (q, J=7.5 Hz, 2H), 3.51 (s, 2H), 2.54 (s, 3H), 2.19 (s, 6H), 1.37 (t, J=7.2 Hz, 3H).

Example 10: Preparation of 3-((4-amino-7-ethyl-7H-pyrrolo[2,3-d]pyrimidin-5-yl)ethynyl)-4-methyl-N-(3-(4-methyl-1H-imidazol-1-yl)-5-(trifluoromethyl)phenyl)benzamide (Compound I-10)

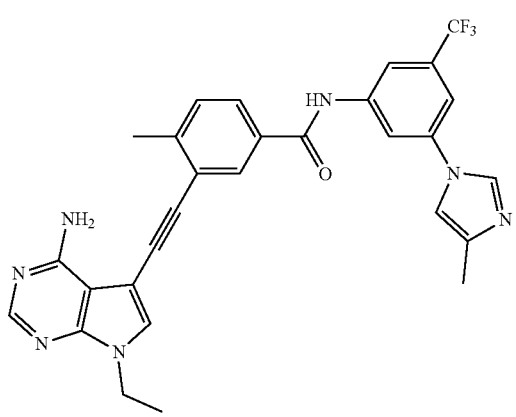

The title compound I-10 was prepared according to the synthetic method described in Example 5, and compound 3-iodo-4-methyl-N-(3-(4-methyl-1H-imidazol-1-yl)-5-(trifluoromethyl)phenyl)benzamide was used to replace 3-iodo-4-methyl-N-(4-((4-methylpiperazin-1-yl)methyl)-3-(trifluoromethyl)phenyl)benzamide in step 5. LC-MS(APCI):m/z=544(M+1)$^+$. 1H NMR (400 MHz, DMSO-d$_6$) δ 10.72 (s, 1H), 8.30 (s, 1H), 8.25 (d, J=1.9 Hz, 1H), 8.20-8.15 (m, 3H), 7.90 (dd, J=7.9, 1.9 Hz, 1H), 7.79 (s, 1H), 7.74 (s, 1H), 7.53 (d, J=8.1 Hz, 2H), 6.66 (s, 2H), 4.19 (q, J=7.2 Hz, 2H), 2.55 (s, 3H), 2.18 (s, 3H), 1.37 (t, J=7.2 Hz, 3H).

Example 11: Preparation of 3-((4-amino-7-methyl-7H-pyrrolo[2,3-d]pyrimidin-5-yl)ethynyl)-4-methyl-N-(3-(4-methyl-1H-imidazol-1-yl)-5-(trifluoromethyl)phenyl)benzamide (Compound I-11)

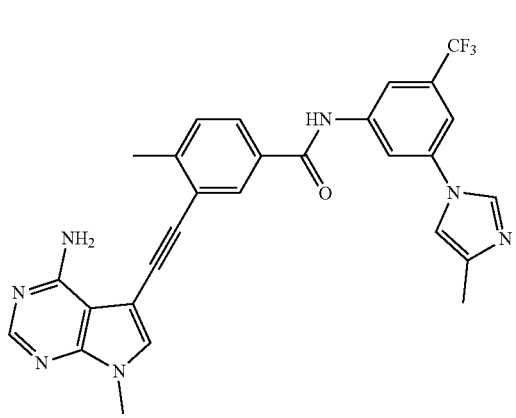

The title compound I-11 was prepared according to the synthetic method described in Example 5, and compound iodomethane was used to replace iodoethane in step 2, compound 3-iodo-4-methyl-N-(3-(4-methyl-1H-imidazol-1-yl)-5-(trifluoromethyl)phenyl)benzamide was used to replace 3-iodo-4-methyl-N-(4-((4-methylpiperazin-1-yl)methyl)-3-(trifluoromethyl)phenyl)benzamide in step 5. LC-MS(APCI):m/z=530(M+1)$^+$. 1H NMR (400 MHz, DMSO-d$_6$) δ 10.72 (s, 1H), 8.31 (s, 1H), 8.25-8.19 (m, 2H), 8.17 (d, J=2.7 Hz, 2H), 7.91 (dd, J=8.0, 2.0 Hz, 1H), 7.79 (s, 1H), 7.74 (s, 1H), 7.53 (d, J=8.2 Hz, 2H), 6.69 (s, 2H), 3.74 (s, 3H), 2.55 (s, 3H), 2.19 (s, 3H).

Example 12: Preparation of 3-((4-amino-7-isopropyl-7H-pyrrolo[2,3-d]pyrimidin-5-yl)ethynyl)-4-methyl-N-(3-(4-methyl-1H-imidazol-1-yl)-5-(trifluoromethyl)phenyl)benzamide (Compound I-12)

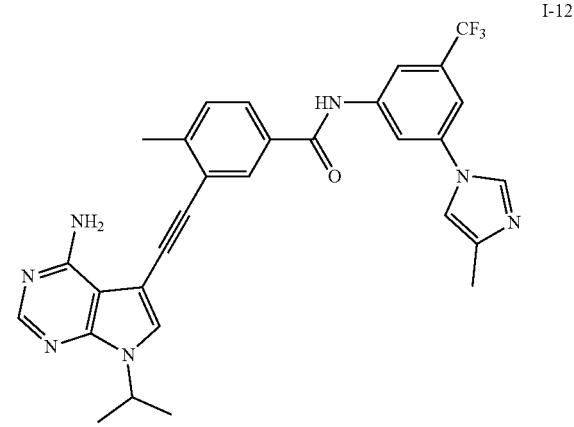 [SMILES: Cc1cn(-c2cc(NC(=O)c3ccc(C)c(C#Cc4cn(C(C)C)c5ncnc(N)c45)c3)cc(C(F)(F)F)c2)cn1]

The title compound I-12 was prepared according to the synthetic method described in Example 5, and compound 2-iodopropane was used to replace iodoethane in step 2, compound 3-iodo-4-methyl-N-(3-(4-methyl-1H-imidazol-1-yl)-5-(trifluoromethyl)phenyl)benzamide was used to replace 3-iodo-4-methyl-N-(4-((4-methylpiperazin-1-yl)methyl)-3-(trifluoromethyl)phenyl)benzamide in step 5. LC-MS(APCI):m/z=558(M+1)$^+$. 1H NMR (400 MHz, DMSO-d$_6$) δ 10.73 (s, 1H), 8.31 (d, J=2.3 Hz, 1H), 8.22 (d, J=1.4 Hz, 1H), 8.19 (d, J=1.9 Hz, 1H), 8.17 (d, J=3.6 Hz, 2H), 7.91 (dd, J=8.1, 2.0 Hz, 1H), 7.88 (s, 1H), 7.74 (s, 1H), 7.53 (d, J=8.1 Hz, 1H), 7.51-7.48 (m, 1H), 6.65 (s, 2H), 4.93 (p, J=6.9 Hz, 1H), 2.56 (s, 3H), 2.19 (s, 3H), 1.47 (d, J=6.7 Hz, 6H).

Example 13: Preparation of 3-((4-amino-7-isopropyl-7H-pyrrolo[2,3-d]pyrimidin-5-yl)ethynyl)-4-methyl-N-(3-(trifluoromethyl)phenyl)benzamide (Compound I-13)

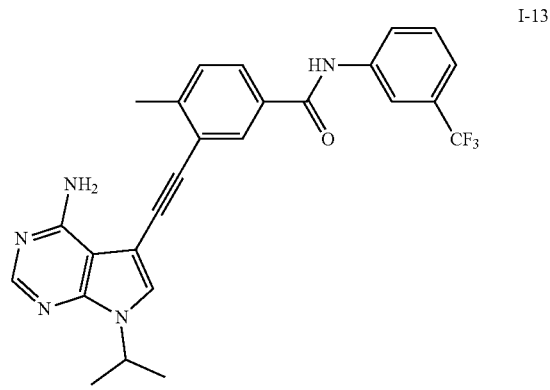 [SMILES: Cc1ccc(C(=O)Nc2cccc(C(F)(F)F)c2)cc1C#Cc1cn(C(C)C)c2ncnc(N)c12]

The title compound I-13 was prepared according to the synthetic method described in Example 5, and compound 2-iodopropane was used to replace iodoethane in step 2, compound 3-iodo-4-methyl-N-(3-(trifluoromethyl)phenyl)benzamide was used to replace 3-iodo-4-methyl-N-(4-((4-methylpiperazin-1-yl)methyl)-3-(trifluoromethyl)phenyl)benzamide in step 5. LC-MS(APCI):m/z=478 (M+1)⁺. 1H NMR (400 MHz, DMSO-d₆) δ 10.58 (s, 1H), 8.26 (t, J=1.9 Hz, 1H), 8.20-8.13 (m, 2H), 8.08 (d, J=8.2 Hz, 1H), 7.89 (d, J=8.8 Hz, 2H), 7.61 (t, J=8.0 Hz, 1H), 7.48 (dd, J=17.4, 7.9 Hz, 2H), 6.65 (s, 2H), 4.93 (p, J=6.8 Hz, 1H), 2.55 (s, 3H), 1.46 (d, J=6.8 Hz, 6H).

Example 14: Preparation of 3-((4-amino-7-methyl-7H-pyrrolo[2,3-d]pyrimidin-5-yl)ethynyl)-4-methyl-N-(3-(trifluoromethyl)phenyl)benzamide (Compound I-14)

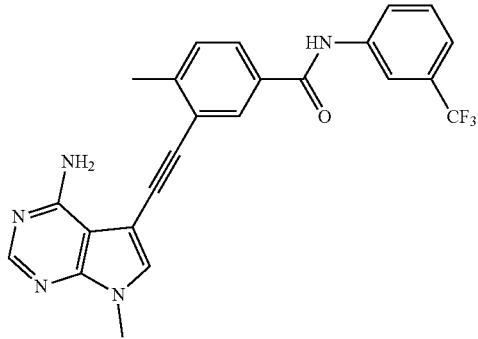

I-14

The title compound I-14 was prepared according to the synthetic method described in Example 5, and compound iodomethane was used to replace iodoethane in step 2, compound 3-iodo-4-methyl-N-(3-(trifluoromethyl)phenyl)benzamide was used to replace 3-iodo-4-methyl-N-(4-((4-methylpiperazin-1-yl)methyl)-3-(trifluoromethyl)phenyl)benzamide in step 5. LC-MS(APCI):m/z=450 (M+1)⁺. 1H NMR (400 MHz, DMSO-d₆) δ10.58 (s, 1H), 8.26 (t, J=1.9 Hz, 1H), 8.18 (d, J=1.9 Hz, 1H), 8.10-8.06 (m, 1H), 7.89 (dd, J=8.0, 2.0 Hz, 1H), 7.71 (s, 1H), 7.61 (t, J=8.0 Hz, 1H), 7.52-7.44 (m, 2H), 6.67 (s, 2H), 3.73 (s, 3H), 2.54 (s, 3H).

Example 15: Preparation of 3-((4-amino-7-isopropyl-7H-pyrrolo[2,3-d]pyrimidin-5-yl)ethynyl)-4-methyl-N-(4-((4-methylpiperazin-1-yl)methyl)-3-(trifluoromethyl)phenyl)benzamide (Compound I-15)

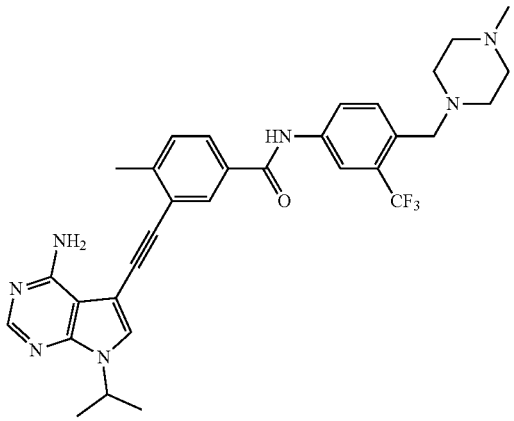

I-15

The title compound I-15 was prepared according to the synthetic method described in Example 5, and compound 2-iodopropane was used to replace iodoethane in step 2. LC-MS(APCI):m/z=590(M+1)⁺. 1H NMR (400 MHz, CDCl₃) δ 8.32 (s, 1H), 8.02-7.95 (m, 2H), 7.89 (d, J=9.0 Hz, 1H), 7.86 (s, 1H), 7.80-7.72 (m, 2H), 7.38 (d, J=8.1 Hz, 2H), 6.65 (s, 2H), 5.06 (s, 1H), 3.65 (s, 2H), 2.57 (d, J=12.9 Hz, 11H), 2.34 (s, 3H), 1.53 (d, J=6.8 Hz, 6H).

Example 16: Preparation of 3-((4-amino-7-methyl-7H-pyrrolo[2,3-d]pyrimidin-5-yl)ethynyl)-4-methyl-N-(4-((4-methyl piperazin-1-yl)methyl)-3-(trifluoromethyl)phenyl)benzamide (Compound I-16)

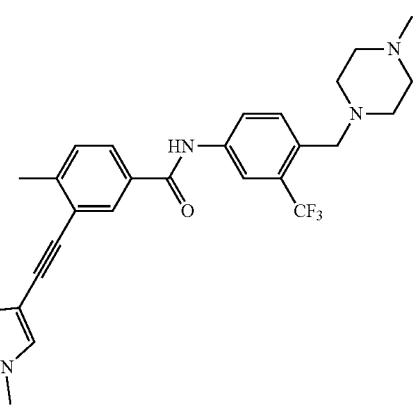

I-16

The title compound I-16 was prepared according to the synthetic method described in Example 5, and compound iodomethane was used to replace iodoethane in step 2.
LC-MS(APCI):m/z=562(M+1)⁺. 1H NMR (400 MHz, DMSO-d₆) δ 10.54 (s, 1H), 8.22 (d, J=2.1 Hz, 1H), 8.17 (d, J=2.0 Hz, 2H), 8.07 (dd, J=8.6, 2.1 Hz, 1H), 7.88 (dd, J=7.9, 1.9 Hz, 1H), 7.73-7.68 (m, 2H), 7.50 (d, J=8.1 Hz, 1H), 6.66 (s, 2H), 3.74 (s, 3H), 3.57 (s, 2H), 2.54 (s, 3H), 2.41 (s, 8H), 2.21 (s, 3H).

Example 17: Preparation of N-(3-((4-amino-7-ethyl-7H-pyrrolo[2,3-d]pyrimidin-5-yl)ethynyl)-4-methylphenyl)-3-(trifluoromethyl)benzamide (Compound I-17)

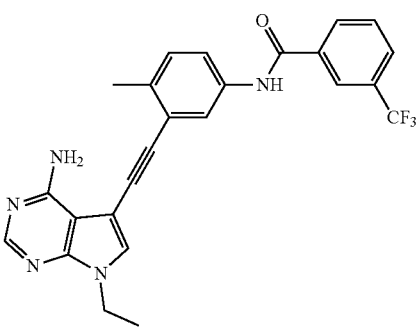

I-17

The title compound I-17 was prepared according to the synthetic method described in Example 5, and compound N-(3-iodo-4-methylphenyl)-3-(trifluoromethyl)benzamide was used to replace 3-iodo-4-methyl-N-(4-((4-methylpiperazin-1-yl)methyl)-3-(trifluoromethyl)phenyl)benzamide in step 5. LC-MS(APCI):m/z=464(M+1)$^+$. 1H NMR (400 MHz, DMSO-d$_6$) δ 10.50 (s, 1H), 8.31 (s, 1H), 8.27 (d, J=7.8 Hz, 1H), 8.16 (s, 1H), 8.00-7.95 (m, 2H), 7.81 (d, J=7.8 Hz, 1H), 7.79-7.77 (m, 1H), 7.68 (dd, J=8.4, 2.2 Hz, 1H), 7.32 (d, J=8.3 Hz, 1H), 6.66 (s, 2H), 4.18 (q, J=7.2 Hz, 2H), 2.44 (s, 3H), 1.40-1.35 (t, J=7.2 Hz, 3H).

Example 18: Preparation of N-(3-((4-amino-7-ethyl-7H-pyrrolo[2,3-d]pyrimidin-5-yl)ethynyl)-4-methylphenyl)-4-((4-methylpiperazin-1-yl)methyl)-3-(trifluoromethyl)benzamide (Compound I-18)

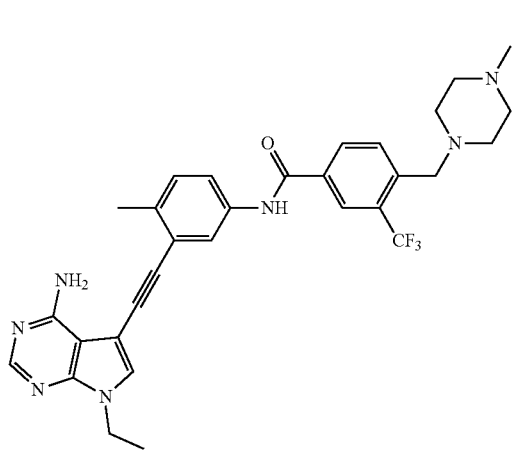

I-18

The title compound I-18 was prepared according to the synthetic method described in Example 5, and compound N-(3-iodo-4-methylphenyl)-4-((4-methylpiperazin-1-yl)methyl)-3-(trifluoromethyl)benzamide was used to replace 3-iodo-4-methyl-N-(4-((4-methylpiperazin-1-yl)methyl)-3-(trifluoromethyl)phenyl)benzamide in step 5. LC-MS (APCI):m/z=576(M+1)$^+$. 1H NMR (400 MHz, DMSO-d$_6$) δ 10.47 (s, 1H), 8.26 (d, J=1.7 Hz, 1H), 8.24 (dd, J=8.1, 1.8 Hz, 1H), 8.16 (s, 1H), 7.96 (d, J=2.3 Hz, 1H), 7.93 (d, J=8.1 Hz, 1H), 7.78 (s, 1H), 7.67 (dd, J=8.3, 2.3 Hz, 1H), 7.31 (d, J=8.5 Hz, 1H), 6.65 (s, 2H), 4.18 (q, J=7.2 Hz, 2H), 3.69 (s, 2H), 2.44 (s, 11H), 2.20 (s, 3H), 1.37 (t, J=7.2 Hz, 3H).

Example 19: Preparation of N-(3-((4-amino-7-methyl-7H-pyrrolo[2,3-d]pyrimidin-5-yl)ethynyl)-4-methylphenyl)-4-((4-methylpiperazin-1-yl)methyl)-3-(trifluoromethyl)benzamide (Compound I-19)

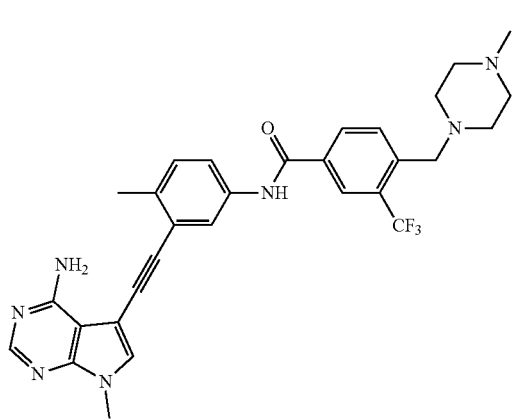

I-19

The title compound I-19 was prepared according to the synthetic method described in Example 5, and compound iodomethane was used to replace iodoethane in step 2, compound N-(3-iodo-4-methylphenyl)-4-((4-methylpiperazin-1-yl)methyl)-3-(trifluoromethyl)benzamide was used to replace 3-iodo-4-methyl-N-(4-((4-methylpiperazin-1-yl)methyl)-3-(trifluoromethyl)phenyl)benzamide in step 5. LC-MS(APCI):m/z=562(M+1)$^+$. 1H NMR (400 MHz, DMSO-d$_6$) δ 10.46 (s, 1H), 8.30-8.21 (m, 2H), 8.17 (s, 1H), 7.99-7.88 (m, 2H), 7.68 (d, J=9.4 Hz, 2H), 7.31 (d, J=8.4 Hz, 1H), 6.64 (s, 2H), 3.71 (d, J=10.1 Hz, 5H), 2.44 (s, 3H), 2.50-2.45 (m, 8H), 2.28 (s, 3H).

Example 20: Preparation of N-(3-((4-amino-7-cyclopentyl-7H-pyrrolo[2,3-d]pyrimidin-5-yl)ethynyl)-4-methylphenyl)-4-methyl-3-(trifluoromethyl)benzamide (Compound I-20)

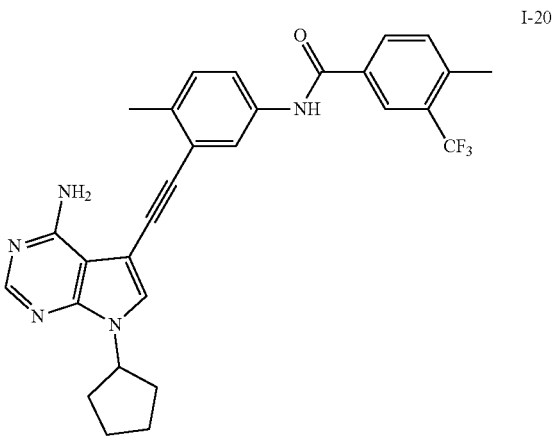 [SMILES: Cc1ccc(NC(=O)c2ccc(C)c(C(F)(F)F)c2)cc1C#Cc1cn(C2CCCC2)c2ncnc(N)c12]

I-20

The title compound I-20 was prepared according to the synthetic method described in Example 5, and compound iodocyclopentane was used to replace iodoethane in step 2, compound N-(3-iodo-4-methylphenyl)-4-methyl-3-(trifluoromethyl)benzamide was used to replace 3-iodo-4-methyl-N-(4-((4-methylpiperazin-1-yl)methyl)-3-(trifluoromethyl)phenyl)benzamide in step 5. LC-MS(APCI):m/z=518(M+1)$^+$. 1H NMR (400 MHz, DMSO-d$_6$) δ 10.43 (s, 1H), 8.26 (s, 1H), 8.16 (s, 2H), 7.98 (d, J=2.2 Hz, 1H), 7.83 (s, 1H), 7.68-7.60 (m, 2H), 7.31 (d, J=8.4 Hz, 1H), 6.66 (s, 2H), 5.03 (p, J=7.5 Hz, 1H), 2.53 (s, 3H), 2.44 (s, 3H), 2.10 (d, J=7.7 Hz, 2H), 1.88 (p, J=9.1, 8.6 Hz, 4H), 1.68 (s, 2H).

Example 21: Preparation of N-(3-((4-amino-7-ethyl-7H-pyrrolo[2,3-d]pyrimidin-5-yl)ethynyl)-4-methylphenyl)-3-(4-methyl-1H-imidazol-1-yl)-5-(trifluoromethyl)benzamide (Compound I-21)

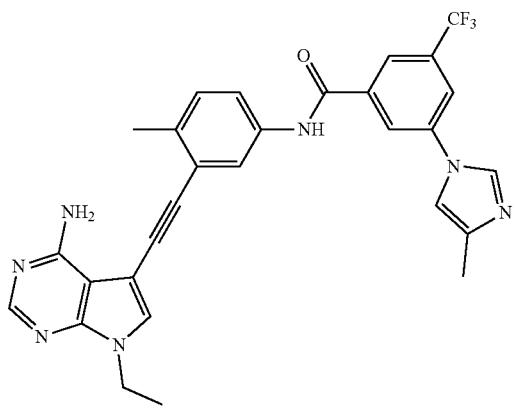

I-21

The title compound I-21 was prepared according to the synthetic method described in Example 5, and compound N-(3-iodo-4-methylphenyl)-3-(4-methyl-1H-imidazol-1-yl)-5-(trifluoromethyl)benzamide was used to replace 3-iodo-4-methyl-N-(4-((4-methylpiperazin-1-yl)methyl)-3-(trifluoromethyl)phenyl)benzamide in step 5. LC-MS (APCI):m/z=544(M+1)$^+$. 1H NMR (400 MHz, DMSO-d$_6$) δ 10.73 (s, 1H), 8.29 (s, 1H), 8.24 (d, J=1.9 Hz, 1H), 8.20-8.15 (m, 3H), 7.92 (dd, J=7.9, 1.9 Hz, 1H), 7.78 (s, 1H), 7.73 (s, 1H), 7.51 (d, J=8.1 Hz, 2H), 6.67 (s, 2H), 4.18 (q, J=7.2 Hz, 2H), 2.54 (s, 3H), 2.18 (s, 3H), 1.36 (t, J=7.2 Hz, 3H).

Example 22: Preparation of 3-((4-amino-7-((1r,4r)-4-hydroxycyclohexyl)-7H-pyrrolo[2,3-d]pyrimidin-5-yl)ethynyl)-4-methyl-N-(4-((4-methylpiperazin-1-yl)methyl)-3-(trifluoromethyl)phenyl)benzamide (Compound I-22)

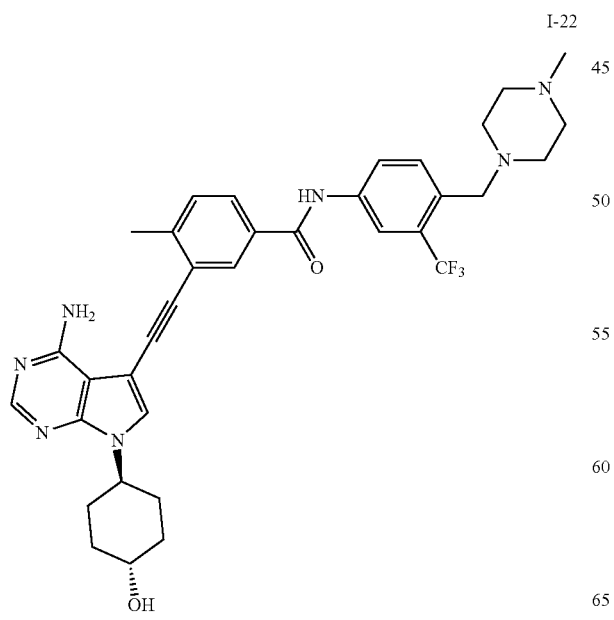

I-22

The following route was used for the synthesis:

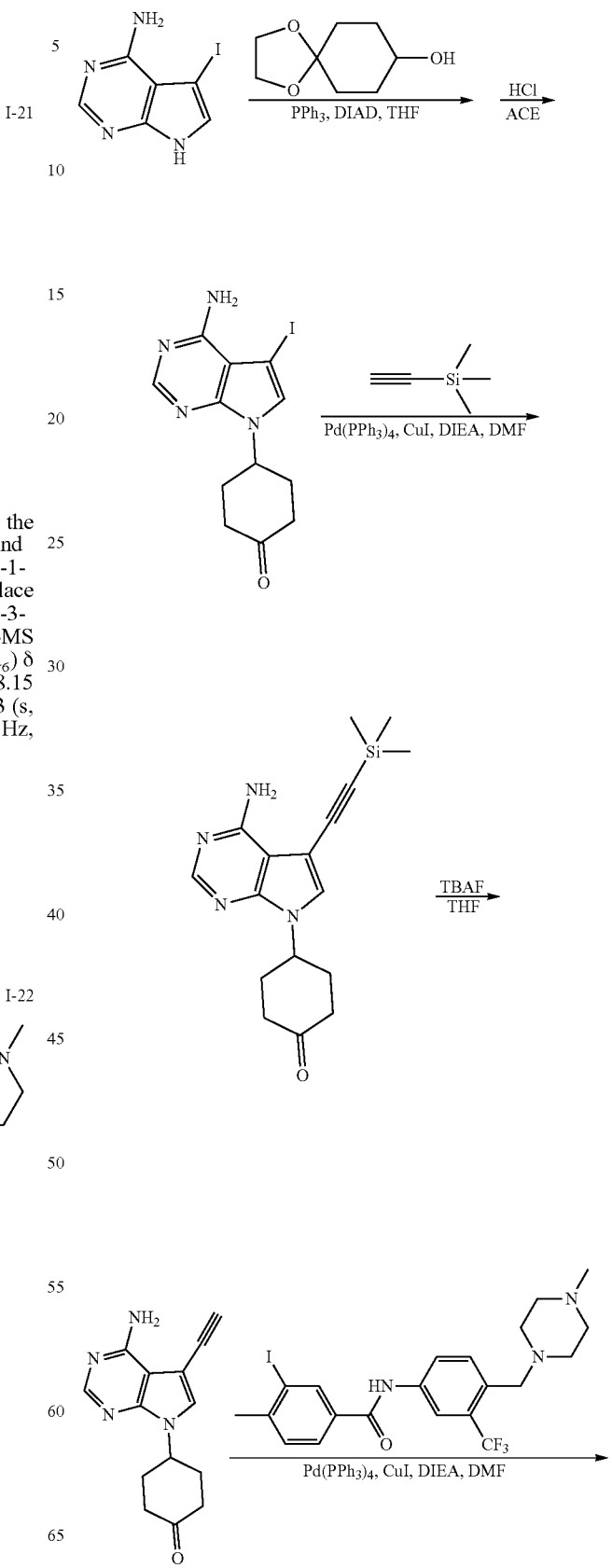

-continued

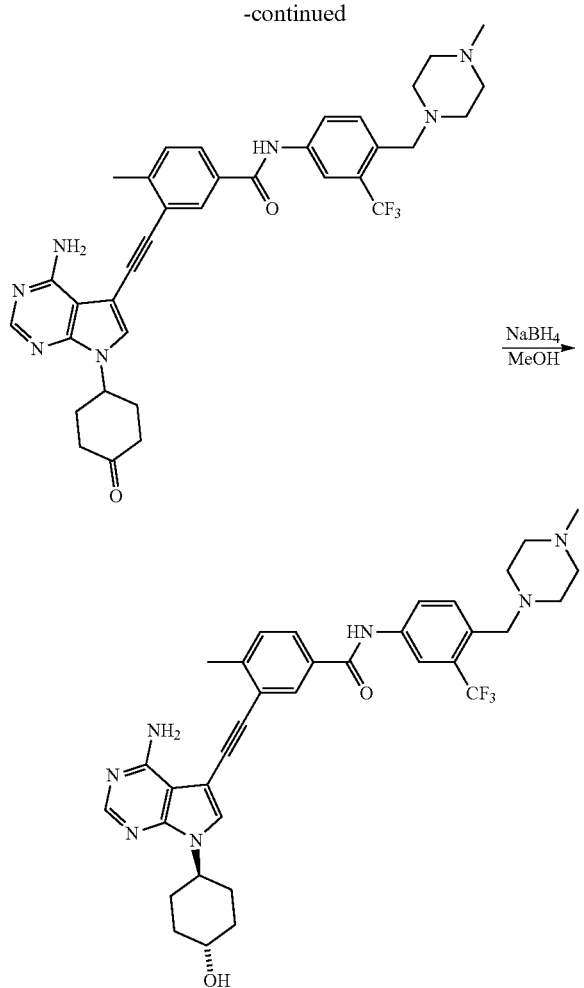

Step 1: Synthesis of compound 4-(4-amino-5-iodo-7H-pyrrolo[2,3-d]pyrimidin-7-yl)cyclohexane-1-one 5-iodo-7H-pyrrolo[2,3-d]pyrimidin-4-amine (1.34 g, 5.15 mmol), 4-hydroxycyclohexanone ethylene acetal (1.22 g, 7.7 mmol) and triphenylphosphine (4.05 g, 15.45 mmol) were added to 30 mL anhydrous tetrahydrofuran, the reaction was protected by nitrogen, diisopropyl azodicarboxylate (2.1 g, 10.3 mmol) was slowly added dropwise under an ice bath, and after the addition, the reaction was naturally warmed to room temperature and reacted overnight. TLC was used to monitor the completion of the reaction. The solvent was removed by rotary evaporation, 20 mL ethyl acetate was added, the reaction was stirred at room temperature for 0.5 hours, which was filtered, the filter cake was rinsed with 5 mL ethyl acetate, and dried to afford 1.5 g of white solid. 20 mL of acetone was added to dissolve the solid, to which 6M hydrochloric acid was slowly added under an ice bath until pH=3, and the reaction solution was reacted at room temperature for 3 hours. The solvent was removed by rotary evaporation, ethyl acetate was added to dissolve the residue, the solution was washed with saturated sodium bicarbonate solution, dried, and concentrated to afford 1.1 g of white solid. Yield: 60%. LC-MS(APCI):m/z=357(M+1)+.

Step 2: Synthesis of compound 4-(4-amino-5-((trimethylsilyl)ethynyl)-7H-pyrrolo[2,3-d]pyrimidin-7-yl)cyclohexane-1-one 4-(4-amino-5-iodo-7H-pyrrolo[2,3-d]pyrimidin-7-yl)cyclohexane-1-one (0.55 g, 1.54 mmol), trimethylsilylacetylene (0.2 g, 2.0 mmol), Pd(PPh$_3$)$_4$ (58 mg, 0.05 mmol), CuI (19 mg, 0.1 mmol) and 0.4 mL N,N-diisopropylethylamine were added into 10 mL DMF, the atmosphere was replaced with nitrogen for 3 times, and the reaction was heated to 90° C. and reacted for 3 hours. After the completion of reaction, the reaction was cooled to room temperature, added with 20 mL of water, and extracted with ethyl acetate (20 mL*3). The organic phase was washed with 15 mL of saturated brine, dried over anhydrous sodium sulfate, concentrated, and separated by silica gel column to afford 0.33 g of light yellow solid. Yield: 66%. LC-MS (APCI):m/z=327(M+1)+.

Step 3: Synthesis of compound 4-(4-amino-5-ethynyl-7H-pyrrolo[2,3-d]pyrimidin-7-yl)cyclohexane-1-one 4-(4-amino-5-((trimethylsilyl)ethynyl)-7H-pyrrolo[2,3-d]pyrimidin-7-yl)cyclohexane-1-one (0.33 g, 1.0 mmol) was dissolved in 5 mL tetrahydrofuran, tetrabutylammonium fluoride (0.52 g, 2.0 mmol) was added, and stirred at room temperature for 1 hour. The solvent was removed by rotary evaporation, 10 mL water was added to the reaction solution, which was extracted with ethyl acetate (10 mL*3) The organic phase was washed with 10 mL saturated brine, dried over anhydrous sodium sulfate, concentrated, and separated by silica gel column to afford 224 mg of pale yellow solid. Yield: 88%. LC-MS(APCI):m/z=255(M+1)+.

Step 4: Synthesis of compound 3-((4-amino-7-(4-oxocyclohexyl)-7H-pyrrolo[2,3-d]pyrimidin-5-yl)ethynyl)-4-methyl-N-(4-((4-methylpiperazin-1-yl)methyl)-3-(trifluoromethyl)phenyl)benzamide 3-iodo-4-methyl-N-(4-((4-methylpiperazin-1-yl)methyl)-(3-(trifluoromethyl)phenyl)benzamide (224 mg, 0.43 mmol) and 4-(4-amino-5-ethynyl-7H-pyrrolo[2,3-d]pyrimidin-7-yl)cyclohexane-1-one (142 mg, 0.56 mmol), Pd(PPh$_3$)$_4$ (16 mg, 0.01 mmol), CuI (5 mg, 0.02 mmol) and 0.12 mL N,N-diisopropylethylamine were added into 5 mL DMF, the atmosphere was replaced with nitrogen for 3 times, and the reaction was heated to 90° C. and reacted for 3 hours. After the completion of reaction, the reaction was cooled to room temperature, added with 15 mL water, and extracted with ethyl acetate (15 mL*3). The organic phase was washed with 10 mL of saturated brine, dried over anhydrous sodium sulfate, concentrated, and separated by silica gel column to obtain 184 mg of light yellow solid. Yield: 66%. LC-MS (APCI):m/z=644(M+1)+.

Step 5: Synthesis of compound 3-((4-amino-7-((1r,4r)-4-hydroxycyclohexyl)-7H-pyrrolo[2,3-d]pyrimidin-5-yl)ethynyl)-4-methyl-N-(4-((4-methylpiperazin-1-yl)methyl)-3-(trifluoromethyl)phenyl)benzamide 3-((4-amino-7-(4-oxocyclohexyl)-7H-pyrrolo[2,3-d]pyrimidin-5-yl)ethynyl)-4-methyl-N-(4-((4-methylpiperazin-1-yl)methyl)-3-(trifluoromethyl)phenyl)benzamide (184 mg, 0.28 mmol) was dissolved in 10 mL methanol, sodium borohydride (32 mg, 0.84 mmol) was slowly added under an ice bath, the reaction was naturally warmed to room temperature and reacted for 1 hour. TLC was used to monitor the completion of the reaction. 10 mL water was added to the reaction solution, which was extracted with ethyl acetate (10 mL*3). The organic phase was washed with 10 mL saturated brine, dried over anhydrous sodium sulfate, concentrated, and separated by silica gel column to afford 120 mg of light yellow solid. Yield: 65%. LC-MS(APCI):m/z=646(M+1)$^+$. 1H NMR (400 MHz, DMSO-d$_6$) δ 10.59 (s, 1H), 8.23 (s, 1H), 8.16 (d, J=6.6 Hz, 2H), 8.09 (d, J=8.7 Hz, 1H), 7.90 (d, J=8.1 Hz, 1H), 7.84 (s, 1H), 7.71 (d, J=8.6 Hz, 1H), 7.49 (d, J=8.1 Hz, 1H), 6.65 (s, 2H), 4.70 (d, J=4.2 Hz, 1H), 4.52 (s, 1H), 3.61 (s, 2H), 3.54 (s, 1H), 2.54 (s, 3H), 2.50-2.44 (s, 8H), 2.39 (s, 3H), 2.00-1.86 (m, 6H), 1.39 (s, 2H).

Example 23: Preparation of 3-((4-amino-7-((1r,4r)-4-hydroxycyclohexyl)-7H-pyrrolo[2,3-d]pyrimidin-5-yl)ethynyl)-4-methyl-N-(3-(trifluoromethyl)phenyl)benzamide (Compound I-23)

The title compound I-23 was prepared according to the synthetic method described in Example 22, and compound 3-iodo-4-methyl-N-(3-(trifluoromethyl)phenyl)benzamide was used to replace 3-iodo-4-methyl-N-(4-((4-methylpiperazin-1-yl)methyl)-(3-(trifluoromethyl)phenyl)benzamide in step 4. LC-MS(APCI):m/z=534(M+1)$^+$. 1H NMR (400 MHz, DMSO-d$_6$) δ 10.40 (s, 1H), 8.22 (s, 1H), 8.16 (d, J=7.9 Hz, 2H), 7.93 (d, J=2.3 Hz, 1H), 7.82 (s, 1H), 7.66-7.60 (m, 2H), 7.55 (s, 1H), 7.33 (s, 1H), 6.65 (s, 2H), 4.70 (d, J=4.4 Hz, 1H), 4.53 (dd, J=10.8, 5.9 Hz, 1H), 3.54 (d, J=4.4 Hz, 1H), 2.53 (s, 3H), 1.97-1.86 (m, 6H), 1.38 (s, 2H).

Example 24: Preparation of 3-((4-amino-7-((1r,4r)-4-hydroxycyclohexyl)-7H-pyrrolo[2,3-d]pyrimidin-5-yl)ethynyl)-4-methyl-N-(4-methyl-3-(trifluoromethyl)phenyl)benzamide (Compound I-24)

The title compound I-24 was prepared according to the synthetic method described in Example 22, and compound 3-iodo-4-methyl-N-(4-methyl-3-(trifluoromethyl)phenyl)benzamide was used to replace 3-iodo-4-methyl-N-(4-((4-methylpiperazin-1-yl)methyl)-(3-(trifluoromethyl)phenyl)benzamide in step 4. LC-MS(APCI):m/z=548(M+1)$^+$. 1H NMR (400 MHz, DMSO-d$_6$) δ 10.42 (s, 1H), 8.26 (s, 1H), 8.16 (d, J=7.9 Hz, 2H), 7.96 (d, J=2.3 Hz, 1H), 7.83 (s, 1H), 7.68-7.61 (m, 2H), 7.31 (d, J=8.4 Hz, 1H), 6.66 (s, 2H), 4.68 (d, J=4.4 Hz, 1H), 4.51 (dd, J=10.8, 5.9 Hz, 1H), 3.53 (d, J=4.4 Hz, 1H), 2.53 (s, 3H), 2.44 (s, 3H), 1.99-1.86 (m, 6H), 1.39 (s, 2H).

Example 25: Preparation of N-(3-((4-amino-7-((1r,4r)-4-hydroxycyclohexyl)-7H-pyrrolo[2,3-d]pyrimidin-5-yl)ethynyl)-4-methylphenyl)-4-((4-methylpiperazin-1-yl)methyl)-3-(trifluoromethyl)benzamide (Compound I-25)

The title compound 1-25 was prepared according to the synthetic method described in Example 22, and compound N-(3-iodo-4-methylphenyl)-4-((4-methylpiperazin-1-yl)methyl)-3-(trifluoromethyl)benzamide was used to replace 3-iodo-4-methyl-N-(4-((4-methylpiperazin-1-yl)methyl)-(3-(trifluoromethyl)phenyl)benzamide in step 4. LC-MS (APCI):m/z=646(M+1)$^+$. 1H NMR (400 MHz, DMSO-d$_6$) δ 10.32 (s, 1H), 8.22 (s, 1H), 8.18 (d, J=6.6 Hz, 2H), 8.12 (d, J=8.7 Hz, 1H), 7.93 (d, J=8.1 Hz, 1H), 7.82 (s, 1H), 7.70 (d, J=8.6 Hz, 1H), 7.44 (d, J=8.1 Hz, 1H), 6.66 (s, 2H), 4.73 (d, J=4.2 Hz, 1H), 4.53 (s, 1H), 3.64 (s, 2H), 3.54 (s, 1H), 2.53 (s, 3H), 2.49-2.43 (s, 8H), 2.38 (s, 3H), 1.97-1.85 (m, 6H), 1.38 (s, 2H).

Biological Activity Assay

Biological Example 1: Biochemical Kinase Analysis

Reagents and materials: ABL (ThermoFisher, Cat. No PV3585), ABL$^{T315I}$ (Thermo Fisher, Cat. No. PR7429B), ATP (Sigma, Cat. No. A7699-1G), DMSO (Sigma, Cat. No. D2650), 96-well plate (Corning, Cat. No. 3365), 384-well plate (Greiner, Cat. No. 784076), buffer solution (Thermo Fisher, Cat. No. PR4876B).

Specific Assay Method:

Compound formulation: The test compounds were dissolved in DMSO to prepare a 20 mM stock solution. Before use, the compounds were diluted in DMSO to 0.1 mM, and diluted into 11 concentrations with a 3-fold gradient. When addition, diluentions of 4-fold final concentration were then made with buffer solution.

Kinase assay method: After preparing the buffer, the enzyme was mixed with pre-formulated and diluted compounds of different concentrations in duplicate for each concentration, and placed at room temperature for 30 minutes. The corresponding substrate and ATP were added thereto, and reacted at room temperature for 60 minutes (both a negative and a positive control were set). After the reaction, antibody was added for detection, Envision detection was carried out after 60 minutes incubation at room temperature, and data was collected. Data analysis and fitting were made according to XLfit5 software, wherein, A represents IC$_{50}$≤5 nM, B represents IC$_{50}$ is 5-50 nM, C represents IC$_{50}$ is 50-100 nM, D represents IC$_{50}$>100 nM.

Compounds of the present disclosure were tested in the above kinase inhibition assay, and it is found that the compounds of the present disclosure have potent activity against ABL and ABL$^{T315I}$. Results of representative example compounds were summarized in Table 1 below:

TABLE 1

| Example No. | ABL IC$_{50}$ (nM) | ABL$^{T315I}$IC$_{50}$ (nM) |
|---|---|---|
| Example 1 | A | A |
| Example 2 | B | C |
| Example 3 | A | A |
| Example 4 | A | A |
| Example 5 | A | A |
| Example 6 | A | A |
| Example 7 | A | B |
| Example 8 | A | A |
| Example 9 | A | A |
| Example 10 | B | B |
| Example 11 | A | B |
| Example 12 | B | B |
| Example 13 | B | B |
| Example 14 | A | A |
| Example 15 | A | A |

TABLE 1-continued

| Example No. | ABL IC$_{50}$ (nM) | ABL$^{T315I}$IC$_{50}$ (nM) |
|---|---|---|
| Example 16 | A | A |
| Example 17 | A | A |
| Example 18 | A | A |
| Example 19 | A | A |
| Example 20 | B | C |
| Example 21 | A | B |
| Example 22 | A | A |
| Example 23 | A | B |
| Example 24 | A | B |
| Example 25 | A | A |

Biological Example 2: Cell Proliferation Analysis

The inhibitory effect of the example compounds on Ba/F3, Ba/F3 Bcr-Abl T315I cell activity was determined.

Materials and reagents: RPMI-1640 medium (GIBCO, Catalog No. A10491-01), fetal bovine serum (GIBCO, Catalog No. 10099141), antibiotics (Penicillin-Streptomycin), IL-3 (PeproTech), promycin; cell lines: Ba/F3, Ba/F3 Bcr-Abl T315I (Purchased from American type culture collection, ATCC), live cell detection kit CellTiter-Glo4 (Promega, Catalog No. G7572), 96-well black wall transparent flat bottom cell culture plate (Corning, Catalog No. 3340).

Test method: 1. Preparation of cell plate: Ba/F3, Ba/F3 Bcr-Abl T315I cells were respectively seeded in 96-well plates, and 8 ng/ml IL-3 was added to the Ba/F3 cells, and the cell plates were placed in a carbon dioxide incubator and cultured overnight. 2. The test compounds were dissolved in DMSO, 9 compound concentrations were made with a 3.16-fold gradient dilution in triplicate. 3. Treatment of the cells with compounds: The compounds were transferred to the cell plate with a starting concentration of 10 μM. The cell plate was placed in a carbon dioxide incubator for 3 days. 4. Detection: CellTiter-Glo agent was added to the cell plate, and incubated at room temperature for 30 minutes to stabilize the luminous signal. PerkinElmer Envision multi-label analyzer was used for reading, wherein A represents IC$_{50}$≤nM, B represents IC$_{50}$ is 10-20 nM, C represents IC$_{50}$ is 20-50 nM, D represents IC$_{50}$ is 50-1000 nM, E represents IC$_{50}$>1000 nM.

Compounds of the present disclosure were tested in the above Cell proliferation inhibition assay, and it is found that the compounds of the present disclosure have potent activity on tumor cell Ba/F3 Bcr-Abl T315I and outstanding selectivity over tumor cell Ba/F3 parental. Results of the inhibitory effect of representative examples on the in vitro proliferation of cancer cells were summarized in Table 2 below.

TABLE 2

| Example No. | Ba/F3 parental (nM) | Ba/F3 Bcr-Abl $^{T315I}$ (nM) | Selectivity [Ba/F3 (parental/Bcr-Abl $^{T315I}$)] |
|---|---|---|---|
| Example 1 | E | C | 50~100 |
| Example 4 | E | D | 0~50 |
| Example 5 | D | A | 100~150 |
| Example 6 | E | B | 100~150 |
| Example 9 | E | B | 150~500 |
| Example 10 | E | B | 150~500 |
| Example 11 | E | B | >500 |
| Example 12 | E | C | 150~500 |
| Example 13 | E | C | 100~150 |
| Example 14 | E | C | 50~100 |
| Example 15 | E | C | 0~50 |
| Example 16 | E | A | 150~500 |

TABLE 2-continued

| Example No. | Ba/F3 parental (nM) | Ba/F3 Bcr-Abl $^{T315I}$ (nM) | Selectivity [Ba/F3 (parental/ Bcr-Abl $^{T315I}$)] |
|---|---|---|---|
| Example 17 | E | B | 50~100 |
| Example 18 | E | A | 100~150 |
| Example 19 | E | A | 150~500 |
| Example 21 | D | A | 50~100 |
| Example 22 | E | C | 0~50 |
| Example 24 | E | B | 150~500 |
| Example 25 | E | C | 0~50 |

Biological Example 3: Metabolic Stability Evaluation Analysis

Microsome assay: human liver microsomes: 0.5 mg/mL, Xenotech; coenzyme (NADPH/NADH): 1 mM, Sigma Life Science; magnesium chloride: 5 mM, 100 mM phosphate buffer (pH is 7.4).

Preparation of stock solution: Powder of the example compounds and the reference compound were accurately weighed, and dissolved to 5 mM with DMSO, respectively.

Preparation of phosphate buffer (100 mM, pH7.4): Preformulated 150 mL 0.5 M potassium dihydrogen phosphate and 700 mL 0.5 M dipotassium hydrogen phosphate were mixed, then the pH of the mixture was adjusted to 7.4 with 0.5 M dipotassium hydrogen phosphate. Before use, 5-fold dilution was made with ultra-pure water, and magnesium chloride was added to afford phosphate buffer (100 mM), which containing 100 mM potassium phosphate, 3.3 mM magnesium chloride, and pH is 7.4.

NADPH regeneration system solution (containing 6.5 mM NADP, 16.5 mM G-6-P, 3 U/mL G-6-P D, 3.3 mM magnesium chloride) was prepared and placed on wet ice before use.

Preparation of stop solution: Acetonitrile solution containing 50 ng/mL propranolol hydrochloride and 200 ng/mL tolbutamide (internal standard). 25057.5 µL phosphate buffer (pH 7.4) was taken into a 50 mL centrifuge tube, and 812.5 µL human liver microsome was added respectively, mixed well to afford liver microsome diluention with a protein concentration of 0.625 mg/mL.

Incubation of the sample: The stock solutions of the corresponding compounds were diluted to 0.25 mM with an aqueous solution containing 70% acetonitrile as working solutions for use. 398 µL of human liver microsome diluention was taken and added to a 96-well incubation plate (N=2), respectively, and 2 µL of 0.25 mM working solutions were then added respectively, and mixed well.

Determination of metabolic stability: 300 µL of prechilled stop solution was added to each well of a 96-well deep well plate and the plate was placed on ice as a stop plate. The 96-well incubation plate and NADPH regeneration system were placed in a 37° C. water bath, shook at 100 rpm, and pre-incubated for 5 min. 80 µL of incubation solution was taken from each well of the incubation plate and added to the stop plate, mixed well, and 20 µL of NADPH regeneration system solution was supplemented, the resulted solution was considered as sample at 0 min. Then 80 µL of NADPH regeneration system solution was added to each well of the incubation plate to start the reaction and started timing. The reaction concentration of the corresponding compound is 1 µM, and the protein concentration is 0.5 mg/mL. 100 µL reaction solution was taken at 10, 30, 90 min of reaction, respectively, and added into stop plate, the reaction was stopped with 3 min vortex.

The stop plate was centrifuged at 5000×g, 4° C. for 10 min. 100 µL of supernatant was taken to a 96-well plate where 100 µL of distilled water was added in advance, mixed well, sample analysis was carried out by LC-MS/MS.

Data analysis: LC-MS/MS system was used to detect peak area of corresponding compound and internal standard, peak area ratio of compound to internal standard was calculated. The slope was measured by plotting the natural logarithm of the remaining percentage of the compound versus time, and $t_{1/2}$ and $CL_{int}$ were calculated according to the following formula, wherein V/M means 1/protein concentration.

$$t_{1/2} = -\frac{0.693}{Slope}, \quad CL_{int} = \frac{0.693}{t_{1/2}} \bullet \frac{V}{M}, \quad t_{1/2}(\min); CL_{int}(\mu L/\min/mg).$$

Compounds of the present disclosure were tested in the above human liver microsome assay, and it is found that the compounds of the present disclosure have outstanding metabolic stability. Results of representative example compounds were summarized in Table 3 below.

TABLE 3

| | HLM | |
|---|---|---|
| Example No. | $T_{1/2}$ (min) | Clint (µL/min/mg) |
| Example 5 | 69.8 | 19.9 |
| Example 6 | 394.7 | 3.5 |
| Example 12 | 66.4 | 20.9 |
| Example 15 | 117.2 | 11.8 |
| Example 17 | 80.5 | 17.2 |
| Example 18 | 81.6 | 17.0 |
| Example 22 | 227.8 | 6.1 |
| Example 25 | 181.8 | 7.6 |

The above is detailed description of the present disclosure in conjunction with specific embodiments, and it cannot be assumed that the specific implementation of the present disclosure is limited to these descriptions. For ordinary person skilled in the technical field to which the present disclosure pertains, without deviating from the concept of the present disclosure, various simple deductions or substitutions may be made, which should be regarded as falling within the protection scope of the present disclosure.

What is claimed is:

1. A compound of formula (I), or pharmaceutically acceptable salts, stereoisomers, solvates, hydrates, crystal forms, prodrugs or isotopic variants thereof:

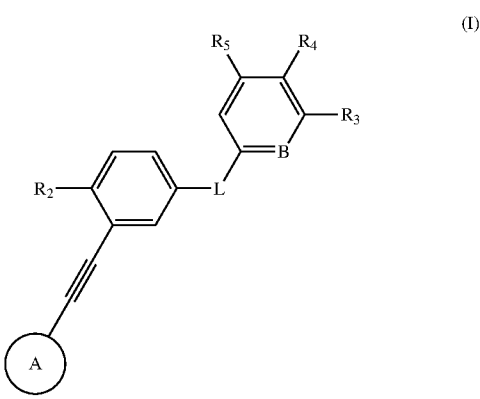

wherein, ring A is:

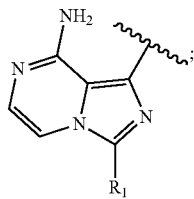

$R_1$ is selected from $C_{1-6}$ alkyl, $C_{3-7}$ cycloalkyl, 3- to 7-membered heterocyclyl, $C_{6-10}$ aryl or 5- to 10-membered heteroaryl, wherein the groups are optionally substituted by one or more $R_{1a}$;
$R_2$ is H or $C_{1-6}$ alkyl;
L is selected from —C(O)N($R_{1b}$)—, —N($R_{1b}$)C(O)— or —N($R_{1b}$)C(O)N($R_{1b}$)—;
B is selected from CH or N;
$R_3$ is selected from $C_{1-6}$ alkyl or $C_{1-6}$ haloalkyl;
$R_4$ and $R_5$ are selected from:
1) $R_5$ is H, $R_4$ is selected from H, $C_{1-6}$ alkyl, —$C_{0-2}$ alkylene-$C_{3-7}$ cycloalkyl, —$C_{0-2}$ alkylene-3- to 7-membered heterocyclyl or —$C_{0-2}$ alkylene-$NR_{1c}R_{2c}$, wherein the groups are optionally substituted by one or more $R_{1d}$; or,
2) $R_4$ is H, $R_5$ is selected from H or 5- to 6-membered heteroaryl containing one or more N, O or S heteroatoms, wherein the 5- to 6-membered heteroaryl ring is optionally substituted by one or more $R_{1d}$;
each $R_{1a}$ is independently selected from H, halogen, oxo, —$C_{0-6}$ alkylene-$OR_a$, —$C_{0-6}$ alkylene-$NR_bR_c$, —$C_{0-6}$ alkylene-C(O)$R_a$, —$C_{0-6}$ alkylene-C(O)$OR_a$, —$C_{0-6}$ alkylene-C(O)$NR_bR_c$, $C_{1-6}$ alkyl, $C_{1-6}$ haloalkyl, —$C_{0-6}$ alkylene-$C_{3-6}$ cycloalkyl or —$C_{0-6}$ alkylene-3- to 7-membered heterocyclyl; or two or more $R_{1a}$ together with the atom to which they attached form a $C_{3-7}$ cycloalkyl or 3- to 7-membered heterocyclyl;
each $R_{1b}$ is independently selected from H, —$C_{0-6}$ alkylene-$OR_a$, —$C_{0-6}$ alkylene-$NR_bR_c$, —$C_{0-6}$ alkylene-C(O)$R_a$, —$C_{0-6}$ alkylene-C(O)$OR_a$, —$C_{0-6}$ alkylene-C(O)$NR_bR_c$, $C_{1-6}$ alkyl, $C_{1-6}$ haloalkyl, —$C_{0-6}$ alkylene-$C_{3-6}$ cycloalkyl or —$C_{0-6}$ alkylene-3- to 7-membered heterocyclyl; or two or more $R_{1b}$ together with the atom to which they attached form a $C_{3-7}$ cycloalkyl or 3- to 7-membered heterocyclyl;
$R_{1c}$ and $R_2$ are each independently selected from H, halogen, —$C_{0-6}$ alkylene-CN, —$C_{0-6}$ alkylene-$OR_a$, —$C_{0-6}$ alkylene-$SR_a$, —$C_{0-6}$ alkylene-$NR_bR_c$, —$C_{0-6}$ alkylene-C(O)$R_a$, —$C_{0-6}$ alkylene-C(O)$OR_a$, —$C_{0-6}$ alkylene-C(O)$NR_bR_c$, $C_{1-6}$ alkyl, $C_{1-6}$ haloalkyl, $C_{2-6}$ alkenyl, $C_{2-6}$ alkynyl, —$C_{0-6}$ alkylene-$C_{3-6}$ cycloalkyl, —$C_{0-6}$ alkylene-3- to 7-membered heterocyclyl, —$C_{0-6}$ alkylene-$C_{6-10}$ aryl or —$C_{0-6}$ alkylene-5- to 10-membered heteroaryl; or, $R_{1c}$, $R_2$ together with the nitrogen atom to which they attached form a $C_{3-7}$ cycloalkyl or 3- to 7-membered heterocyclyl;
each $R_{1d}$ is independently selected from H, halogen, —$C_{0-6}$ alkylene-CN, —$C_{0-6}$ alkylene-$OR_a$, —$C_{0-6}$ alkylene-$SR_a$, —$C_{0-6}$ alkylene-$NR_bR_c$, —$C_{0-6}$ alkylene-C(O)$R_a$, —$C_{0-6}$ alkylene-C(O)$OR_a$, —$C_{0-6}$ alkylene-C(O)$NR_bR_c$, $C_{1-6}$ alkyl, $C_{1-6}$ haloalkyl, $C_{2-6}$ alkenyl, $C_{2-6}$ alkynyl, —$C_{0-6}$ alkylene-$C_{3-6}$ cycloalkyl, —$C_{0-6}$ alkylene-3- to 7-membered heterocyclyl, —$C_{0-6}$ alkylene-$C_{6-10}$ aryl or —$C_{0-6}$ alkylene-5- to 10-membered heteroaryl; or two or more $R_{1d}$ together with the atom to which they attached form a $C_{3-7}$ cycloalkyl or 3- to 7-membered heterocyclyl;
$R_a$, $R_b$ and $R_c$ are independently selected from H, $C_{1-6}$ alkyl, $C_{1-6}$ haloalkyl, $C_{3-7}$ cycloalkyl, 3- to 7-membered heterocyclyl, $C_{6-10}$ aryl or 5- to 10-membered heteroaryl.

2. The compound according to claim 1, wherein, $R_1$ is selected from $C_{1-4}$ alkyl, $C_{4-6}$ cycloalkyl or 5- to 6-membered heterocyclyl, wherein the groups are optionally substituted by one or more $R_{1a}$;
alternatively, $R_1$ is selected from methyl, ethyl, isopropyl, cyclopentyl, cyclohexyl, tetrahydrofuranyl, piperidinyl, piperazinyl or morpholinyl, wherein the said groups are optionally substituted by one or more —OH.

3. The compound according to claim 1, wherein, $R_2$ is selected from H or $C_{1-4}$ alkyl, $R_3$ is $C_1$-4 fluoroalkyl, L is selected from —C(O)N($R_{1b}$)—, —N($R_{1b}$)C(O)— or —N($R_{1b}$)C(O)N($R_{1b}$)—, B is selected from CH or N, wherein $R_{1b}$ is selected from H or $C_{1-4}$ alkyl;
alternatively, $R_2$ is selected from H or methyl, $R_3$ is trifluoromethyl, L is selected from —C(O)NH—, —NHC(O)— or —NHC(O)NH—, B is CH.

4. The compound according to claim 1, wherein, $R_5$ is H, $R_4$ is selected from H, $C_{1-6}$ alkyl or —$C_{0-2}$ alkylene-$NR_{1c}R_{2c}$; wherein the groups are optionally substituted by one or more $R_{1d}$.

5. The compound of claim 4, wherein, $R_4$ is H.

6. The compound of claim 4, wherein, $R_4$ is —$C_{1-4}$ alkyl;
alternatively, $R_4$ is selected from methyl, ethyl, isopropyl or tert-butyl.

7. The compound of claim 4, wherein, $R_4$ is selected from —$CH_2$—$NR_{1c}R_{2c}$; wherein, $R_{1c}$ and $R_2$ are each independently selected from $C_{1-6}$ alkyl, $C_{3-6}$ cycloalkyl or 3- to 7-membered heterocyclyl, or, $R_{1c}$, $R_2$ together with the nitrogen atom to which they attached form a $C_{3-7}$ cycloalkyl or 5- to 6-membered heterocyclyl;
alternatively, $R_4$ is selected from the following groups:

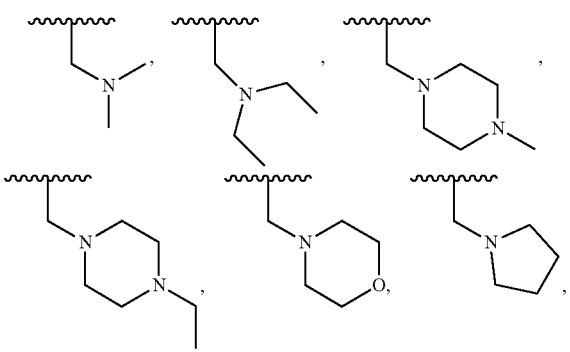

8. The compound according to claim 1, wherein, $R_4$ is H, $R_5$ is selected from H or 5- to 6-membered heteroaryl ring containing one or more N heteroatoms; wherein the 5- to 6-membered heteroaryl ring is optionally substituted by one or more $R_{1d}$.

9. The compound of claim 8, wherein, $R_5$ is 5-membered heteroaryl ring containing one or more N heteroatoms, wherein the 5-membered heteroaryl ring is optionally substituted by one or more $R_{1d}$;
alternatively, $R_5$ is imidazolyl, which is optionally substituted by one or more $R_{1d}$.

10. A compound of formula (III-a):

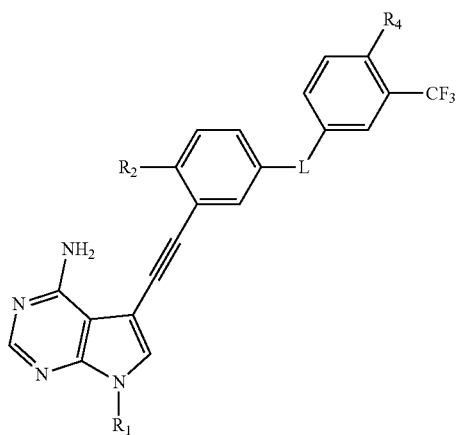

wherein, $R_1$ is selected from $C_{1-4}$ alkyl or $C_{4-6}$ cycloalkyl, wherein the groups are optionally substituted by one or more —OH;

$R_2$ is selected from H or $C_{1-4}$ alkyl;

$R_4$ is selected from H or $C_{1-4}$ alkyl;

L is —C(O)NH—;

or the pharmaceutically acceptable salts, stereoisomers, solvates, hydrates, crystal forms, prodrugs or isotopic variants thereof.

11. A compound of formula (III-b):

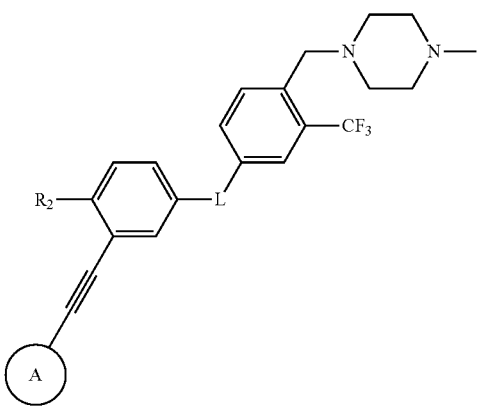

wherein,
ring A is

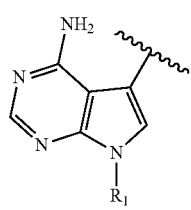

$R_1$ is methyl or ethyl;

$R_2$ is selected from H or $C_{1-4}$ alkyl;

L is selected from —C(O)NH— or —NHC(O)—;

or the pharmaceutically acceptable salts, stereoisomers, solvates, hydrates, crystal forms, prodrugs or isotopic variants thereof.

12. A compound of formula (III-c):

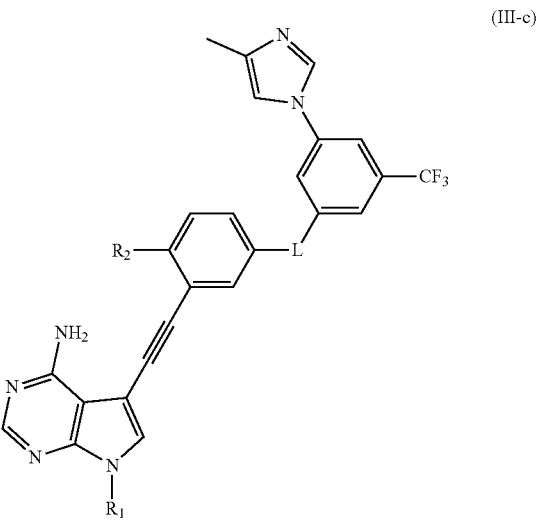

wherein, $R_1$ is selected from $C_{1-4}$ alkyl or $C_{4-6}$ cycloalkyl, wherein the said groups are optionally substituted by one or more —OH;

$R_2$ is selected from H or $C_{1-4}$ alkyl;

L is selected from —C(O)NH— or —NHC(O)—;

or the pharmaceutically acceptable salts, stereoisomers, solvates, hydrates, crystal forms, prodrugs or isotopic variants thereof.

13. The compound of claim 1, which is selected from the following compounds:

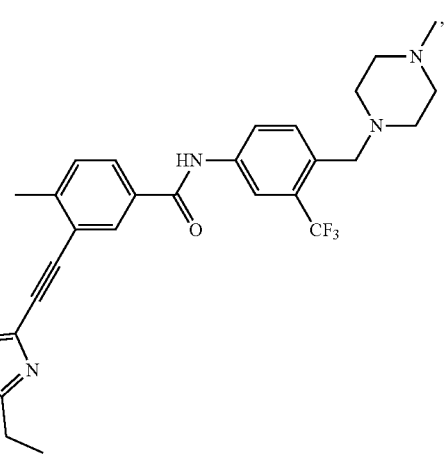

-continued

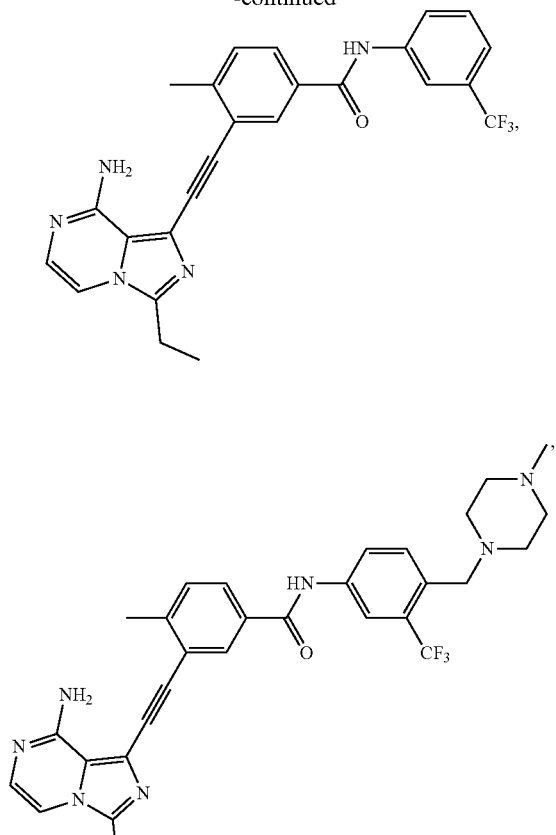

or the pharmaceutically acceptable salts, stereoisomers, solvates, hydrates, crystal forms, prodrugs or isotopic variants thereof.

14. A pharmaceutical composition, comprising a compound according to claim 1 or the pharmaceutically acceptable salts, stereoisomers, solvates, hydrates, crystal forms, prodrugs or isotopic variants thereof, and pharmaceutically acceptable excipient(s);

alternatively, which also comprises other therapeutic agent(s).

15. The compound of claim 10, which is selected from the following compounds:

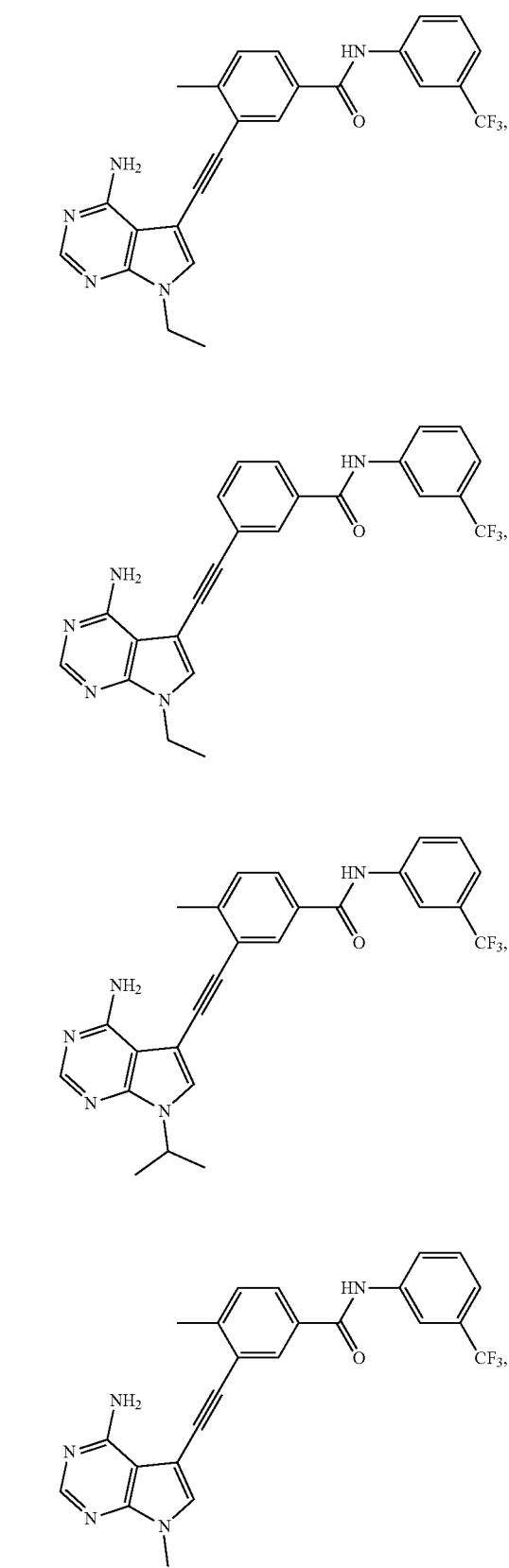

81
-continued
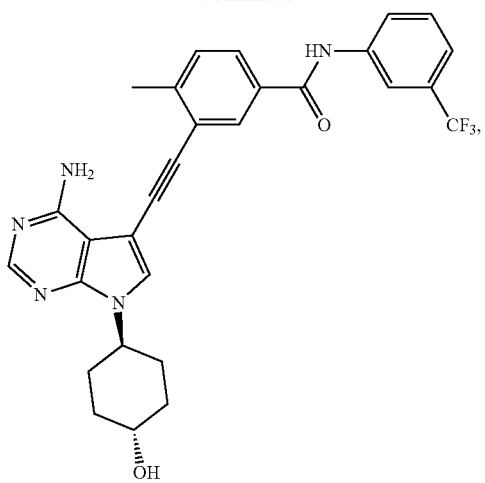
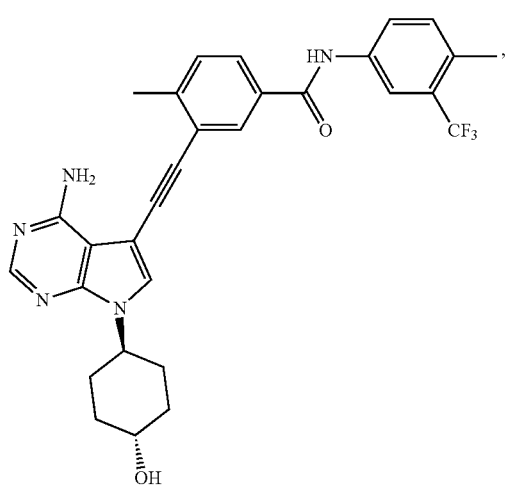
or the pharmaceutically acceptable salts, stereoisomers, solvates, hydrates, crystal forms, prodrugs or isotopic variants thereof.
16. The compound of claim 11, which is selected from the following compounds:
82
-continued
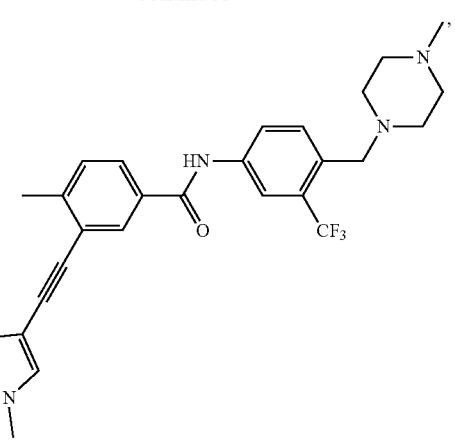
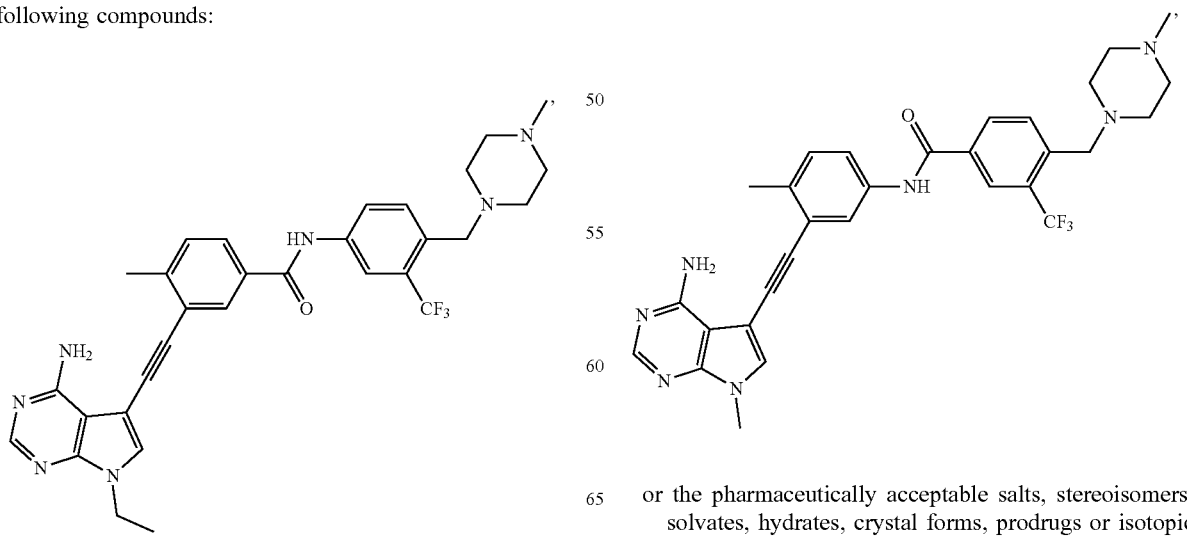
or the pharmaceutically acceptable salts, stereoisomers, solvates, hydrates, crystal forms, prodrugs or isotopic variants thereof.

17. The compound of claim 12, which is selected from the following compounds:
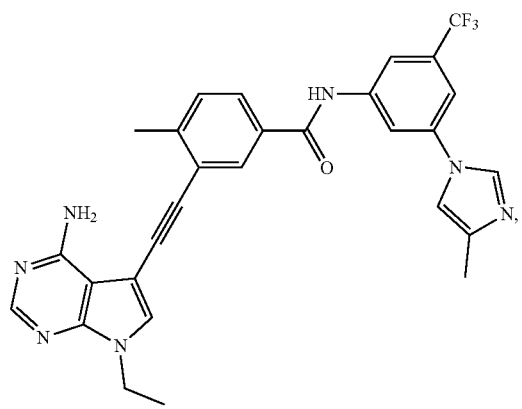
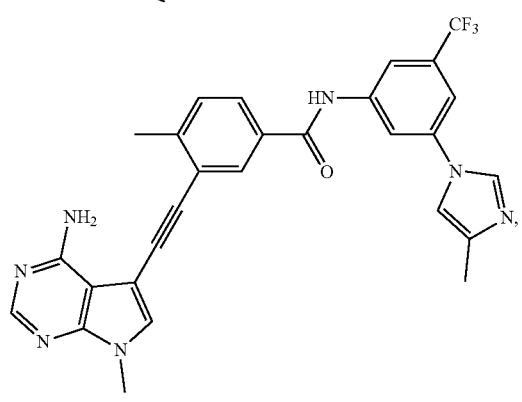
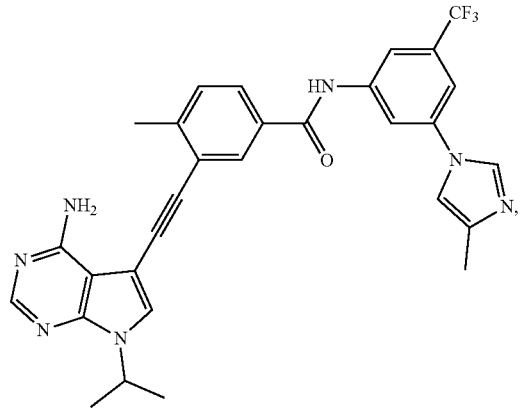
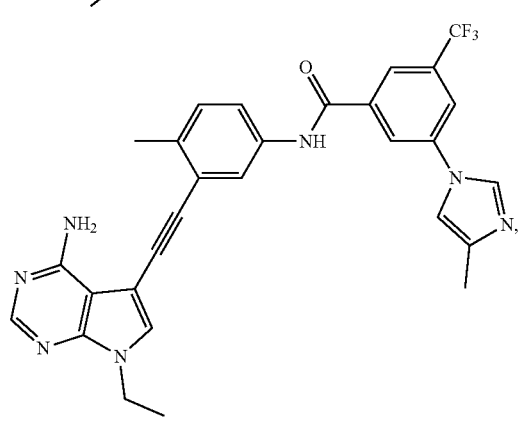
or the pharmaceutically acceptable salts, stereoisomers, solvates, hydrates, crystal forms, prodrugs or isotopic variants thereof.
18. A compound, which is selected from the following compounds:
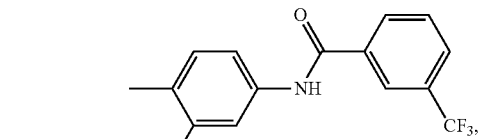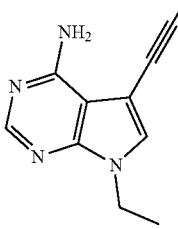
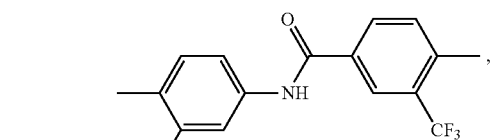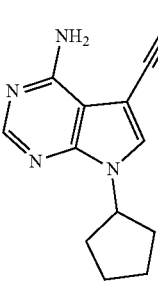
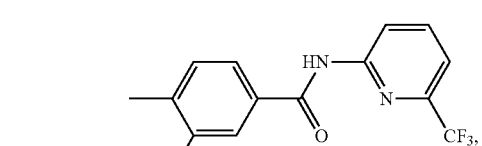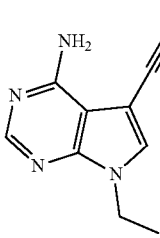

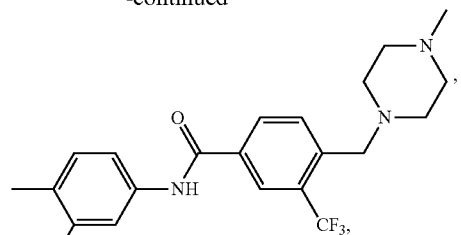
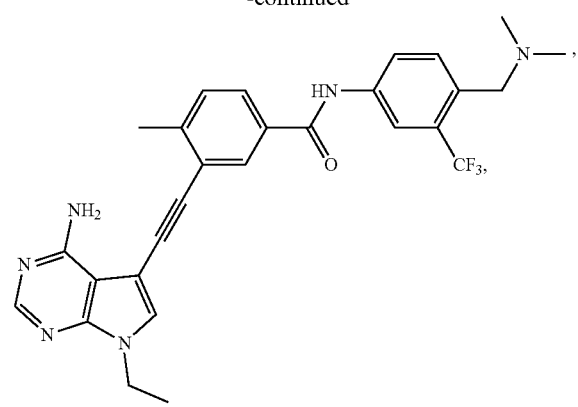
or the pharmaceutically acceptable salts, stereoisomers, solvates, hydrates, crystal forms, prodrugs or isotopic variants thereof.
* * * * *